US012644892B2

(12) United States Patent
Serie et al.

(10) Patent No.: US 12,644,892 B2
(45) Date of Patent: Jun. 2, 2026

(54) BIOMARKERS FOR CLEAR CELL RENAL CELL CARCINOMA

(71) Applicant: Venn Biosciences Corporation, South San Francisco, CA (US)

(72) Inventors: Daniel Serie, South San Francisco, CA (US); Klaus Lindpaintner, South San Francisco, CA (US)

(73) Assignee: Venn Biosciences Corporation, South San Francisco, CA (US)

( * ) Notice: Subject to any disclaimer, the term of this patent is extended or adjusted under 35 U.S.C. 154(b) by 901 days.

(21) Appl. No.: 17/910,768

(22) PCT Filed: Mar. 12, 2021

(86) PCT No.: PCT/US2021/022071
§ 371 (c)(1),
(2) Date: Sep. 9, 2022

(87) PCT Pub. No.: WO2021/183859
PCT Pub. Date: Sep. 16, 2021

(65) Prior Publication Data
US 2023/0112866 A1     Apr. 13, 2023

Related U.S. Application Data

(60) Provisional application No. 62/989,510, filed on Mar. 13, 2020.

(51) Int. Cl.
| | |
|---|---|
| *G01N 33/68* | (2006.01) |
| *C12Q 1/6872* | (2018.01) |
| *G01N 33/57525* | (2026.01) |

(52) U.S. Cl.
CPC ....... *G01N 33/6848* (2013.01); *C12Q 1/6872* (2013.01); *G01N 33/57525* (2026.01); *C12Q 2600/112* (2013.01)

(58) Field of Classification Search
None
See application file for complete search history.

(56) References Cited

U.S. PATENT DOCUMENTS

| | | |
|---|---|---|
| 2016/0238615 A1 | 8/2016 | Zang et al. |
| 2019/0101544 A1 | 4/2019 | Danan-leon et al. |

FOREIGN PATENT DOCUMENTS

| | | |
|---|---|---|
| WO | 2019046814 A1 | 3/2019 |
| WO | 2019079639 A1 | 4/2019 |

OTHER PUBLICATIONS

Belczacka, I. et al. Urinary Glycopeptide Analysis for the Investigation of Novel Biomarkers, Proteomics Clin. Appl. 2019, 13, 1800111 (Year: 2019).*
Dube, D.H. et al. (Jun. 2005). "Glycans in Cancer and Inflammation—Potential for Therapeutics and Diagnostics," Nature Rev. Drug Disc. 4(6):477-488.

(Continued)

*Primary Examiner* — Xiaoyun R Xu
(74) *Attorney, Agent, or Firm* — MEDLER FERRO WOODHOUSE & MILLS PLLC

(57) ABSTRACT

Set forth herein are methods useful for identifying disease biomarkers, particularly for diseases such as clear cell renal cell carcinoma (ccRCC). In some examples, the methods set forth herein are useful for monitoring the prognosis of patients having disease such as ccRCC.

35 Claims, 55 Drawing Sheets

Specification includes a Sequence Listing.

(56)     References Cited

OTHER PUBLICATIONS

International Preliminary Report on Patentability, issued Sep. 6, 2022, for PCT Application No. PCT/US2021/022071, filed Mar. 12, 2021, 13 pages.
International Search Report and Written Opinion, mailed Jul. 28, 2021, for PCT Application No. PCT/US2021/022071, filed Mar. 12, 2021, 18 pages.
Li, Q. et al. (Apr. 16, 2019, e-pub. Mar. 27, 2019). "Site-Specific Glycosylation Quantitation of 50 Serum Glycoproteins Enhanced by Predictive Glycopeptidomics for Improved Disease Biomarker Discovery," Analytical Chemistry 91(8):5433-5445.
Miyamoto, S. et al. (Jan. 5, 2018, e-pub. Dec. 5, 2017). "Heterogeneity and Site Identification on N-Glycans Attached to IgG and IgA Isolated From Ovarian Cancer Malignant Ascites Fluids," J. Proteome Res. 17(1):222-233, 17 pages.
Ruhaak, L.R. et al. (Mar. 4, 2016, e-pub. Oct. 12, 2017). "Protein-Specific Differential Glycosylation of Immunoglobulins in Serum of Ovarian Cancer Patients," Journal of Proteome Research 15(3):1002-1010, 19 pages.

Varki, A. et al. (2015). "Symbol Nomenclature for Graphical Representation of Glycans," Glycobiology 25(12):1323-1324.
Wu, Z. et al. (2020). "PB-Net: Automatic Peak Integration by Sequential Deep Learning for Multiple Reaction Monitoring," Journal of Proteomics 223:103820, 8 pages.
Yogesh, K.V. (Sep. 25, 2018). "Synthesis of Complex Glycopeptides Toward Novel Cancer Marker Discovery," Hokkaido University Doctoral Thesis, 79 pages.
Clark et al. "Integrated proteogenomic characterization of clear cell renal cell carcinoma." Cell 179.4: 964-983 (2019).
Gbormittah et al. "Clusterin glycopeptide variant characterization reveals significant site-specific glycan changes in the plasma of clear cell renal cell carcinoma." *Journal Of Proteome Research* 14.6: 2425-2436 (2015).
Serie et al. "Novel plasma glycoprotein biomarkers predict progression-free survival in surgically resected clear cell renal cell carcinoma." *Urologic Oncology: Seminars and Original Investigations*. vol. 40. No. 4. Elsevier (2022).
European Search Report issued in EP 21 76 8409/ PCT/US2021/022071 mailed on Apr. 18, 2024.

* cited by examiner

No. at risk

| | | | | | |
|---|---|---|---|---|---|
| Below cutoff | 68 | 51 | 31 | 6 | 2 |
| Above cutoff | 9 | 2 | 2 | | |

No. at risk

| | | | | | |
|---|---|---|---|---|---|
| Below cutoff | 49 | 36 | 26 | 4 | 2 |
| Above cutoff | 28 | 17 | 7 | 2 | |

FIG. 42

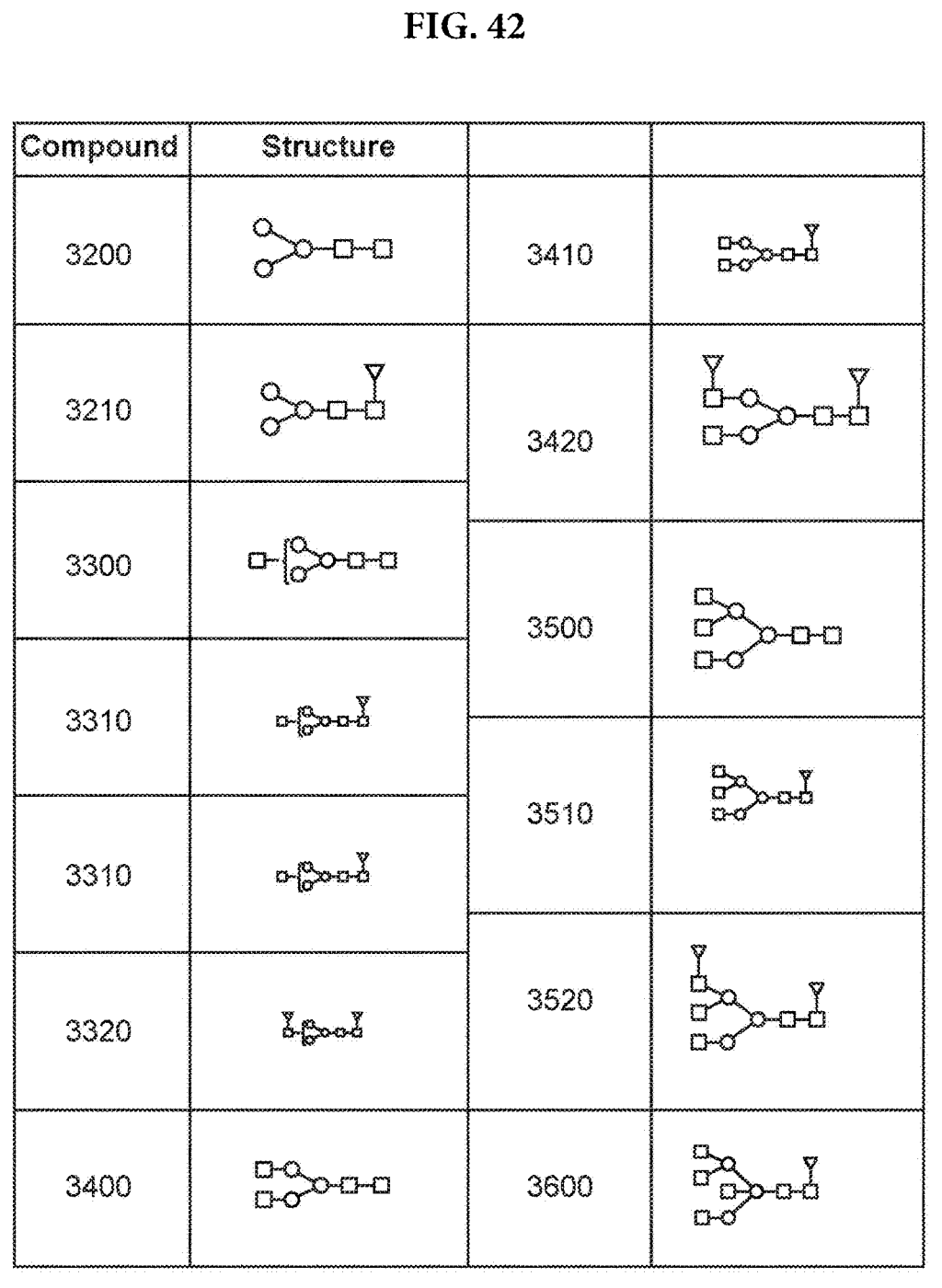

| Compound | Structure | | |
|---|---|---|---|
| 3200 | | 3410 | |
| 3210 | | 3420 | |
| 3300 | | 3500 | |
| 3310 | | 3510 | |
| 3310 | | 3520 | |
| 3320 | | 3600 | |
| 3400 | | | |

Figure 43:
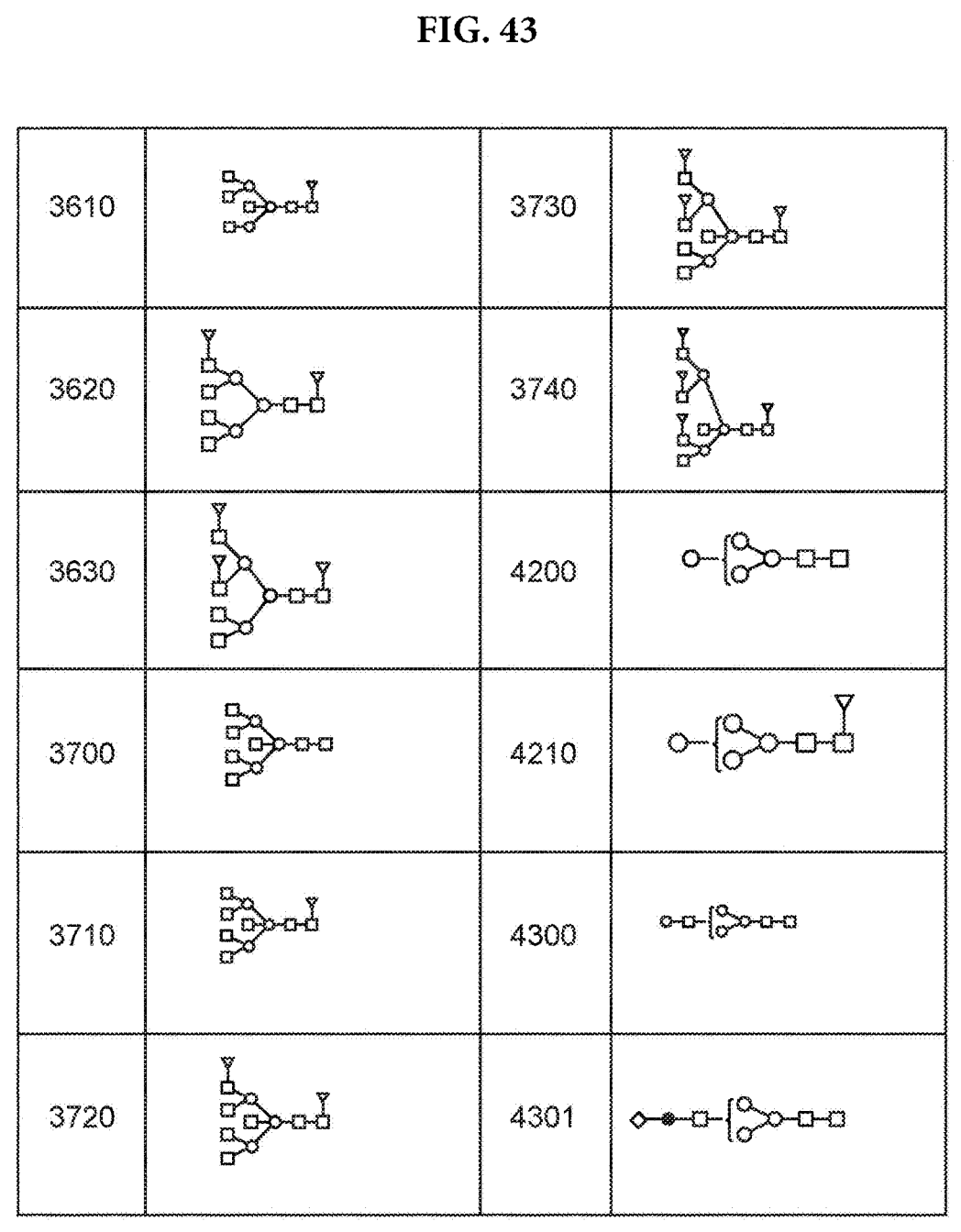

Figure 44:
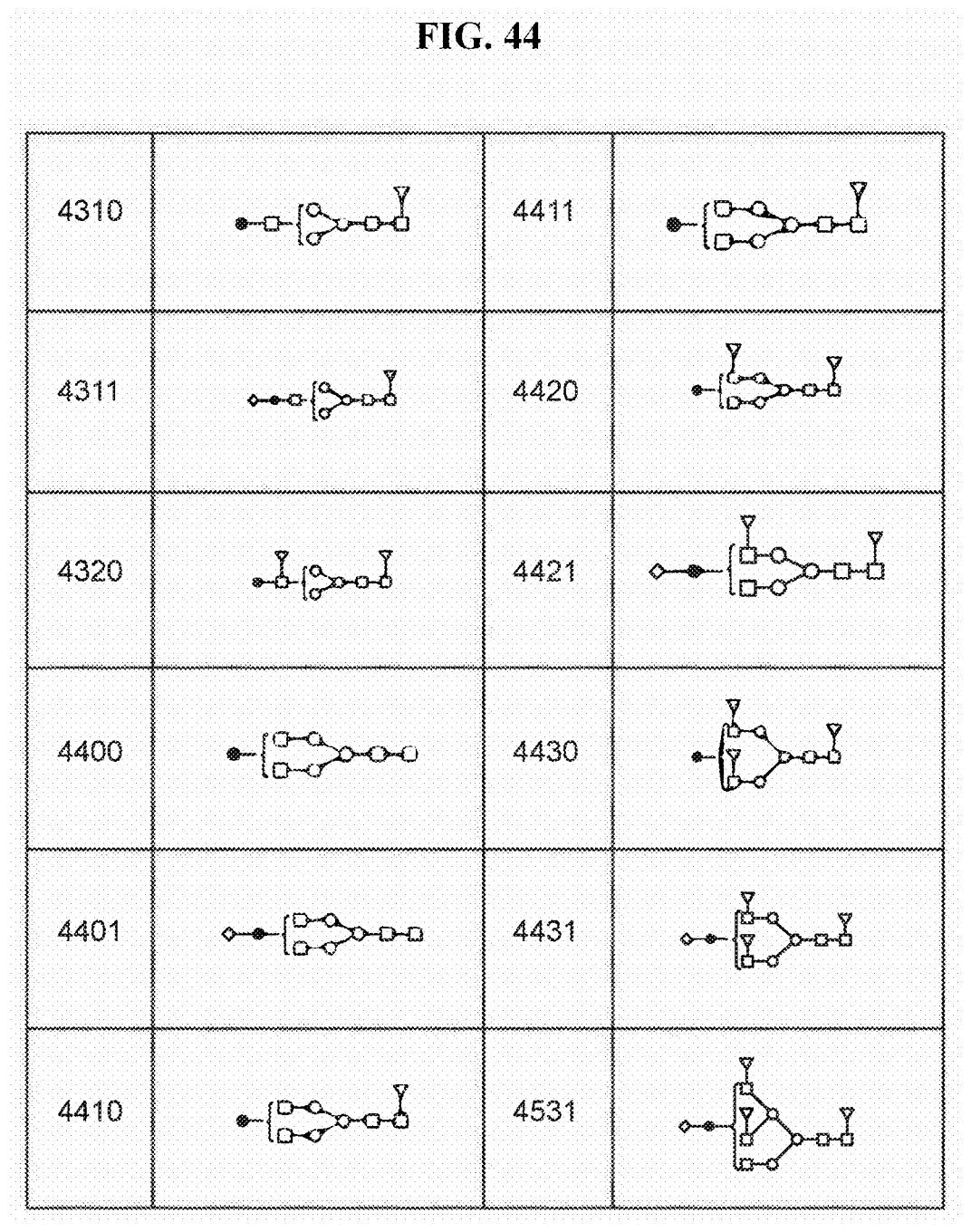

Figure 45:
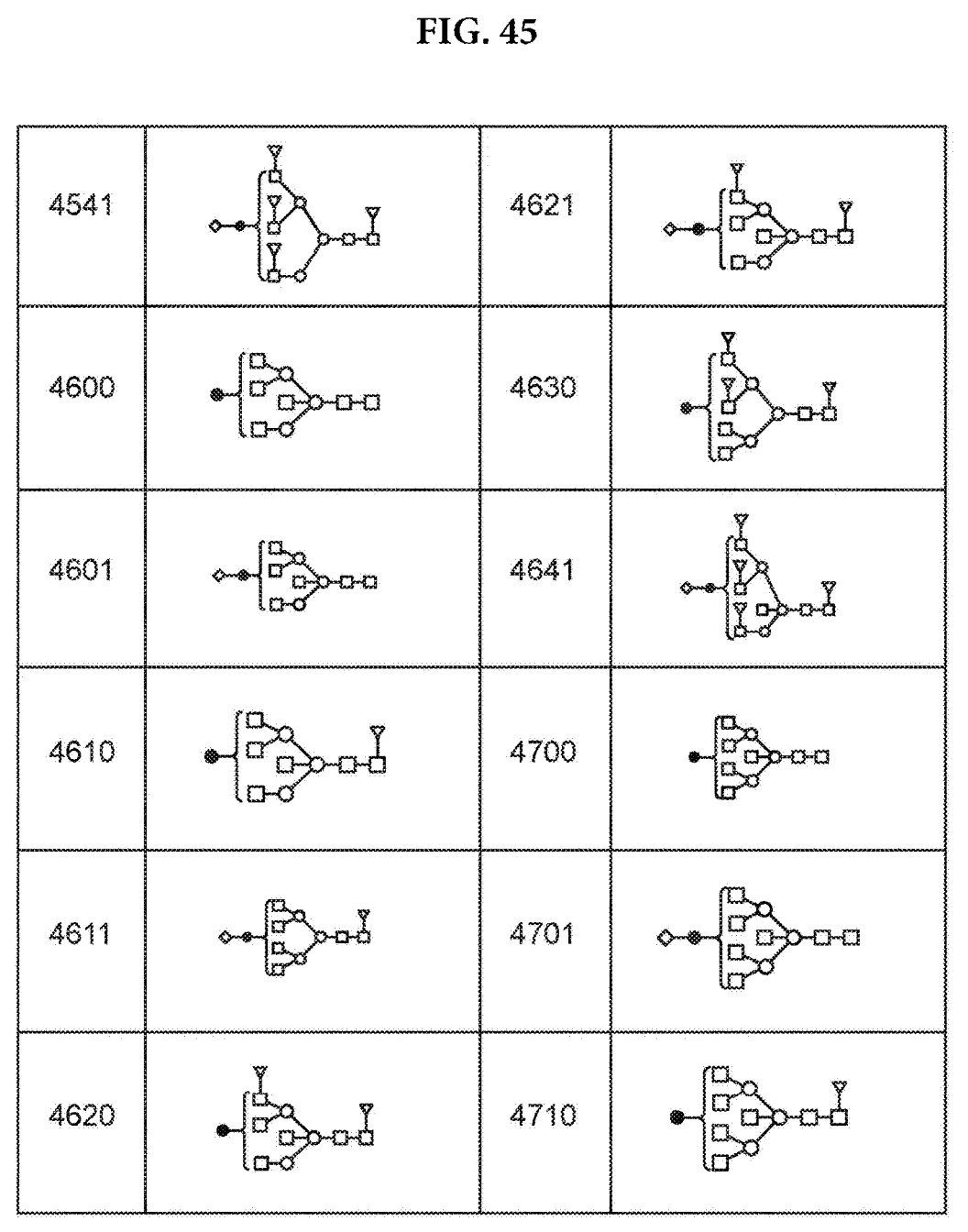

Figure 46:
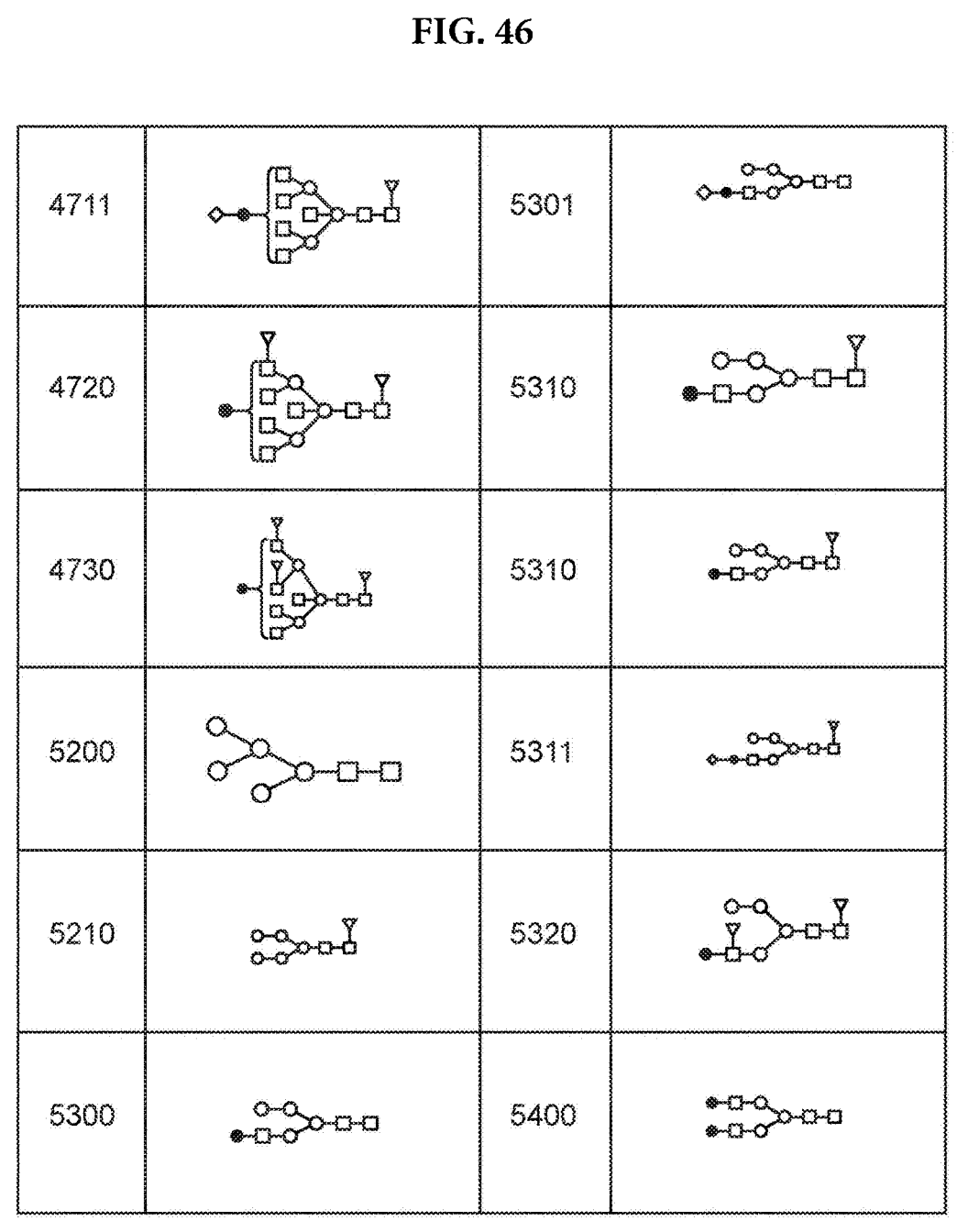

Figure 47:
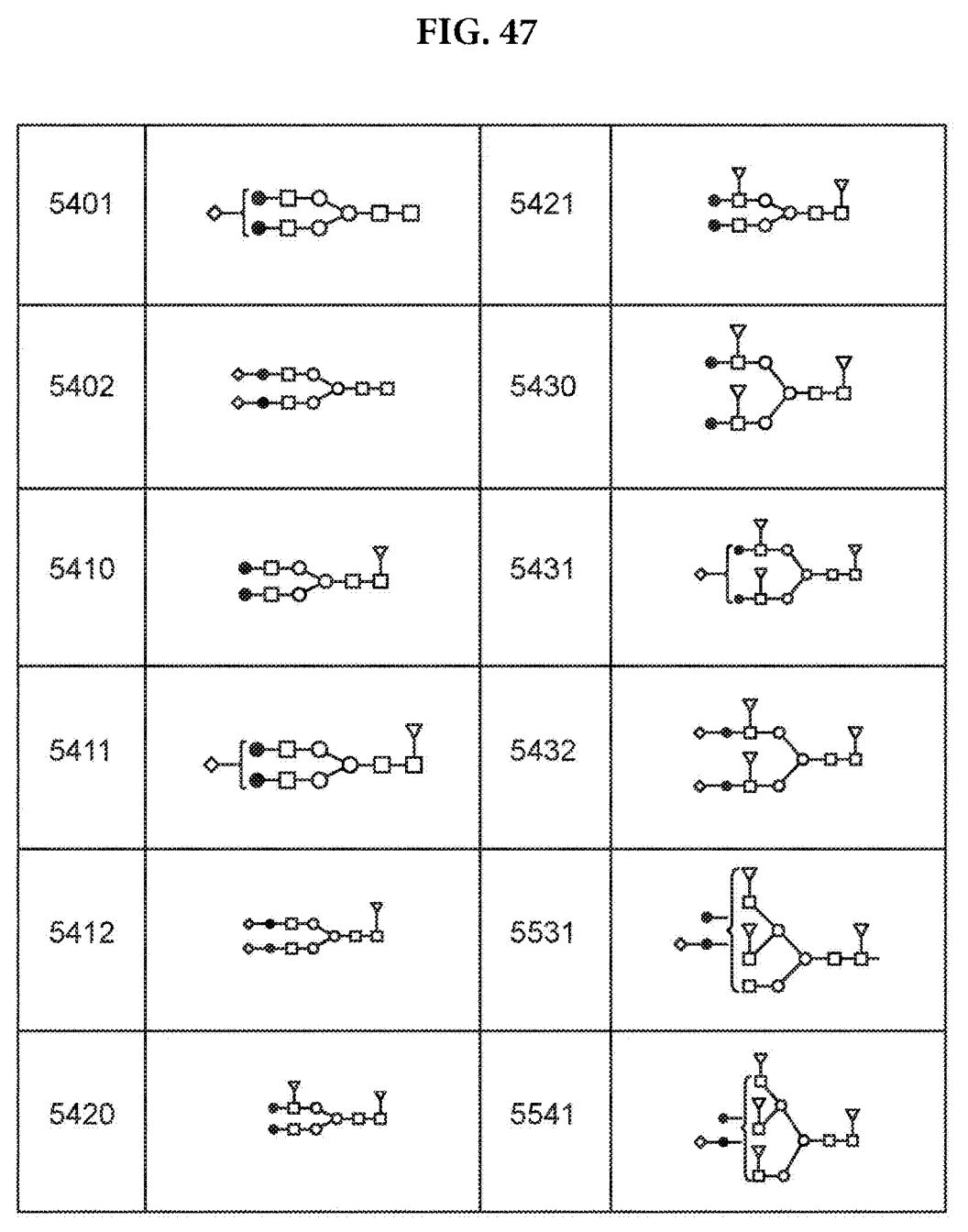

Figure 48:
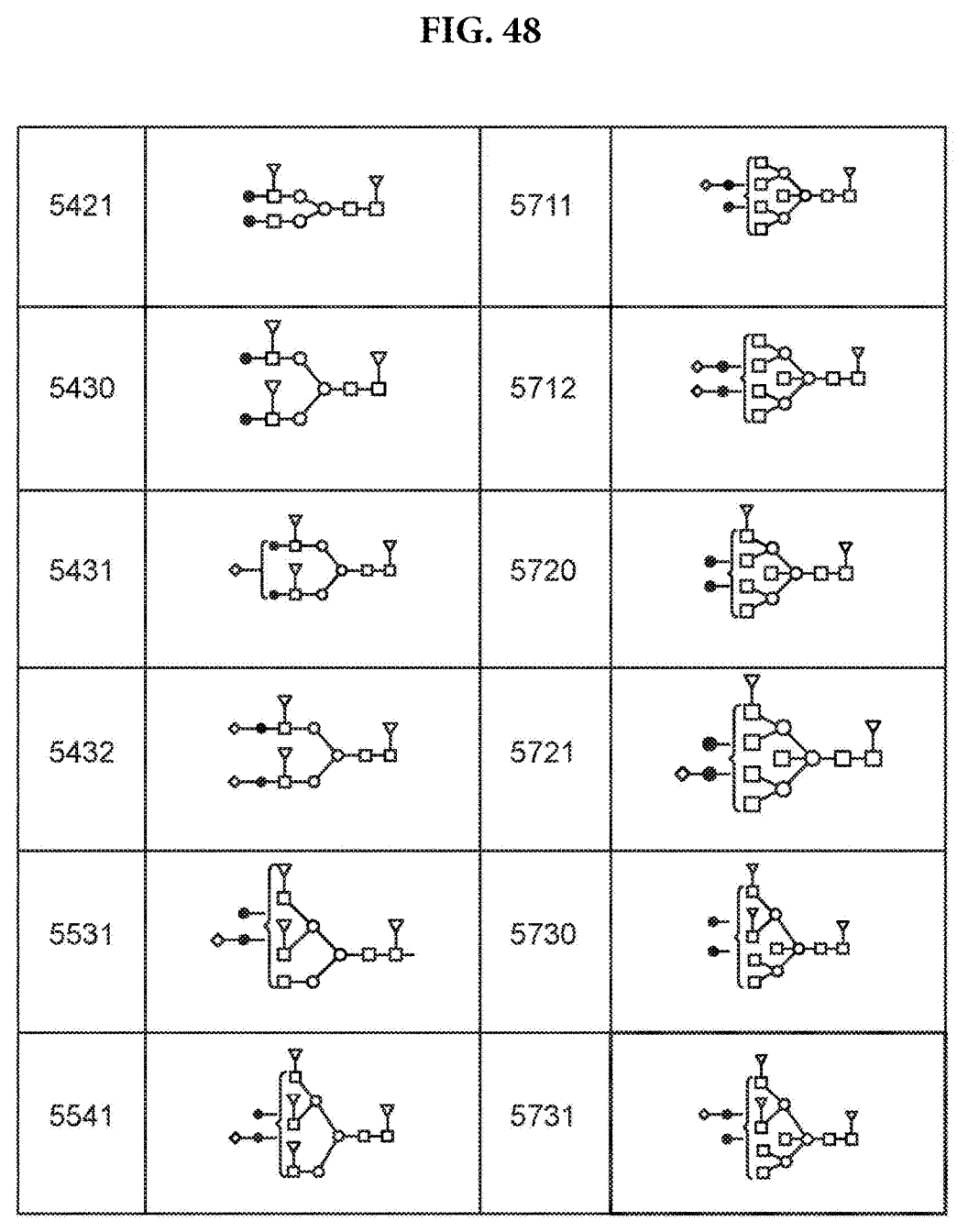

Figure 49:
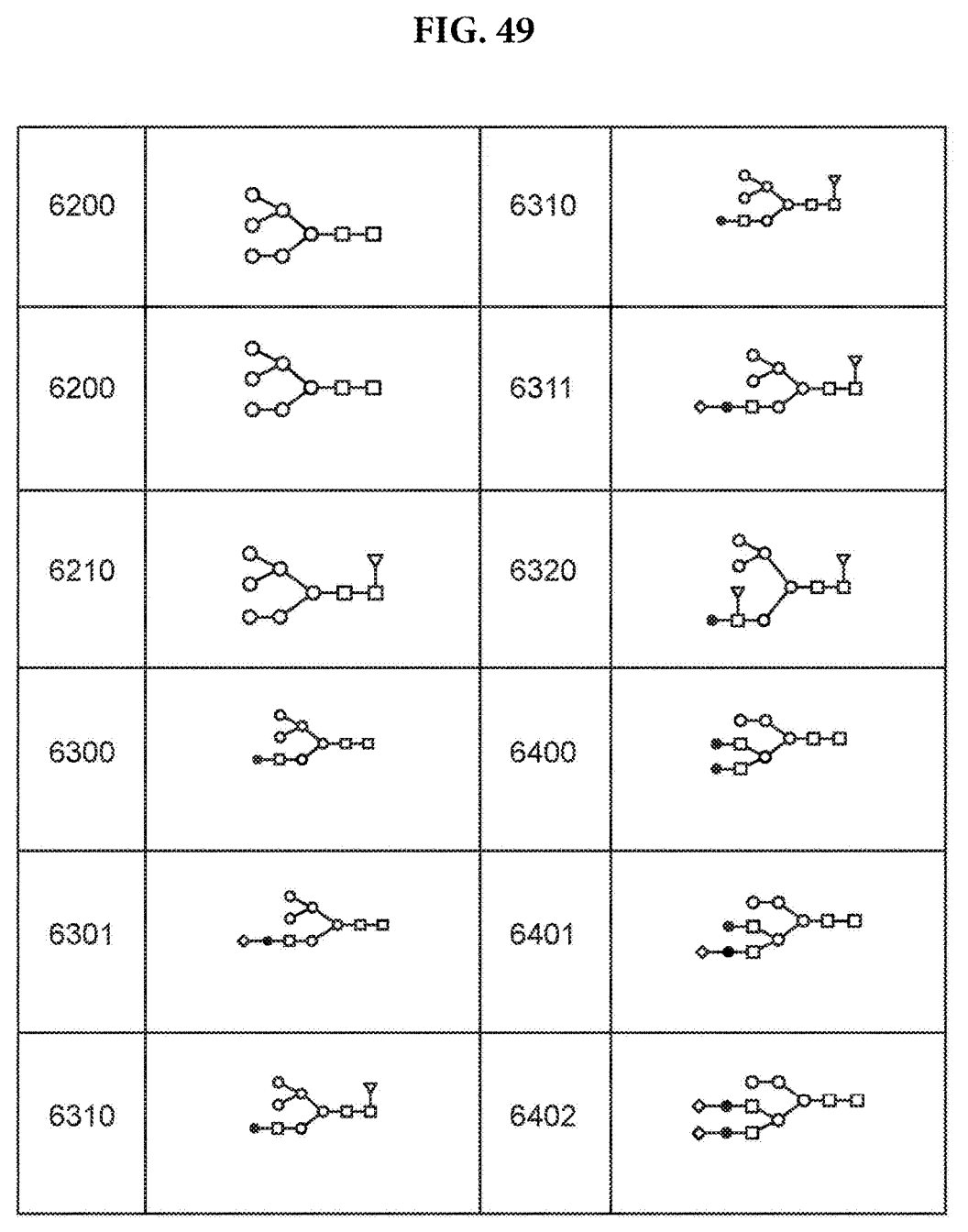

Figure 50:
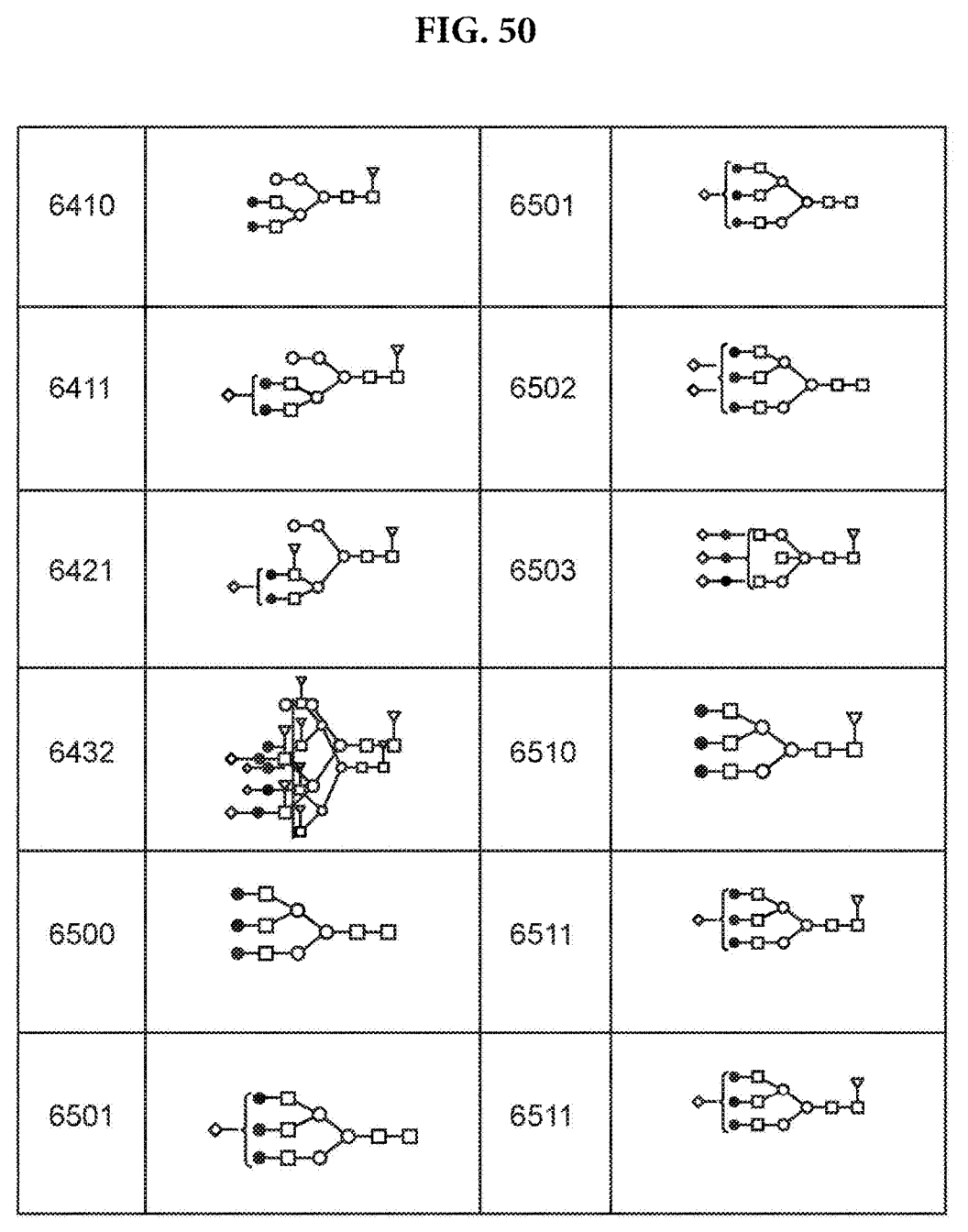

Figure 51:
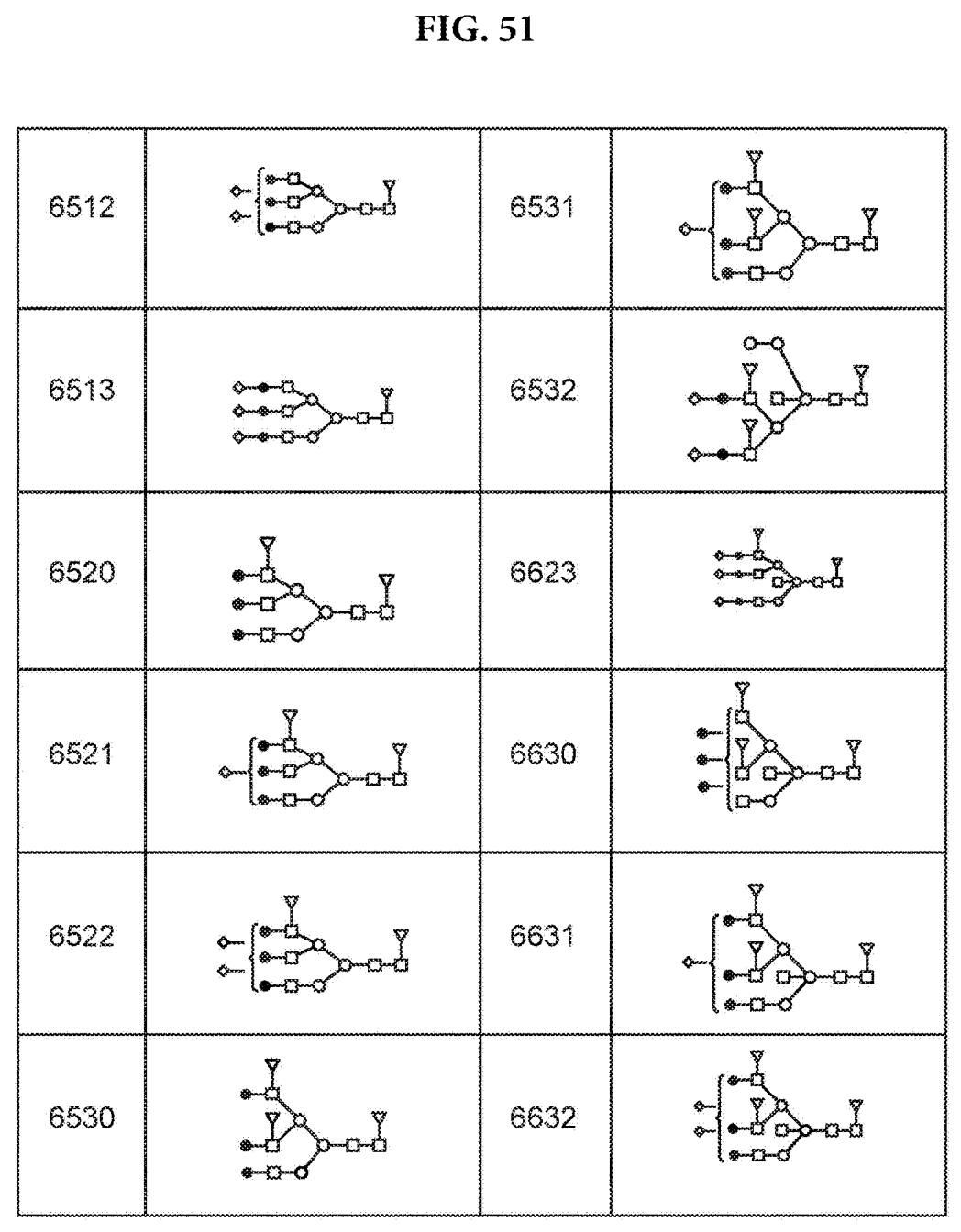

Figure 52:
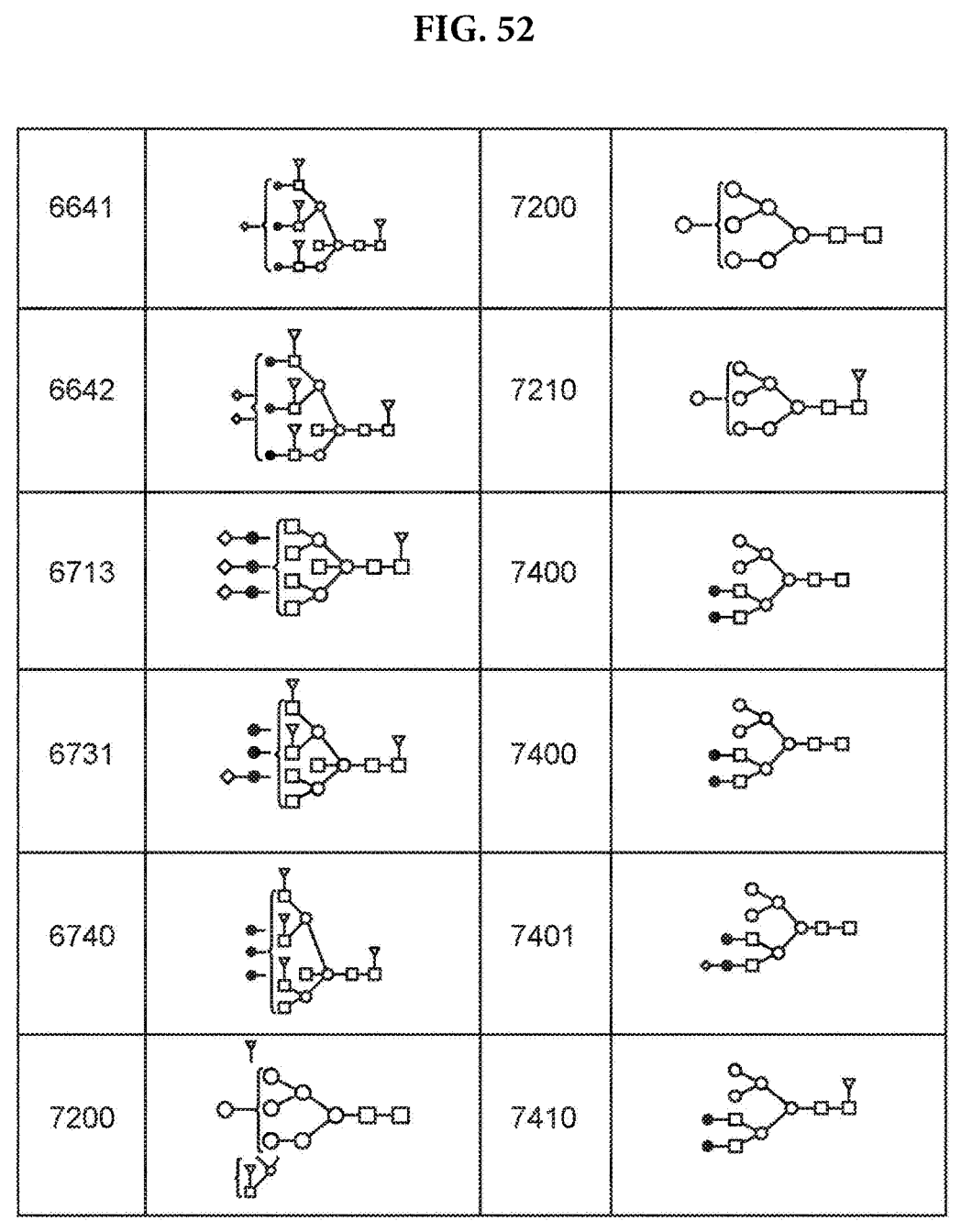

Figure 53:
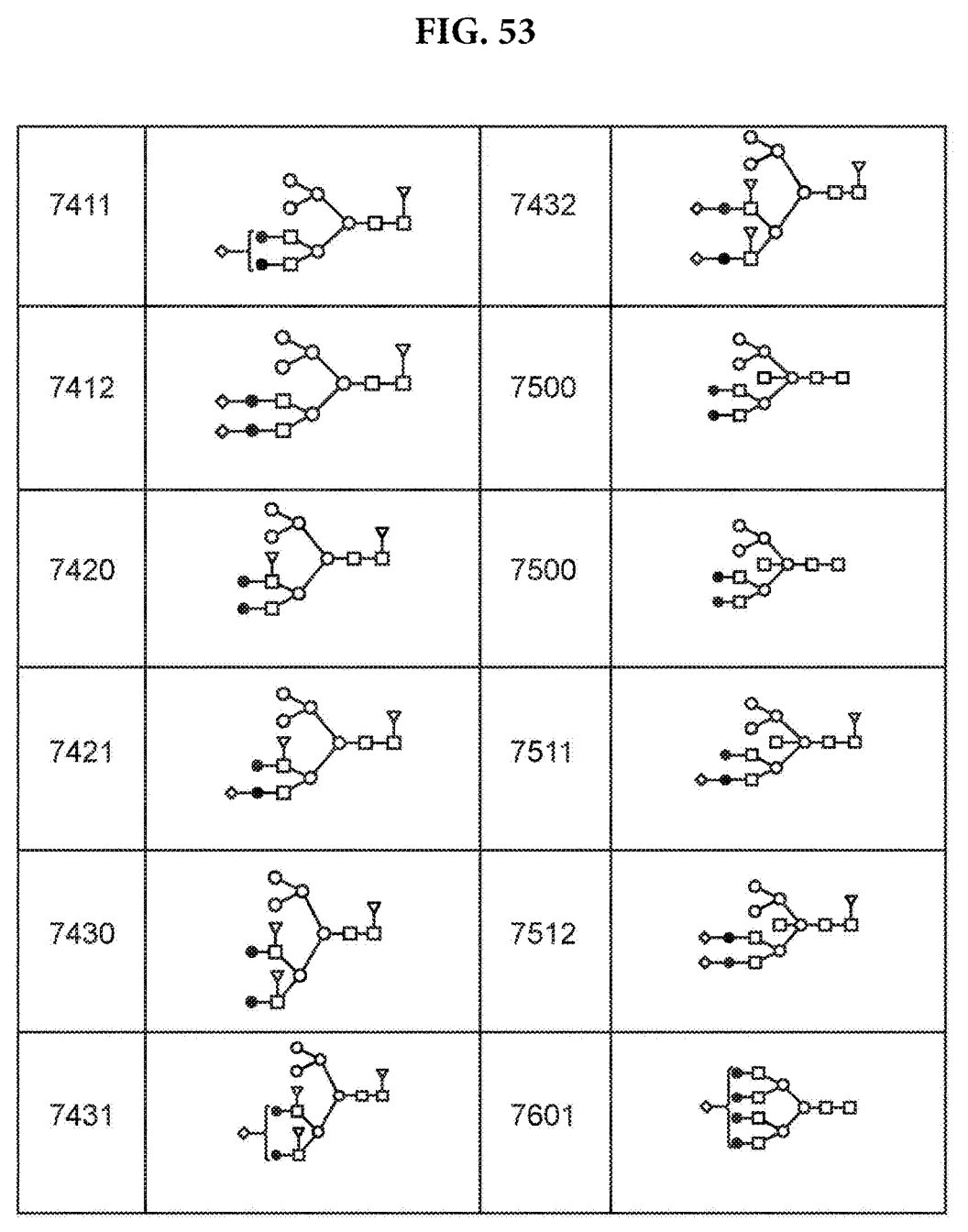

| 7411 | | 7432 | |
|------|------|------|------|
| 7412 | | 7500 | |
| 7420 | | 7500 | |
| 7421 | | 7511 | |
| 7430 | | 7512 | |
| 7431 | | 7601 | |

FIG. 54

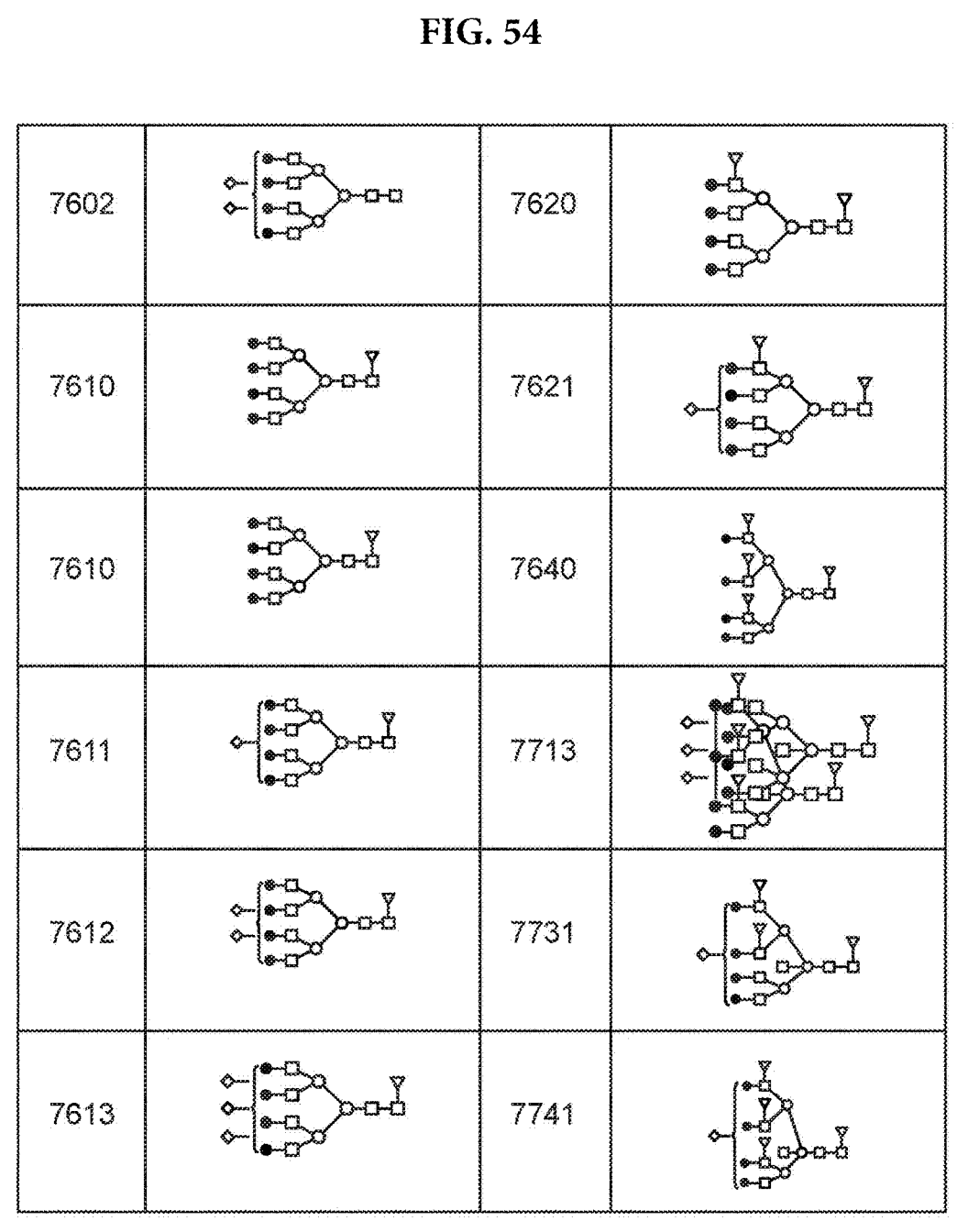

| | | | |
|---|---|---|---|
| 7602 | | 7620 | |
| 7610 | | 7621 | |
| 7610 | | 7640 | |
| 7611 | | 7713 | |
| 7612 | | 7731 | |
| 7613 | | 7741 | |

FIG. 55

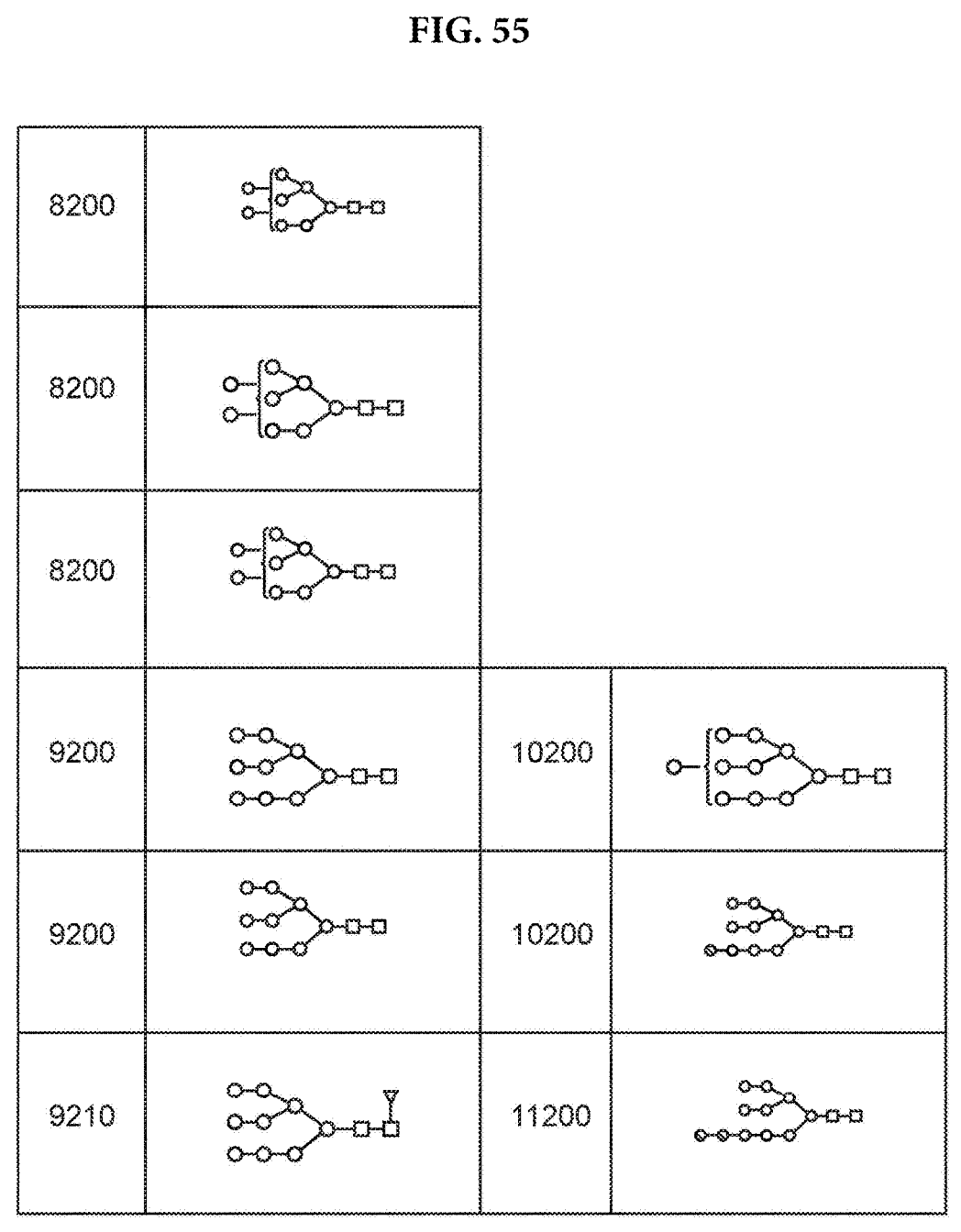

BIOMARKERS FOR CLEAR CELL RENAL CELL CARCINOMA

CROSS-REFERENCE TO RELATED APPLICATIONS

This application is a national stage application under 35 U.S.C. § 371 of International Application No. PCT/US2021/022071, filed internationally on Mar. 12, 2021, which claims priority to, and the benefit of, U.S. Provisional Application No. 62/989,510, filed on Mar. 13, 2020, the contents of each of which are hereby incorporated by reference herein in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 166532000600SEQLIST.txt, date recorded: Sep. 8, 2022, size: 10,941 bytes).

FIELD

The instant disclosure is directed to glycoproteomic biomarkers including, but not limited to, glycans, peptides, and glycopeptides, as well as to methods of using these biomarkers with mass spectroscopy and in clinical applications.

BACKGROUND

Protein glycosylation and other post-translational modifications are crucial to human growth and development. Altered protein glycosylation accompanies several diseases. Certain diseases, such as cancer, and disease states are characterized by changes in glycosylation. See, e.g., Dube, D. H.; and Bertozzi, C. R. Glycans in Cancer and Inflammation—Potential for Therapeutics and Diagnostics. Nature Rev. Drug Disc. 2005, 4, 477-88, the entire contents of which are herein incorporated by reference in its entirety for all purposes. Identifying altered glycosylation at early disease stages provides opportunities for early detection, intervention and greater chance of survival in subjects affected. Currently, there are methods to identify biomarkers that can diagnose cancer and discriminate a certain type of cancer from other diseases. Certain of these methods include proteomics, peptidomics, metabolics, proteoglycomics and glycomics using mass spectrometry (MS). See, for example, WO 2019/046814 A1, the publication of International PCT Patent Application No. PCT/US2018/049256, filed Aug. 13, 2018; US20190101544A1, the publication of U.S. patent application Ser. No. 16/120,016, filed Aug. 31, 2018; WO2019079639A1, the publication of International PCT Patent Application No. PCT/US2018/056574, filed Oct. 18, 2018; also International Patent Application No. PCT/US2020/016286, filed Jan. 31, 2020, the entire contents of each of which are herein incorporated by reference in its entirety for all purposes.

Clinically relevant, non-invasive assays for diagnosing clear cell renal cell carcinoma (ccRCC), or monitoring the prognosis of patients having ccRCC, based on glycosylation changes in a sample from that patient are still needed. In particular, there is limited data on the utilization of post-translational modifications of peptides as biomarkers for ccRCC. For example, there are currently no known tests for accurately assessing the prognosis of a patient diagnosed with ccRCC.

Mass spectroscopy (MS) offers sensitive and precise measurement of cancer-specific biomarkers including glycopeptides. See, for example, Ruhaak, L. R., et al., Protein-Specific Differential Glycosylation of Immunoglobulins in Serum of Ovarian Cancer Patients DOI: 10.1021/acs.jproteome.5b01071; J. Proteome Res., 2016, 15, 1002-1010 (2016); also Miyamoto, S., et al, Multiple Reaction Monitoring for the Quantitation of Serum Protein Glycosylation Profiles: Application to Ovarian Cancer, DOI: 10.1021/acs.jproteome.7b00541, J. Proteome Res. 2018, 17, 222-233 (2017), the entire contents of each of which are herein incorporated by reference in their entirety for all purposes. However, using MS to diagnose ccRCC or monitor prognosis has not been demonstrated to date in a clinically relevant manner.

Although protein glycosylation provides useful information about cancer and other diseases, one drawback of certain methods is the inability to trace the glycan back to the protein site of origin. To gain more knowledge about cancer biology and an early detection of cancer, it is important not only to identify the glycan, but also its site of attachment within the protein. Glycoprotein analysis is challenging in general due to several reasons. For example, a single glycan composition in a peptide may contain a large number of isomeric structures because of different glycosidic linkages, branching and many monosaccharides having the same mass. Further, the presence of multiple glycans that share the same peptide backbone causes the MS signal to split into various glycoforms, lowering their individual abundances compared to the peptides that are not glycosylated. Therefore, it has been challenging to identify glycans and their peptides from tandem MS data. It is also challenging to obtain comprehensive fragmentation for both the glycan and the peptide as they have different fragmentation efficiencies.

What is needed are new biomarkers and new methods of using MS to diagnose disease states such as ccRCC using these biomarkers. Set forth herein are such biomarkers comprising glycans, peptides, and glycopeptides, as well as fragments thereof, and methods of using the biomarkers with MS to determine the prognosis of patients having ccRCC.

SEQUENCE LISTING

The instant application contains a Sequence Listing which has been submitted electronically in ASCII format and is hereby incorporated by reference inits entirety. Said ASCII Copy, created on Mar. 12, 2021, is named 58370-707-601-SL.txt and is 11,268 bytes in size.

SUMMARY

Set forth herein is a method of detecting one or more multiple-reaction-monitoring (MRM) transitions, wherein the method includes obtaining, or having obtained, a biological sample from a patient, wherein the biological sample comprises one or more glycans, glycopeptides, or glycoproteins; digesting and/or fragmenting a glycopeptide and/or glycopeptide in the sample; and detecting an MRM transition selected from the group consisting of transitions 1-39.

Also set forth herein is a method for classifying a biological sample, wherein the method includes obtaining a biological sample from a patient, wherein the biological sample comprises one or more glycopeptides and/or glyco-proteins; digesting and/or fragmenting one or more glyco-peptides and/or glycoproteins; detecting and quantifying at least one or more multiple-reaction-monitoring (MRM) transitions selected from the group consisting of transitions 1-39; and inputting the quantification into a trained model to generate an output probability; determining if the output probability is above or below a threshold for a classification; and classifying the biological sample based on whether the output probability is above or below the threshold for a classification.

Also set forth herein is a method for monitoring, treating, or both monitoring and treating a patient having ccRCC; wherein the method includes obtaining, or having obtained, a biological sample from the patient, wherein the biological sample comprises one or more glycopeptides and/or glyco-proteins; digesting and/or fragmenting, or having digested or having fragmented, one or more glycopeptides and/or gly-coproteins; and detecting and quantifying one or more multiple-reaction-monitoring (MRM) transitions selected from the group consisting of transitions 1-39; inputting the quantification into a trained model to generate an output probability; determining if the output probability is above or below a threshold for a classification; and classifying the patient based on whether the output probability is above or below a threshold for a classification, wherein the classifi-cation is selected from the group consisting of: (A) a patient in need of a chemotherapeutic agent; (B) a patient in need of a immunotherapeutic agent; (C) a patient in need of hor-mone therapy; (D) a patient in need of a targeted therapeutic agent; (E) a patient in need of radiation therapy (F) a patient in need of surgery; (G) a patient in need of neoadjuvant therapy; (H) a patient in need of chemotherapeutic agent, immunotherapeutic agent, hormone therapy, targeted thera-peutic agent, neoadjuvant therapy, radiation therapy, or a combination thereof, before surgery; (I) a patient in need of chemotherapeutic agent, immunotherapeutic agent, hor-mone therapy, targeted therapeutic agent, neoadjuvant therapy, radiation therapy, or a combination thereof, after surgery; (J) or a combination thereof, administering a thera-peutically effective amount of a therapeutic agent to the patient: wherein the therapeutic agent is selected from chemotherapy if classification A or J is determined; wherein the therapeutic agent is selected from immunotherapy if classification B or J is determined; or wherein the therapeu-tic agent is selected from hormone therapy if classification C or J is determined; or wherein the therapeutic intervention is selected from radiation therapy if classification E or J is determined; or wherein the therapeutic agent is selected from targeted therapy if classification D or J is determined wherein the therapeutic agent is selected from neoadjuvant therapy if classification G or J is determined; wherein the therapeutic agent is selected from chemotherapeutic agent, immunotherapeutic agent, hormone therapy, targeted thera-peutic agent, neoadjuvant therapy, radiation therapy, or a combination thereof if classification H or J is determined; and wherein the therapeutic agent is selected from chemo-therapeutic agent, immunotherapeutic agent, hormone therapy, targeted therapeutic agent, neoadjuvant therapy, radiation therapy or a combination thereof if classification I or J is determined.

Also set forth herein is a method for monitoring the disease progression in a patient having ccRCC; wherein the method includes obtaining, or having obtained, a biological sample from the patient; performing mass spectroscopy of the biological sample using MRM-MS with a QQQ and/or qTOF spectrometer to detect and quantify one or more glycopeptides consisting essentially of an amino acid sequence selected from the group consisting of SEQ ID NOs: 1-39; or to detect one or more MRM transitions selected from transitions 1-39; inputting the quantification of the detected glycopeptides or the MRM transitions into a trained model to generate an output probability, determining if the output probability is above or below a threshold for a classification; and identifying a prognosis for the patient based on whether the output probability is above or below a threshold for a classification; and diagnosing the patient as having ccRCC based on the diagnostic classification.

BRIEF DESCRIPTION OF THE DRAWINGS

FIGS. 42-55 illustrate glycan chemical structures, using the Symbol Nomenclature for Glycans (SNFG) system. Each glycan structure is associated with a glycan reference code number.

DETAILED DESCRIPTION

I. General

Figure 1:
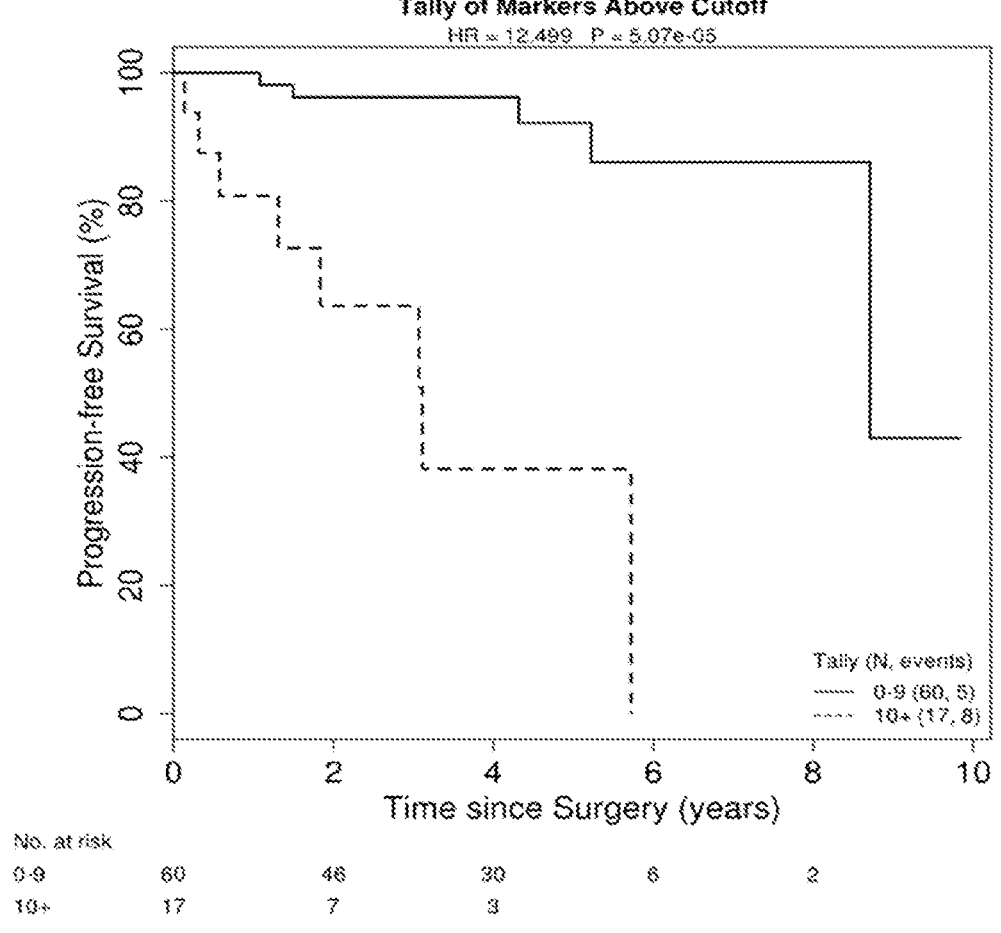
FIG. 1 shows a Kaplan-Meier plot for glycopeptides 1-39 set forth herein for a Tally of Markers Above a Cutoff.

Set forth herein are biomarkers and methods for site-specific glycoprotein analysis to obtain crucial and detailed information about protein glycosylation patterns that pro-vide precise quantitative information about the glycosy-lation site heterogeneity in diseased cells, tissues or bio-fluids compared with the non-diseased ones. In some examples, the methods set forth herein are useful for iden-tifying disease biomarkers, particularly for diseases such as ccRCC. In some examples, the methods set forth herein are useful for monitoring the prognosis of patients having diseases such as ccRCC.

II. Definitions

As used herein, the singular forms "a," "an" and "the" include plural referents unless the context clearly dictates otherwise.

As used herein, the phrase "biological sample," refers to a sample derived from, obtained by, generated from, pro-vided from, take from, or removed from an organism; or from fluid or tissue from the organism. Biological samples include, but are not limited to synovial fluid, whole blood, blood serum, blood plasma, urine, sputum, tissue, saliva, tears, spinal fluid, tissue section(s) obtained by biopsy or during surgery; cell(s) that are placed in or adapted to tissue culture; sweat, mucous, fecal material, gastric fluid, abdomi-nal fluid, amniotic fluid, cyst fluid, peritoneal fluid, pancre-atic juice, breast milk, lung lavage, marrow, gastric acid, bile, semen, pus, aqueous humor, transudate, and the like including derivatives, portions and combinations of the foregoing. In some examples, biological samples include, but are not limited, to blood and/or plasma. In some examples, biological samples include, but are not limited, to urine or stool. Biological samples include, but are not limited, to saliva. Biological samples include, but are not limited, to tissue dissections and tissue biopsies. Biological samples include, but are not limited, any derivative or fraction of the aforementioned biological samples.

As used herein, the term "glycan" refers to the carbohydrate residue of a glycoconjugate, such as the carbohydrate portion of a glycopeptide, glycoprotein, glycolipid or proteoglycan.

As used herein, the term "glycoform" refers to a unique primary, secondary, tertiary and quaternary structure of a protein with an attached glycan of a specific structure.

As used herein, the term "glycopeptide," refers to a peptide having at least one glycan residue bonded thereto.

As used herein, the term "glycoprotein," refers to a protein having at least one glycan residue bonded thereto. In some examples, a glycoprotein is a protein with at least one oligosaccharide chain covalently bonded thereto. Examples of glycoproteins, include but are not limited to apolipoprotein C-III (APOC3), alpha-1-anti chymotrypsin (AACT), afamin (AFAM), alpha-l-acid glycoprotein 1 & 2 (AGP12), apolipoprotein B-100 (APOB), apolipoprotein D (APOD), complement Cls subcomponent (CIS), calpain-3 (CAN3), clusterin (CLUS), complement component C8AChain (C08A), alpha-2-HS-glycoprotein (FETUA), haptoglobin (HPT), immunoglobulin heavy constant gamma 1 (IgGl), immunoglobulin J chain (IgJ), plasma kallikrein (KLKB1), serum paraoxonase/arylesterase 1 (PON1), prothrombin (THRB), serotransferrin (TREE), protein unc-13 homologA (UNI 3 A), and zinc-alpha-2-gly coprotein (ZA2G). A glycopeptide, as used herein, refers to a fragment of a glycoprotein, unless specified otherwise to the contrary.

As used herein, the phrase "glycosylated peptides," refers to a peptide bonded to a glycan residue.

As used herein, the phrase "glycopeptide fragment" or "glycosylated peptide fragment" refers to a glycosylated peptide (or glycopeptide) having an amino acid sequence that is the same as part (but not all) of the amino acid sequence of the glycosylated protein from which the glycosylated peptide is obtained by digestion, e.g., with one or more protease(s) or by fragmentation, e.g., ion fragmentation within a MRM-MS instrument. MRM refers to multiple-reaction-monitoring.

As used herein, the phrase "multiple reaction monitoring mass spectrometry (MRM-MS)," refers to a highly sensitive and selective method for the targeted quantification of glycans and peptides in biological samples. Unlike traditional mass spectrometry, MRM-MS is highly selective (targeted), allowing researchers to fine tune an instrument to specifically look for certain peptide fragments of interest. MRM allows for greater sensitivity, specificity, speed and quantitation of peptides fragments of interest, such as a potential biomarker. MRM-MS involves using one or more of a triple quadrupole (QQQ) mass spectrometer or a quadrupole time-of-flight (qTOF) mass spectrometer.

As used herein, the phrase "digesting a glycopeptide," refers to a biological process that employs enzymes to break specific amino acid peptide bonds. For example, digesting a glycopeptide includes contacting a glycopeptide with a digesting enzyme, e.g., trypsin, to produce fragments of the glycopeptide. In some examples, a protease enzyme is used to digest a glycopeptide. The term "protease" refers to an enzyme that performs proteolysis or breakdown of large peptides into smaller polypeptides or individual amino acids. Examples of a protease include, but are not limited to, one or more of a serine protease, threonine protease, cysteine protease, aspartate protease, glutamic acid protease, metalloprotease, asparagine peptide lyase, and any combinations of the foregoing.

As used herein, the phrase "fragmenting a glycopeptide," refers to the ion fragmentation process which occurs in an MRM-MS instrument. Fragmenting may produce various fragments having the same mass but varying with respect to their charge.

As used herein, the term "subject," refers to a mammal unless stated otherwise to the contrary. "Subject" can also include any vertebrate or multicellular organism. The non-limiting examples of a mammal include a human, non-human primate, mouse, rat, dog, cat, horse, or cow, and the like. Mammals other than humans can be advantageously used as subjects that represent animal models of disease, pre-disease, or a pre-disease condition. A subject can be male or female. A subject can be one who has been previously identified as having a disease or a condition, and optionally has already undergone, or is undergoing, a therapeutic intervention for the disease or condition. Alternatively, a subject can also be one who has not been previously diagnosed as having a disease or a condition. For example, a subject can be one who exhibits one or more risk factors for a disease or a condition, or a subject who does not exhibit disease risk factors, or a subject who is asymptomatic for a disease or a condition. A subject can also be one who is suffering from or at risk of developing a disease or a condition. A subject can also be one who is suffering from a disease or a condition and is undergoing treatment for that disease or condition.

As used herein, the term "patient" refers to a mammalian subject. The mammal can be a human, or an animal including, but not limited to an equine, porcine, canine, feline, ungulate, and primate animal. In one embodiment, the individual is a human. The methods and uses described herein are useful for both medical and veterinary uses. A "patient" is a human subject unless specified to the contrary.

As used herein, "peptide," is meant to include glycopeptides unless stated otherwise.

As used herein, the phrase "multiple-reaction-monitoring (MRM) transition," refers to the mass to charge (m/z) peaks or signals observed when a glycopeptide, or a fragment thereof, is detected by MRM-MS. The MRM transition is detected as the transition of the precursor and product ion.

As used herein, the phrase "detecting a multiple-reaction-monitoring (MRM) transition," refers to the process in which a mass spectrometer analyzes a sample using tandem mass spectrometer ion fragmentation methods and identifies the mass to charge ratio for ion fragments in a sample. The absolute values of these identified mass to charge ratios are referred to as transitions. In the context of the methods set forth herein, the mass to charge ratio transitions are the values indicative of glycan, peptide or glycopeptide ion fragments. For some glycopeptides set forth herein, there is a single transition peak or signal. For some other glycopeptides set forth herein, there is more than one transition peak or signal. Background information on MRM mass spectrometry can be found in Introduction to Mass Spectrometry: Instrumentation, Applications, and Strategies for Data Interpretation, 4th Edition, J. Throck Watson, O. David Sparkman, ISBN: 978-0-470-51634-8, November 2007, the entire contents of which are here incorporated by reference in its entirety for all purposes.

As used herein, the phrase "detecting a multiple-reaction-monitoring (MRM) transition indicative of a glycopeptide," refers to an MS process in which an MRM-MS transition is detected and then compared to a calculated mass to charge ratio (m/z) of a glycopeptide, or fragment thereof, in order to identify the glycopeptide. In some examples, herein, a single transition may be indicative of two more glycopeptides, if those glycopeptides have identical MRM-MS fragmentation patterns. A transition peak or signal includes, but is not limited to, those transitions set forth herein which are associated with a glycopeptide consisting essentially of an amino acid sequence selected from SEQ ID NOs:1-39, and combinations thereof, according to Tables 1-7, e.g., Table 1, Table 2, Table 3, Table 4, Table 5, Table 6, Table 7, or a combination thereof. A transition peak or signal includes, but is not limited to, those transitions set forth herein which are associated with a glycopeptide consisting of an amino acid sequence selected from SEQ ID NOs:1-39, and combinations thereof, according to Tables 1-7, e.g., Table 1, Table 2, Table 3, Table 4, Table 5, Table 6, Table 7, or a combination thereof.

As used herein, the term "reference value" refers to a value obtained from a population of individual(s) whose disease state is known. The reference value may be in n-dimensional feature space and may be defined by a maximum-margin hyperplane. A reference value can be determined for any particular population, subpopulation, or group of individuals according to standard methods well known to those of skill in the art.

As used herein, the term "population of individuals" means one or more individuals. In one embodiment, the population of individuals consists of one individual. In one embodiment, the population of individuals comprises multiple individuals. As used herein, the term "multiple" means at least 2 (such as at least 4, 6, 8, 10, 12, 14, 16, 18, 20, 22, 24, 26, 28, or 30) individuals. In one embodiment, the population of individuals comprises at least 10 individuals.

As used herein, the term "treatment" or "treating" means any treatment of a disease or condition in a subject, such as a mammal, including: 1) preventing or protecting against the disease or condition, that is, causing the clinical symptoms not to develop; 2) inhibiting the disease or condition, that is, arresting or suppressing the development of clinical symptoms; and/or 3) relieving the disease or condition that is, causing the regression of clinical symptoms. Treating may include administering therapeutic agents to a subject in need thereof.

As used herein, the phrase "stage of disease" refers to the stages of cancer progression referred to as Stage I, II, III, or IV. Stage of disease indicates if metastasis has occurred in the subject.

Herein, glycans are illustrated in FIGS. 42-55 using the Symbol Nomenclature for Glycans (SNFG) for illustrating glycans. An explanation of this illustration system is available on the internet at www.ncbi.nlm.nih.gov/glycans/snfg.html, the entire contents of which are herein incorporated by reference in its entirety for all purposes. Symbol Nomenclature for Graphical Representation of Glycans as published in Glycobiology 25: 1323-1324, 2015, which is available on the internet at doi.org/10.1093/glycob/cwv091. Additional information showing illustrations of the SNFG system are. Within this system, the term, Hex i: is interpreted as follows: i indicates the number of green circles (mannose) and the number of yellow circles (galactose). The term, HexNAC_j, uses j to indicate the number of blue squares (GlcNAC's). The term Fuc_d, uses d to indicate the number of red triangles (fucose). The term Neu5AC_1, uses 1 to indicate the number of purple diamonds (sialic acid). The glycan reference codes used herein combine these i, j, d, and 1 terms to make a composite 4-5 number glycan reference code, e.g., 5300 or 5320. See, for example, FIGS. 1-14 in International PCT Patent Application No. PCT/US2020/

016286, filed Jan. 31, 2020, the entire contents of which are herein incorporated by reference in its entirety for all purposes.

III. Biomarkers

Set forth herein are biomarkers. These biomarkers are useful for a variety of applications, including, but not limited to, diagnosing diseases and conditions. For example, certain biomarkers set forth herein, or combinations thereof, are useful for diagnosing ccRCC. In some other examples, certain biomarkers set forth herein, or combinations thereof, are useful for diagnosing and screening patients having ccRCC. In some other examples, certain biomarkers set forth herein, or combinations thereof, are useful for monitoring the prognosis of patients having ccRCC. In some examples, the biomarkers set forth herein, or combinations thereof, are useful for classifying a patient having ccRCC so that the patient receives the appropriate medical treatment. In some other examples, the biomarkers set forth herein, or combinations thereof, are useful for treating or ameliorating a disease or condition in a patient by, for example, identifying a therapeutic agent with which to treat a patient. In some other examples, the biomarkers set forth herein, or combinations thereof, are useful for determining a prognosis of treatment for a patient or a likelihood of success or survivability for a treatment regimen.

TABLE 1

| Glycopeptides with Unique Glycosylation Site and Residue | | | |
|---|---|---|---|
| No. | Glycosyl-ation Site | Glycan | Sequence |
| 1 | 271 | 7603 | YTGNASALFILPDQDK |
| 2 | 402-MC | 5402 | YAEDKFNETTEK |
| 3 | 72 | 7614 | SVQEIQATFFYFTPNKTEDTIFLR |
| 4 | 3411 | 5401 | FVEGSHNSTVSLTTK |
| 5 | 74 | 1111 | FSEFWDLDPEVRPTSAVAA |
| 6 | 74 | 1300 | FSEFWDLDPEVRPTSAVAA |
| 7 | 74 | 2110 | FSEFWDLDPEVRPTSAVAA |
| 8 | 74-Aoff | 1102 | FSEFWDLDPEVRPTSAVA |
| 9 | 98 | 5402 | ADGTVNQIEGEATPVNLTEPAK |
| 10 | 98 | 5410 | ADGTVNQIEGEATPVNLTEPAK |
| 11 | 98 | 6510 | ADGTVNQIEGEATPVNLTEPAK |
| 12 | 98 | 6530 | ADGTVNQIEGEATPVNLTEPAK |
| 13 | 98 | 9800 | ADGTVNQIEGEATPVNLTEPAK |
| 14 | 135 | 5421 | TELFSSSCPGGIMLNETGQGYQR |
| 15 | 135 | 8500 | TELFSSSCPGGIMLNETGQGYQR |
| 16 | 174 | 5402 | NCGVNCSGDVFTALIGEIASPNYPKPYPENSR |
| 17 | 366 | 6503 | NPWGQVEWNGSWSDR |

TABLE 1-continued

Glycopeptides with Unique Glycosylation Site and Residue

| No. | Glycosylation Site | Glycan | Sequence |
|---|---|---|---|
| 18 | 366 | 6513 | NPWGQVEWNGSWSDR |
| 19 | 291 | 5400 | HNSTGCLR |
| 20 | 291 | 6503 | HNSTGCLR |
| 21 | 437 | 5402 | GGSSGWSGGLAQNR |
| 22 | 156 | 5402 | VCQDCPLLAPLNDTR |
| 23 | 176 | 6503 | AALAAFNAQNNGSNFQLEEISR |
| 24 | 176 | 6513 | AALAAFNAQNNGSNFQLEEISR |
| 25 | 241 | 6513 | VVLHPNYSQVDIGLIK |
| 26 | 297 | 5411 | EEQYNSTYR |
| 27 | 71 | 5411 | ENISDPTSPLR |
| 28 | 494 | 5402 | LQAPLNYTEFQKPICLPSK |
| 29 | 494 | 6503 | LQAPLNYTEFQKPICLPSK |
| 30 | 324 | 5420 | VTQVYAENGTVLQGSTVASVYK |
| 31 | 324 | 6501 | VTQVYAENGTVLQGSTVASVYK |
| 32 | 324 | 6502 | VTQVYAENGTVLQGSTVASVYK |
| 33 | 121 | 5401 | GHVNITR |
| 34 | 121 | 5402 | GHVNITR |
| 35 | 630 | 5400 | QQQHLFGSNVTDCSGNFCLFR |
| 36 | 630 | 6502 | QQQHLFGSNVTDCSGNFCLFR |
| 37 | 1005 | 5431 | ACLNSTYEYIFNNCHELYSR |
| 39 | 1005 | 7420 | ACLNSTYEYIFNNCHELYSR |
| 39 | 112 | 5412 | DIVEYYNDSNGSHVLQGR |

In some examples, a sample from a patient is analyzed by MS and the results are used to determine the presence, absolute amount, and/or relative amount of a glycopeptide consisting of an amino acid sequence selected from SEQ ID NOs:1-39 in the sample. In some examples, a sample from a patient is analyzed by MS and the results are used to determine the presence, absolute amount, and/or relative amount of a glycopeptide consisting essentially of an amino acid sequence selected from SEQ ID NOs:1-39 in the sample. In some examples, a sample from a patient is analyzed by MS and the results are used to determine the presence, absolute amount, and/or relative amount of a glycopeptide consisting of, or consisting essentially of, an amino acid sequence selected from SEQ ID NOs: 1-39 in the sample. In some examples, a sample from a patient is analyzed by MS and the results are used to determine the presence, absolute amount, and/or relative amount of a glycopeptide consisting of, or consisting essentially of, an amino acid sequence selected from SEQ ID NOs: 1-39 in the sample. In some examples, a sample from a patient is analyzed by MS and the results are used to determine the presence, absolute amount, and/or relative amount of a glycopeptide consisting of an amino acid sequence selected from SEQ ID NOs: 15, 19, 21, 27, and 33 in the sample. In some examples, a sample from a patient is analyzed by MS and the results are used to determine the presence, absolute amount, and/or relative amount of a glycopeptide consisting essentially of an amino acid sequence selected from SEQ ID NOs: 15, 19, 21, 27, and 33 in the sample. In some examples, a sample from a patient is analyzed by MS and the results are used to determine the presence, absolute amount, and/or relative amount of a glycopeptide consisting of, or consisting essentially of, an amino acid sequence selected from SEQ ID NOs: 15, 19, 21, 27, and 33 in the sample. In some examples, a sample from a patient is analyzed by MS and the results are used to determine the presence, absolute amount, and/or relative amount of a glycopeptide consisting of, or consisting essentially of, an amino acid sequence selected from SEQ ID NOs: 15, 19, 21, 27, and 33 in the sample. In some examples, as described below, the presence, absolute amount, and/or relative amount of a glycopeptide is determined by analyzing the MS results. In some examples, the MS results are analyzed using machine learning a. O-Glycosylation In some examples, the glycopeptides set forth herein include O-glycosylated peptides. These peptides include glycopeptides in which a glycan is bonded to the peptide through an oxygen atom of an amino acid. Typically, the amino acid to which the glycan is bonded is threonine (T) or serine (S). In some examples, the amino acid to which the glycan is bonded is threonine (T). In some examples, the amino acid to which the glycan is bonded is serine (S).

In certain examples, the O-glycosylated peptides include those peptides from the group selected from Apolipoprotein C-III (APOC3).

b. N-Glycosylation

In some examples, the glycopeptides set forth herein include N-glycosylated peptides. These peptides include glycopeptides in which a glycan is bonded to the peptide through a nitrogen atom of an amino acid. Typically, the amino acid to which the glycan is bonded is asparagine (N) or arginine (R). In some examples, the amino acid to which the glycan is bonded is asparagine (N). In some examples, the amino acid to which the glycan is bonded is arginine (R).

In certain examples, the N-glycosylated peptides include members selected from the group consisting Alpha-1-anti chymotrypsin (AACT), Afamin (AFAM), Alpha-l-acid glycoprotein 1 & 2 (AGP 12), Apolipoprotein B-100 (APOB), Apolipoprotein D (APOD), Complement Cls subcomponent (CIS), Calpain-3 (CAN3), Clusterin (CLUS), ComplementComponentC8AChain (C08A), Alpha-2-HS-glycoprotein (FETUA), Haptoglobin (HPT), Immunoglobulin heavy constant gamma 1 (IgGl); Immunoglobulin J chain (IgJ), Plasma Kallikrein (KLKB1), Serum paraoxonase/arylesterase 1 (PON1), Prothrombin (THRB), Serotransferrin (TRFE), Protein unc-13 Homolog A (UN 13 A); Zinc-alpha-2-glycoprotein (ZA2G), and combinations thereof.

In some examples, set forth herein is a glycopeptide consisting of an amino acid sequence selected from the group consisting of SEQ ID NOs: 1-39, and combinations thereof.

In some examples, set forth herein is a glycopeptide consisting essentially of an amino acid sequence selected from the group consisting of SEQ ID NOs: 1-39, and combinations thereof.

In certain examples, the glycopeptide consists essentially of an amino acid sequence selected from SEQ ID NO:1. In some examples, the glycopeptide comprises glycan 7603, wherein the glycan(s) are bonded to residue 271. In some examples, the glycopeptide is AACT-GP005 271 7603. Herein AACT refers to Alpha-1-anti chymotrypsin.

In certain examples, the glycopeptide consists essentially of an amino acid sequence selected from SEQ ID NO:2. In some examples, the glycopeptide comprises glycan 5402 at residue 402-MC. In some examples, the glycopeptide is AFAM-GP006_402_5402. Herein AFAM refers to Afamin.

Herein, "MC" refers to a missed cleavage of a trypsin digestion. A missed cleavage peptide includes the amino acid sequence selected from SEQ ID NO:2 but also includes additional residues which were not cleaved by way of trypsin digestion.

In certain examples, the glycopeptide consists essentially of an amino acid sequence selected from SEQ ID NO:3. In some examples, the glycopeptide comprises glycan 7614 at residue 72-MC. In some examples, the glycopeptide is AGP12-GP007&008_72MC_7614. Herein AGP12 refers to Alpha-1-acid glycoprotein 1&2.

In certain examples, the glycopeptide consists essentially of an amino acid sequence selected from SEQ ID NO:4. In some examples, the glycopeptide comprises glycan 5401 at residue 3411. In some examples, the glycopeptide is APOB-GP013 3411 5401. Herein APOB refers to Apolipoprotein B-100.

In certain examples, the glycopeptide consists essentially of an amino acid sequence selected from SEQ ID NO:5. In some examples, the glycopeptide comprises glycan 1111 at residue 74. In some examples, the glycopeptide is APOC3-GP012_74_1111. Herein, APOC3 refers to Apolipoprotein C-III.

In certain examples, the glycopeptide consists essentially of an amino acid sequence selected from SEQ ID NO:6. In some examples, the glycopeptide comprises glycan 1300 at residue 74. In some examples, the glycopeptide is APOC3-GP012_74_1300.

In certain examples, the glycopeptide consists essentially of an amino acid sequence selected from SEQ ID NO:7. In some examples, the glycopeptide comprises glycan 2110 at residue 74. In some examples, the glycopeptide is APOC3-GP012_74_2110.

In certain examples, the glycopeptide consists essentially of an amino acid sequence selected from SEQ ID NO:8. In some examples, the glycopeptide comprises glycan 1102 at residue 74Aoff In some examples, the glycopeptide is APOC3-GP012_74Aoff_1 102. Herein, "Aoff" indicates an aniline modification on the c-terminus of the peptide.

In certain examples, the glycopeptide consists essentially of an amino acid sequence selected from SEQ ID NO:9. In some examples, the glycopeptide comprises glycans 5402 or 5421, or both, at residue 98. In some examples, the glycopeptide is APOD-GP014_98_5402/5421. Herein APOD refers to Apolipoprotein D.

In certain examples, the glycopeptide consists essentially of an amino acid sequence selected from SEQ ID NO: 10. In some examples, the glycopeptide comprises glycan 5410 at residue 98. In some examples, the glycopeptide is APOD-GP014_98_5410.

In certain examples, the glycopeptide consists essentially of an amino acid sequence selected from SEQ ID NO: 11. In some examples, the glycopeptide comprises glycan 6510 at residue 98. In some examples, the glycopeptide is APOD-GP014_98_6510.

In certain examples, the glycopeptide consists essentially of an amino acid sequence selected from SEQ ID NO: 12. In some examples, the glycopeptide comprises glycan 6530 at residue 98. In some examples, the glycopeptide is APOD-GP014_98_6530.

In certain examples, the glycopeptide consists essentially of an amino acid sequence selected from SEQ ID NO: 13. In some examples, the glycopeptide comprises glycan 9800 at residue 98. In some examples, the glycopeptide is APOD-GP014_98_9800.

In certain examples, the glycopeptide consists essentially of an amino acid sequence selected from SEQ ID NO: 14. In some examples, the glycopeptide comprises glycan 5421 at residue 135. In some examples, the glycopeptide is APOM-GP016_135_5421.

In certain examples, the glycopeptide consists essentially of an amino acid sequence selected from SEQ ID NO: 15. In some examples, the glycopeptide comprises glycan 8500 at residue 135. In some examples, the glycopeptide is APOM-GP016_135_8500.

In certain examples, the glycopeptide consists essentially of an amino acid sequence selected from SEQ ID NO: 16. In some examples, the glycopeptide comprises glycan 5402 at residue 174. In some examples, the glycopeptide is C1S-GPO20_174_5402. Herein CIS refers to Complement Cls subcomponent.

In certain examples, the glycopeptide consists essentially of an amino acid sequence selected from SEQ ID NO: 17. In some examples, the glycopeptide comprises glycan 6503 at residue 366. In some examples, the glycopeptide is CAN3-GP022_366_6503. Herein CAN3 refers to Calpain-3.

In certain examples, the glycopeptide consists essentially of an amino acid sequence selected from SEQ ID NO: 18. In some examples, the glycopeptide comprises glycan 6513 at residue 366. In some examples, the glycopeptide is CAN3-GP022_366_6513.

In certain examples, the glycopeptide consists essentially of an amino acid sequence selected from SEQ ID NO: 19. In some examples, the glycopeptide comprises glycan 5400 at residue 291. In some examples, the glycopeptide is CLUS-GP026_291_5400. Herein CLUS refers to Clusterin.

In certain examples, the glycopeptide consists essentially of an amino acid sequence selected from SEQ ID NO:20. In some examples, the glycopeptide comprises glycan 6503 at residue 291. In some examples, the glycopeptide is CLUS-GP026_291_6503.

In certain examples, the glycopeptide consists essentially of an amino acid sequence selected from SEQ ID NO:21. In some examples, the glycopeptide comprises glycan 5402 at residue 437. In some examples, the glycopeptide is CO8A-GP033_437_5402. Herein C08A refers to ComplementComponentC8AChain.

In certain examples, the glycopeptide consists essentially of an amino acid sequence selected from SEQ ID NO:22. In some examples, the glycopeptide comprises glycan 5402 or 5421, or both, at residue 156. In some examples, the glycopeptide is FETUA-GP036_156_5402/5421. Herein FETUA refers to Alpha-2-HS-glycoprotein.

In certain examples, the glycopeptide consists essentially of an amino acid sequence selected from SEQ ID NO:23. In some examples, the glycopeptide comprises glycan 6503 at residue 176. In some examples, the glycopeptide is FETUA-GP036_176_6503.

In certain examples, the glycopeptide consists essentially of an amino acid sequence selected from SEQ ID NO:24. In some examples, the glycopeptide comprises glycan 6513 at residue 176. In some examples, the glycopeptide is FETUA-GP036_176_6513.

In certain examples, the glycopeptide consists essentially of an amino acid sequence selected from SEQ ID NO:25. In some examples, the glycopeptide comprises glycan 6513 at residue 241. In some examples, the glycopeptide is HPT-GP044_241_6513. Herein HPT refers to Haptoglobin.

In certain examples, the glycopeptide consists essentially of an amino acid sequence selected from SEQ ID NO:26. In some examples, the glycopeptide comprises glycan 5411 at residue 297. In some examples, the glycopeptide is IgGl-GP048_297_5411. Herein IgGl refers to Immunoglobulin heavy constant gamma 1.

In certain examples, the glycopeptide consists essentially of an amino acid sequence selected from SEQ ID NO:27. In some examples, the glycopeptide comprises glycan 5411 at residue 71. In some examples, the glycopeptide is IgJ-GP052_71_5411. Herein IgJ refers to Immunoglobulin J chain.

In certain examples, the glycopeptide consists essentially of an amino acid sequence selected from SEQ ID NO:28. In some examples, the glycopeptide comprises glycan 5402 at residue 494. In some examples, the glycopeptide is KLKB1-GP056_494_5402. Herein KLKB 1 refers to Plasma Kallikrein.

In certain examples, the glycopeptide consists essentially of an amino acid sequence selected from SEQ ID NO:29. In some examples, the glycopeptide comprises glycan 6503 at residue 494. In some examples, the glycopeptide is KLKB1-GP056_494_6503.

In certain examples, the glycopeptide consists essentially of an amino acid sequence selected from SEQ ID NO:30. In some examples, the glycopeptide comprises glycan 5420 at residue 324. In some examples, the glycopeptide is PON1-GP060_324_5420. Herein PON1 refers to Serum paraoxonase/arylesterase 1.

In certain examples, the glycopeptide consists essentially of an amino acid sequence selected from SEQ ID NO:31. In some examples, the glycopeptide comprises glycan 6501 at residue 324. In some examples, the glycopeptide is PON1-GP060_324_6501.

In certain examples, the glycopeptide consists essentially of an amino acid sequence selected from SEQ ID NO:32. In some examples, the glycopeptide comprises glycan 6502 at residue 324. In some examples, the glycopeptide is PON1-GP060_324_6502.

In certain examples, the glycopeptide consists essentially of an amino acid sequence selected from SEQ ID NO:33. In some examples, the glycopeptide comprises glycan 5420 or 5401, or both, at residue 121. In some examples, the glycopeptide is THRB-GP063_121_5420/5401. Herein THRB refers to Prothrombin.

In certain examples, the glycopeptide consists essentially of an amino acid sequence selected from SEQ ID NO:34. In some examples, the glycopeptide comprises glycan 5421 or 5402, or both, at residue 121. In some examples, the glycopeptide is THRB-GP063_121_5421/5402.

In certain examples, the glycopeptide consists essentially of an amino acid sequence selected from SEQ ID NO:35. In some examples, the glycopeptide comprises glycan 5400 at residue 630. In some examples, the glycopeptide is TRFE-GP064_630_5400. Herein TRFE refers to Serotransferrin.

In certain examples, the glycopeptide consists essentially of an amino acid sequence selected from SEQ ID NO:36. In some examples, the glycopeptide comprises glycan 6502 at residue 630. In some examples, the glycopeptide is TRFE-GP064_630_6502.

In certain examples, the glycopeptide consists essentially of an amino acid sequence selected from SEQ ID NO:37. In some examples, the glycopeptide comprises glycan 5431 at residue 1005. In some examples, the glycopeptide is UN13A-GP066_1005_5431. Herein UNI 3 A refers to Protein unc-13HomologA.

In certain examples, the glycopeptide consists essentially of an amino acid sequence selected from SEQ ID NO:38. In some examples, the glycopeptide comprises glycan 7420 at residue 1005. In some examples, the glycopeptide is UN13A-GP066_1005_7420.

In certain examples, the glycopeptide consists essentially of an amino acid sequence selected from SEQ ID NO:39. In some examples, the glycopeptide comprises glycan 5412 at residue 112. In some examples, the glycopeptide is ZA2G-GP068_112_5412. Herein ZA2G refers to Zinc-alpha-2-glycoprotein.

In some examples, set forth herein is a glycopeptide consisting of an amino acid sequence selected from the group consisting of SEQ ID NOs: 1-39, and combinations thereof.

In some examples, set forth herein is a glycopeptide consisting essentially of an amino acid sequence selected from the group consisting of SEQ ID NOs: 1-39, and combinations thereof.

In certain examples, the glycopeptide consists of an amino acid sequence selected from SEQ ID NO:1. In some examples, the glycopeptide comprises glycan 7603, wherein the glycan(s) are bonded to residue 271. In some examples, the glycopeptide is AACT-GP005_271_7603. Herein AACT refers to Alpha-1-anti chymotrypsin.

In certain examples, the glycopeptide consists of an amino acid sequence selected from SEQ ID NO:2. In some examples, the glycopeptide comprises glycan 5402 at residue 402-MC. In some examples, the glycopeptide is AFAM-GP006_402_5402. Herein AFAM refers to Afamin.

Herein, "MC" refers to a missed cleavage of a trypsin digestion. A missed cleavage peptide includes the amino acid sequence selected from SEQ ID NO:2 but also includes additional residues which were not cleaved by way of trypsin digestion.

In certain examples, the glycopeptide consists of an amino acid sequence selected from SEQ ID NO:3. In some examples, the glycopeptide comprises glycan 7614 at residue 72-MC. In some examples, the glycopeptide is AGP12-GP007&008_72MC_7614. Herein AGP12 refers to Alpha-l-acid glycoprotein 1&2.

In certain examples, the glycopeptide consists of an amino acid sequence selected from SEQ ID NO:4. In some examples, the glycopeptide comprises glycan 5401 at residue 3411. In some examples, the glycopeptide is APOB-GP013_3411_5401. Herein APOB refers to Apolipoprotein B-100.

In certain examples, the glycopeptide consists of an amino acid sequence selected from SEQ ID NO:5. In some examples, the glycopeptide comprises glycan 1111 at residue 74. In some examples, the glycopeptide is APOC3-GP012_74_1111. Herein, APOC3 refers to Apolipoprotein C-III.

In certain examples, the glycopeptide consists of an amino acid sequence selected from SEQ ID NO:6. In some examples, the glycopeptide comprises glycan 1300 at residue 74. In some examples, the glycopeptide is APOC3-GP012_74_1300.

In certain examples, the glycopeptide consists of an amino acid sequence selected from SEQ ID NO:7. In some examples, the glycopeptide comprises glycan 2110 at residue 74. In some examples, the glycopeptide is APOC3-GPO12_74_2110.

In certain examples, the glycopeptide consists of an amino acid sequence selected from SEQ ID NO:8. In some examples, the glycopeptide comprises glycan 1102 at residue 74Aoff. In some examples, the glycopeptide is APOC3-GP012_74Aoff_1102.

In certain examples, the glycopeptide consists of an amino acid sequence selected from SEQ ID NO:9. In some examples, the glycopeptide comprises glycans 5402 or 5421, or both, at residue 98. In some examples, the glycopeptide is APOD-GP014_98_5402/5421. Herein APOD refers to Apolipoprotein D.

In certain examples, the glycopeptide consists of an amino acid sequence selected from SEQ ID NO: 10. In some examples, the glycopeptide comprises glycan 5410 at residue 98. In some examples, the glycopeptide is APOD-GP014_98_5410.

In certain examples, the glycopeptide consists of an amino acid sequence selected from SEQ ID NO: 11. In some examples, the glycopeptide comprises glycan 6510 at residue 98. In some examples, the glycopeptide is APOD-GP014_98_6510.

In certain examples, the glycopeptide consists of an amino acid sequence selected from SEQ ID NO: 12. In some examples, the glycopeptide comprises glycan 6530 at residue 98. In some examples, the glycopeptide is APOD-GP014_98_6530.

In certain examples, the glycopeptide consists of an amino acid sequence selected from SEQ ID NO: 13. In some examples, the glycopeptide comprises glycan 9800 at residue 98. In some examples, the glycopeptide is APOD-GP014_98_9800.

In certain examples, the glycopeptide consists of an amino acid sequence selected from SEQ ID NO: 14. In some examples, the glycopeptide comprises glycan 5421 at residue 135. In some examples, the glycopeptide is APOM-GP016_135_5421.

In certain examples, the glycopeptide consists of an amino acid sequence selected from SEQ ID NO: 15. In some examples, the glycopeptide comprises glycan 8500 at residue 135. In some examples, the glycopeptide is APOM-GP016_135_8500.

In certain examples, the glycopeptide consists of an amino acid sequence selected from SEQ ID NO: 16. In some examples, the glycopeptide comprises glycan 5402 at residue 174. In some examples, the glycopeptide is C1S-GPO20_174_5402. Herein CIS refers to Complement Cls subcomponent.

In certain examples, the glycopeptide consists of an amino acid sequence selected from SEQ ID NO: 17. In some examples, the glycopeptide comprises glycan 6503 at residue 366. In some examples, the glycopeptide is CAN3-GP022_366_6503. Herein CAN3 refers to Calpain-3.

In certain examples, the glycopeptide consists of an amino acid sequence selected from SEQ ID NO:18. In some examples, the glycopeptide comprises glycan 6513 at residue 366. In some examples, the glycopeptide is CAN3-GP022_366_6513.

In certain examples, the glycopeptide consists of an amino acid sequence selected from SEQ ID NO: 19. In some examples, the glycopeptide comprises glycan 5400 at residue 291. In some examples, the glycopeptide is CLUS-GP026_291_5400. Herein CLUS refers to Clusterin.

In certain examples, the glycopeptide consists of an amino acid sequence selected from SEQ ID NO:20. In some examples, the glycopeptide comprises glycan 6503 at residue 291. In some examples, the glycopeptide is CLUS-GP026_291_6503.

In certain examples, the glycopeptide consists of an amino acid sequence selected from SEQ ID NO:21. In some examples, the glycopeptide comprises glycan 5402 at residue 437. In some examples, the glycopeptide is CO8A-GP033_437_5402. Herein C08A refers to ComplementComponentC8AChain.

In certain examples, the glycopeptide consists of an amino acid sequence selected from SEQ ID NO:22. In some examples, the glycopeptide comprises glycan 5402 or 5421, or both, at residue 156. In some examples, the glycopeptide is FETUA-GP036_156_5402/5421. Herein FETUA refers to Alpha-2-HS-glycoprotein.

In certain examples, the glycopeptide consists of an amino acid sequence selected from SEQ ID NO:23. In some examples, the glycopeptide comprises glycan 6503 at residue 176. In some examples, the glycopeptide is FETUA-GP036_176_6503.

In certain examples, the glycopeptide consists of an amino acid sequence selected from SEQ ID NO:24. In some examples, the glycopeptide comprises glycan 6513 at residue 176. In some examples, the glycopeptide is FETUA-GP036_176_6513.

In certain examples, the glycopeptide consists of an amino acid sequence selected from SEQ ID NO:25. In some examples, the glycopeptide comprises glycan 6513 at residue 241. In some examples, the glycopeptide is HPT-GP044_241_6513. Herein HPT refers to Haptoglobin.

In certain examples, the glycopeptide consists of an amino acid sequence selected from SEQ ID NO:26. In some examples, the glycopeptide comprises glycan 5411 at residue 297. In some examples, the glycopeptide is IgGl-GP048_297_5411. Herein IgGl refers to Immunoglobulin heavy constant gamma 1.

In certain examples, the glycopeptide consists of an amino acid sequence selected from SEQ ID NO:27. In some examples, the glycopeptide comprises glycan 5411 at residue 71. In some examples, the glycopeptide is IgJ-GP052_71_5411. Herein IgJ refers to Immunoglobulin J chain.

In certain examples, the glycopeptide consists of an amino acid sequence selected from SEQ ID NO:28. In some examples, the glycopeptide comprises glycan 5402 at residue 494. In some examples, the glycopeptide is KLKB1-GP056_494_5402. Herein KLKB1 refers to Plasma Kallikrein.

In certain examples, the glycopeptide consists of an amino acid sequence selected from SEQ ID NO:29. In some examples, the glycopeptide comprises glycan 6503 at residue 494. In some examples, the glycopeptide is KLKB1-GP056_494_6503.

In certain examples, the glycopeptide consists of an amino acid sequence selected from SEQ ID NO:30. In some examples, the glycopeptide comprises glycan 5420 at residue 324. In some examples, the glycopeptide is PON1-GP060_324_5420. Herein PON1 refers to Serum paraoxonase/arylesterase 1.

In certain examples, the glycopeptide consists of an amino acid sequence selected from SEQ ID NO:31. In some examples, the glycopeptide comprises glycan 6501 at residue 324. In some examples, the glycopeptide is PON1-GP060_324_6501.

In certain examples, the glycopeptide consists of an amino acid sequence selected from SEQ ID NO:32. In some examples, the glycopeptide comprises glycan 6502 at residue 324. In some examples, the glycopeptide is PON1-GP060_324_6502.

In certain examples, the glycopeptide consists of an amino acid sequence selected from SEQ ID NO:33. In some examples, the glycopeptide comprises glycan 5420 or 5401, or both, at residue 121. In some examples, the glycopeptide is THRB-GP063_121_5420/5401. Herein THRB refers to prothrombin.

In certain examples, the glycopeptide consists of an amino acid sequence selected from SEQ ID NO:34. In some examples, the glycopeptide comprises glycan 5421 or 5402, or both, at residue 121. In some examples, the glycopeptide is THRB-GP063_121_5421/5402.

In certain examples, the glycopeptide consists of an amino acid sequence selected from SEQ ID NO:35. In some examples, the glycopeptide comprises glycan 5400 at residue 630. In some examples, the glycopeptide is TRFE-GP064_630_5400. Herein TRFE refers to serotransferrin.

In certain examples, the glycopeptide consists of an amino acid sequence selected from SEQ ID NO:36. In some examples, the glycopeptide comprises glycan 6502 at residue 630. In some examples, the glycopeptide is TRFE-GP064_630_6502.

In certain examples, the glycopeptide consists of an amino acid sequence selected from SEQ ID NO:37. In some examples, the glycopeptide comprises glycan 5431 at residue 1005. In some examples, the glycopeptide is UN13A-GP066_1005_5431. Herein UNI 3 A refers to protein unc-13 homologA.

In certain examples, the glycopeptide consists of an amino acid sequence selected from SEQ ID NO:38. In some examples, the glycopeptide comprises glycan 7420 at residue 1005. In some examples, the glycopeptide is UN13A-GP066_1005_7420.

In certain examples, the glycopeptide consists of an amino acid sequence selected from SEQ ID NO:39. In some examples, the glycopeptide comprises glycan 5412 at residue 112. In some examples, the glycopeptide is ZA2G-GP068 112 5412. Herein ZA2G refers to Zinc-alpha-2-glycoprotein.

IV. Methods of Using Biomarkers

In an example, set forth herein is a method of detecting one or more multiple-reaction-monitoring (MRM) transitions, comprising: obtaining, or having obtained, a biological sample from a patient, wherein the biological sample includes one or more glycans, glycopeptides, or glycoproteins; digesting and/or fragmenting a glycopeptide and/or glycopeptide in the sample; and detecting an MRM transition selected from the group consisting of transitions 1-39

In some examples, including any of the foregoing, the fragmenting a glycopeptide occurs after introducing the sample, or a portion thereof, into the mass spectrometer.

In some examples, including any of the foregoing, the fragmenting a glycopeptide produces a peptide or glycopeptide consisting essentially of an amino acid sequence selected from the group consisting of SEQ ID NOs: 1-39, and combinations thereof.

In some examples, including any of the foregoing, the fragmenting a glycopeptide produces a peptide or glycopeptide consisting essentially of an amino acid sequence selected from the group consisting of SEQ ID NOs: 15, 19, 21, 27, 33, and combinations thereof.

In some examples, including any of the foregoing, the MRM transition is selected from the transitions, or any combinations thereof, in any one of Tables 1-7.

In some examples, including any of the foregoing, detecting an MRM transition selected from the group consisting of transitions 1-39 includes detecting an MRM transition using a triple quadrupole (QQQ) mass spectrometer or a quadrupole time-of-flight (qTOF) mass spectrometer.

In some examples, including any of the foregoing, the one or more glycopeptides includes a peptide or glycopeptide consisting essentially of an amino acid sequence selected from the group consisting of SEQ ID NOs: 1-39, and combinations thereof.

In some examples, including any of the foregoing, the one or more glycopeptides includes a peptide or glycopeptide consisting essentially of an amino acid sequence selected from the group consisting of SEQ ID NOs: 15, 19, 21, 27, 33, and combinations thereof.

In some examples, including any of the foregoing, the methods includes detecting one or more MRM transitions indicative of one or more glycans selected from the group Consisting of glycan 3200, 3210, 3300, 3310, 3320, 3400, 3410, 3420, 3500, 3510, 3520, 3600, 3610, 3620, 3630, 3700, 3710, 3720, 3730, 3740, 4200, 4210, 4300, 4301, 4310, 4311, 4320, 4400, 4401, 4410, 4411, 4420, 4421, 4430, 4431, 4500, 4501, 4510, 4511, 4520, 4521, 4530, 4531, 4540, 4541, 4600, 4601, 4610, 4611, 4620, 4621, 4630, 4631, 4641, 4650,4700, 4701, 4710, 4711, 4720, 4730, 5200, 5210, 5300, 5301, 5310, 5311, 5320, 5400, 5401, 5402, 5410, 5411, 5412, 5420, 5421, 5430, 5431, 5432, 5500, 5501, 5502, 5510, 5511, 5512, 5520, 5521, 5522, 5530, 5531, 5541, 5600, 5601, 5602, 5610, 5611, 5612, 5620, 5621, 5631, 5650, 5700, 5701, 5702, 5710, 5711, 5712, 5720, 5721, 5730, 5731, 6200, 6210, 6300, 6301, 6310, 6311, 6320, 6400, 6401, 6402, 6410, 6411, 6412, 6420, 6421, 6432, 6500, 6501, 6502, 6503, 6510, 6511, 6512, 6513, 6520, 6521, 6522, 6530, 6531, 6532, 6540, 6541, 6600, 6601, 6602, 6603, 6610, 6611, 6612, 6613, 6620, 6621, 6622, 6623, 6630, 6631, 6632, 6640, 6641, 6642, 6652, 6700, 6701, 6711, 6721, 6703, 6713, 6710, 6711, 6712, 6713, 6720, 6721, 6730, 6731, 6740, 7200, 7210, 7400, 7401, 7410, 7411, 7412, 7420, 7421, 7430, 7431, 7432, 7500, 7501, 7510, 7511, 7512, 7600, 7601, 7602, 7603, 7604, 7610, 7611, 7612, 7613, 7614, 7620, 7621, 7622, 7623, 7632, 7640, 7700, 7701, 7702, 7703, 7710, 7711, 7712, 7713, 7714, 7720, 7721, 7722, 7730, 7731, 7732, 7740, 7741, 7751, 8200, 9200, 9210, 10200, 11200, 12200, and combinations thereof.

In some examples, including any of the foregoing, the method further includes quantifying a first glycan and quantifying a second glycan; and further comprising comparing the quantification of the first glycan with the quantification of the second glycan.

In some examples, including any of the foregoing, the method further includes associating the detected glycan with a peptide residue site, whence the glycan was bonded.

In some examples, including any of the foregoing, the method further includes normalizing the amount of glycopeptide based on the amount of a peptide or glycopeptide consisting essentially of an amino acid having a SEQ ID. No: 1-39.

In another example, set forth herein is a method for identifying a classification for a sample, the method comprising quantifying by mass spectroscopy (MS) one or more glycopeptides in a sample wherein the glycopeptides includes a glycopeptide consisting essentially of an amino acid sequence selected from the group consisting of SEQ ID NOs: 1-39, and combinations thereof, and inputting the quantification into a trained model to generate an output probability; determining if the output probability is above or below a threshold for a classification; and identifying a classification for the sample based on whether the output probability is above or below the threshold for a classification.

In some examples, including any of the foregoing, the method includes quantifying by mass spectroscopy (MS) one or more glycopeptides in a sample wherein the glycopeptides includes a glycopeptide consisting essentially of an amino acid sequence selected from the group consisting of SEQ ID NOs: 15, 19, 21, 27, and 33, and combinations thereof.

In some examples, including any of the foregoing, the sample is a biological sample from a patient or individual having a disease or condition.

In some examples, including any of the foregoing, the patient has clear cell Renal Cell Carcinoma (ccRCC).

In some examples, including any of the foregoing, the MS is MRM-MS with a QQQ and/or qTOF mass spectrometer.

In some examples, including any of the foregoing, the trained model was trained using a machine learning algorithm selected from the group consisting of a deep learning algorithm, a neural network algorithm, an artificial neural network algorithm, a supervised machine learning algorithm, a linear discriminant analysis algorithm, a quadratic discriminant analysis algorithm, a support vector machine algorithm, a linear basis function kernel support vector algorithm, a radial basis function kernel support vector algorithm, a random forest algorithm, a genetic algorithm, a nearest neighbor algorithm, k-nearest neighbors, a naive Bayes classifier algorithm, a logistic regression algorithm, or a combination thereof.

In some examples, including any of the foregoing, the classification is a stage of disease progression for ccRCC.

In some examples, including any of the foregoing, the classification is identified with greater than 80% confidence, greater than 85% confidence, greater than 90% confidence, greater than 95% confidence, or greater than 99% confidence.

In some examples, including any of the foregoing, the method further includes quantifying by MS a first glycopeptide in a sample at a first time point; quantifying by MS a second glycopeptide in a sample at a second time point; and comparing the quantification at the first time point with the quantification at the second time point.

In some examples, including any of the foregoing, the method further includes quantifying by MS a third glycopeptide in a sample at a third time point; quantifying by MS a fourth glycopeptide in a sample at a fourth time point; and comparing the quantification at the fourth time point with the quantification at the third time point.

In some examples, including any of the foregoing, the method further includes monitoring the health status of a patient by practicing the methods of claim 13 on a series of samples from the patient.

In some examples, including any of the foregoing, the method further includes monitoring the health status of a patient includes monitoring the onset and/or progression of disease in a patient having ccRCC.

In some examples, including any of the foregoing, the method further includes quantifying by MS an amino acid sequence selected from the group consisting of SEQ ID NOs: 1-39.

In some examples, including any of the foregoing, the method further includes quantifying by MS an amino acid sequence selected from the group consisting of SEQ ID NOs: 15, 19, 21, 27, and 33.

In some examples, including any of the foregoing, the method further includes quantifying by MS one or more glycans selected from the group consisting of glycans 3200, 3210, 3300, 3310, 3320, 3400, 3410, 3420, 3500, 3510, 3520, 3600, 3610, 3620, 3630, 3700, 3710, 3720, 3730, 3740, 4200, 4210, 4300, 4301, 4310, 4311, 4320, 4400, 4401, 4410, 4411, 4420, 4421, 4430, 4431, 4500, 4501, 4510, 4511, 4520, 4521, 4530, 4531, 4540, 4541, 4600, 4601, 4610, 4611, 4620, 4621, 4630, 4631, 4641, 4650, 4700, 4701, 4710, 4711, 4720, 4730, 5200, 5210, 5300, 5301, 5310, 5311, 5320, 5400, 5401, 5402, 5410, 5411, 5412, 5420, 5421, 5430, 5431, 5432, 5500, 5501, 5502, 5510, 5511, 5512, 5520, 5521, 5522, 5530, 5531, 5541, 5600, 5601, 5602, 5610, 5611, 5612, 5620, 5621, 5631, 5650, 5700, 5701, 5702, 5710, 5711, 5712, 5720, 5721, 5730, 5731, 6200, 6210, 6300, 6301, 6310, 6311, 6320, 6400, 6401, 6402, 6410, 6411, 6412, 6420, 6421, 6432, 6500, 6501, 6502, 6503, 6510, 6511, 6512, 6513, 6520, 6521, 6522, 6530, 6531, 6532, 6540, 6541, 6600, 6601, 6602, 6603, 6610, 6611, 6612, 6613, 6620, 6621, 6622, 6623, 6630, 6631, 6632, 6640, 6641, 6642, 6652, 6700, 6701, 6711, 6721, 6703, 6713, 6710, 6711, 6712, 6713, 6720, 6721, 6730, 6731, 6740, 7200, 7210, 7400, 7401, 7410, 7411, 7412, 7420, 7421, 7430, 7431, 7432, 7500, 7501, 7510, 7511, 7512, 7600, 7601, 7602, 7603, 7604, 7610, 7611, 7612, 7613, 7614, 7620, 7621, 7622, 7623, 7632, 7640, 7700, 7701, 7702, 7703, 7710, 7711, 7712, 7713, 7714, 7720, 7721, 7722, 7730, 7731, 7732, 7740, 7741, 7751, 8200, 9200, 9210, 10200, 11200, 12200, and combinations thereof.

In some examples, including any of the foregoing, the method further includes diagnosing a patient with a ccRCC stage or condition based on the classification. In some examples, including any of the foregoing, the method further includes diagnosing the patient as having ccRCC based on the classification.

In some examples, including any of the foregoing, the method further includes treating the patient with a therapeutically effective amount of a therapeutic agent selected from the group consisting of a chemotherapeutic, an immunotherapy, a hormone therapy, a targeted therapy, a radiation therapy, a surgical therapy and combinations thereof.

In another example, set forth herein is a method for classifying a biological sample, comprising: obtaining a biological sample from a patient, wherein the biological sample includes one or more glycopeptides and/or glycoproteins; digesting and/or fragmenting one or more glycopeptides and/or glycoproteins; detecting and quantifying at least one or more multiple-reaction-monitoring (MRM) transitions selected from the group consisting of transitions 1-39; and inputting the quantification into a trained model to generate an output probability;

determining if the output probability is above or below a threshold for a classification; and classifying the biological sample based on whether the output probability is above or below the threshold for a classification.

In some examples, including any of the foregoing, the method further includes using a machine learning algorithm to train a model using the MRM transitions as inputs.

In another example, set forth herein is a method for classifying a biological sample, comprising: obtaining a biological sample from a patient, wherein the biological sample includes one or more glycopeptides and/or glycoproteins; digesting and/or fragmenting one or more glycopeptides and/or glycoproteins; detecting and quantifying at least one or more multiple-reaction-monitoring (MRM) transition associated with at least one or more glycopeptides consisting essentially of an amino acid sequence selected from the group consisting of SEQ ID NOs: 1-39, and combinations thereof, and inputting the quantification into a trained model to generate an output probability; determining if the output probability is above or below a threshold for a classification; and classifying the biological sample based on whether the output probability is above or below a threshold for a classification.

In some examples, including any of the foregoing, the method further includes training a machine learning algorithm using the MRM transitions as inputs.

In another example, set forth herein is a method for monitoring, treating, or both monitoring and treating a patient having ccRCC; the method comprising: obtaining, or having obtained, a biological sample from the patient, wherein the biological sample includes one or more glyco-peptides and/or glycoproteins; digesting and/or fragmenting, or having digested or having fragmented, one or more glycopeptides and/or glycoproteins; and detecting and quan-tifying one or more multiple-reaction-monitoring (MRM) transitions selected from the group consisting of transitions 1-39; inputting the quantification into a trained model to generate an output probability; determining if the output probability is above or below a threshold for a classification; and classifying the patient based on whether the output probability is above or below a threshold for a classification, wherein the classification is selected from the group con-sisting of: (A) a patient in need of a chemotherapeutic agent; (B) a patient in need of a immunotherapeutic agent; (C) a patient in need of hormone therapy; (D) a patient in need of a targeted therapeutic agent; (E) a patient in need of radia-tion therapy (F) a patient in need of surgery; (G) a patient in need of neoadjuvant therapy; (H) a patient in need of chemotherapeutic agent, immunotherapeutic agent, hor-mone therapy, targeted therapeutic agent, neoadjuvant therapy, radiation therapy, or a combination thereof, before surgery; (I) a patient in need of chemotherapeutic agent, immunotherapeutic agent, hormone therapy, targeted thera-peutic agent, neoadjuvant therapy, radiation therapy, or a combination thereof, after surgery; (J) or a combination thereof, administering a therapeutically effective amount of a therapeutic agent to the patient: wherein the therapeutic agent is selected from chemotherapy if classification A or J is determined; wherein the therapeutic agent is selected from immunotherapy if classification B or J is determined; or wherein the therapeutic agent is selected from hormone therapy if classification C or J is determined; or wherein the therapeutic intervention is selected from radiation therapy if classification D or J is determined; or wherein the therapeu-tic agent is selected from targeted therapy if classification E or J is determined wherein the therapeutic agent is selected from neoadjuvant therapy if classification G or J is deter-mined; wherein the therapeutic agent is selected from che-motherapeutic agent, immunotherapeutic agent, hormone therapy, targeted therapeutic agent, neoadjuvant therapy, radiation therapy, or a combination thereof if classification H or J is determined; and wherein the therapeutic agent is selected from chemotherapeutic agent, immunotherapeutic agent, hormone therapy, targeted therapeutic agent, neoad-juvant therapy, radiation therapy or a combination thereof if classification I or J is determined.

In some examples, including any of the foregoing, the method includes conducting multiple-reaction-monitoring mass spectroscopy (MRM-MS) on the biological sample.

In some examples, including any of the foregoing, the method includes quantifying one or more glycopeptides consisting essentially of an amino acid sequence selected from the group consisting of SEQ ID NOs: 1-39 and combinations thereof.

In some examples, including any of the foregoing, the method includes inputting the quantification of the amount of a glycopeptide consisting essentially of an amino acid sequence selected from the group consisting of SEQ ID NOs: 1-39 into a machine learning algorithm to train a model.

In some examples, including any of the foregoing, wherein the machine learning algorithm is selected from the group consisting of a deep learning algorithm, a neural network algorithm, an artificial neural network algorithm, a supervised machine learning algorithm, a linear discriminant analysis algorithm, a quadratic discriminant analysis algo-rithm, a support vector machine algorithm, a linear basis function kernel support vector algorithm, a radial basis function kernel support vector algorithm, a random forest algorithm, a genetic algorithm, a nearest neighbor algorithm, k-nearest neighbors, a naive Bayes classifier algorithm, a logistic regression algorithm, or a combination thereof.

In some examples, including any of the foregoing, wherein the analyzing the transitions includes selecting peaks and/or quantifying detected glycopeptide fragments with a machine learning algorithm.

In another example, set forth herein is a method for monitoring the disease progression in a patient having ccRCC; the method comprising: obtaining, or having obtained, a biological sample from the patient; performing mass spectroscopy of the biological sample using MRM-MS with a QQQ and/or qTOF spectrometer to detect and quan-tify one or more glycopeptides consisting essentially of an amino acid sequence selected from the group consisting of SEQ ID NOs: 1-39; or to detect one or more MRM transi-tions selected from transitions 1-39; inputting the quantifi-cation of the detected glycopeptides or the MRM transitions into a trained model to generate an output probability, determining if the output probability is above or below a threshold for a classification; and identifying a prognosis for the patient based on whether the output probability is above or below a threshold for a classification; and diagnosing the patient as having ccRCC based on the diagnostic classifi-cation.

In some examples, including any of the foregoing, wherein the analyzing the detected glycopeptides includes using a machine learning algorithm.

In some examples, including any of the foregoing, wherein the sample from the patient includes at least 1, at least 2, at least 3, at least 4, at least 5, at least 6, at least 7, at least 8, at least 9, at least 11, at least 12, at least 13, at least 14, at least 15, at least 16, at least 17, at least 18, at least 19, at least 21, at least 22, at least 23, at least 24, at least 25, at least 26, at least 27, at least 28, at least 29, at least 31, at least 32, at least 33, at least 34, at least 35, at least 36, at least 37, at least 38, or at least 39 glycopeptides consisting essentially of an amino acid sequence selected from the group consist-ing of SEQ ID NOs: 1-39.

In some examples, including any of the foregoing, wherein the sample from the patient includes at least 9 glycopeptides consisting essentially of an amino acid sequence selected from the group consisting of SEQ ID NOs: 1-39.

In some examples, including any of the foregoing, wherein the sample from the patient includes at least 10 glycopeptides consisting essentially of an amino acid sequence selected from the group consisting of SEQ ID NOs: 1-39.

In some examples, including any of the foregoing, the method includes obtaining, or having obtained, a biological sample from the patient every month when the patient is likely to have a more aggressive disease.

In some examples, including any of the foregoing, the method includes obtaining, or having obtained, a biological sample from the patient every quarter when the patient is likely to have a more aggressive disease.

In some examples, including any of the foregoing, the method includes obtaining, or having obtained, a biological sample from the patient every year when the patient is likely to have a less aggressive disease.

In some examples, including any of the foregoing, the method includes predicting the amount of time from diagnosis to progression of the disease.

In some examples, including any of the foregoing, the progression of the disease includes distant metastasis.

In some examples, including any of the foregoing, the progression of the disease includes death due to the disease.

In some examples, including any of the foregoing, the progression of the disease includes the cumulative, yearly odds of developing a distant metastasis after surgical resection of a primary tumor.

In another example, set forth herein is a glycopeptide consisting of an amino acid sequence selected from the group consisting of SEQ ID NOs: 1-39, and combinations thereof.

In another example, set forth herein is a glycopeptide consisting essentially of an amino acid sequence selected from the group consisting essentially of SEQ ID NOs:1-39, and combinations thereof.

V. Kits

In another example, set forth herein is a kit comprising one or more glycopeptide standards, one or more buffers, and one or more glycopeptides consisting essentially of an amino acid sequence selected from the group consisting of SEQ ID NOs: 1-39.

In some examples, including any of the foregoing, the kit comprises reagents for the preparation of a sample for LC/MS analysis.

In some examples, including any of the foregoing, the kit comprises one or more enzymes for protein digestion.

In some examples, including any of the foregoing, the kit comprises QQQ MS instrument parameters for the quantification of the one or more glycopeptides consisting essentially of an amino acid sequence selected from the group consisting of SEQ ID NOs: 1-39.

VI. Examples

Chemicals and Reagents. Glycoprotein standards purified from human serum/plasma were purchased from Sigma-Aldrich (St. Louis, MO) unless stated otherwise. Sequencing grade trypsin was purchased from Promega (Madison, WI). Dithiothreitol (DTT) and iodoacetamide (IAA) were purchased from Sigma-Aldrich (St. Louis, MO). Human serum was purchased from Sigma-Aldrich (St. Louis, MO) unless stated otherwise.

Sample Preparation. Serum samples and glycoprotein standards were reduced, alkylated and then digested with trypsin in a water bath at 37° C. for 18 hours. For example, Serum samples were reduced with DTT and alkylated with IAA followed by digestion with trypsin in a water bath at 37

C for 18 hours. To quench the digestion, formic acid was added to each sample after incubation to a final concentration of 1% (v/v).

LC-MS/MS Analysis. For quantitative analysis, tryptic digested serum samples were injected into a high pressure liquid chromatography (HPLC) system coupled to a triple quadrupole (QqQ) mass spectrometer. The separation was conducted on a reverse phase column. Solvents A and B used in the binary gradient were composed of mixtures of water, acetonitrile and formic acid. Typical positive ionization source parameters were utilized after source tuning with vendor supplied standards. The following ranges were evaluated: source spray voltage between 3-5 kV, temperature 250-350° C., and nitrogen sheath gas flow rate 20-40 psi. The scan mode of instrument used was dMRM.

For the glycoproteomic analysis, enriched serum glycopeptides were analyzed with a Thermo Fisher Scientific Q Exactive™ Hybrid Quadrupole-Orbitrap™ Mass spectrometer or an Agilent 6495B Triple Quadrupole LC/MS. In certain examples, digested serum samples were injected into an Agilent 6490 triple quadrupole mass spectrometer equipped with an Agilent 1290 infinity UHPLC system and an Agilent ZORBAX Eclipse Plus C18 column (2.1 mm×150 mm i.d., 1.8 um particle size). Separation of the peptides and glycopeptides was performed using a 70-min binary gradient. The aqueous mobile phase A was 3% acetonitrile, 0.1% formic acid in water (v/v), and the organic mobile phase B was 90% acetonitrile, 0.1% formic acid in water (v/v). The flow rate was set at 0.5 mL/min. Electrospray ionization (ESI) was used as the ionization source and was operated in positive ion mode. The triple quadrupole was operated in dynamic multiple reaction monitoring (dMRM) mode. The peptide and glycopeptide transitions employed overlap with those published in Li, et al., Site-specific glycosylation quantitation of 50 serum glycoproteins enhanced by predictive glycopeptidomics for improved disease biomarker discovery (2019). URL https://acs-.figshare.com/articles/Site-Specific_Glycosylation_Quantitation_of_50_Serum_ Glycoproteins_Enhanced_by_Predictive_G lycopeptid-omics_for_Improved_Disease_Biomarker_Discovery/ 7905002.

MRM Mass Spectroscopy settings, sample preparation, and reagents are set forth in Li, et al., Site-Specific Glycosylation Quantification of 50 serum Glycoproteins Enhanced by Predictive Glycopeptidomics for Improved Disease Biomarker Discovery, Anal. Chem. 2019, 91, 5433-5445; DOI: 10.1021/acs.analchem.9b00776, the entire contents of which are herein incorporated by reference in its entirety for all purposes. Also incorporated by reference herein in its entirety for all purposes is the Supplemental Information for Wu, Z. et al., PB-Net: Automatic Peak Integration by Sequential Deep Learning for Multiple Reaction Monitoring, submitted, Journal of Proteome Research. Certain methods of identifying peaks from U.S. Provisional Patent Application No. 62/826,228, filed Mar. 29, 2019, and titled AUTOMATED DETECTION OF BOUNDARIES IN MASS SPECTROMETY DATA were employed. The entire contents U.S. Provisional Patent Application No. 62/826, 228 are herein incorporated by reference in their entirety for all purposes.

Example 1

39 biomarkers were identified as significantly associated with progression free survival (age-adjusted Cox proportional hazards model; FDR<0.05. These biomarkers are described by SEQ ID NOs: 1-39.

The 39 biomarkers were selected by starting with a panel of 408 glycopeptides which were previously identified as relevant to cancer and RCC specifically. See Li, et al., Anal. Chem. 2019, 91, 5433-5445 and International Patent Application No. PCT/US2020/016286, filed Jan. 31, 2020, the entire contents of each of which are herein incorporated by reference in its entirety for all purposes. These 39 markers were dichotomized at an expression level that maximized Harrell's c-index, and the resulting Kaplan-Meier plots are shown in FIGS. 3-41.

In FIG. 1, the solid line represents samples from patients having ccRCC which includes 0-9 of the biomarker glycopeptides set forth in SEQ ID Nos.: 1-39. This patient would be considered as likely having less aggressive disease.

In FIG. 1, the dashed line represents samples from patients having ccRCC which includes 10 or more of the biomarker glycopeptides set forth in SEQ ID Nos.: 1-39. This patient would be considered as likely having more aggressive disease.

Figure 2:
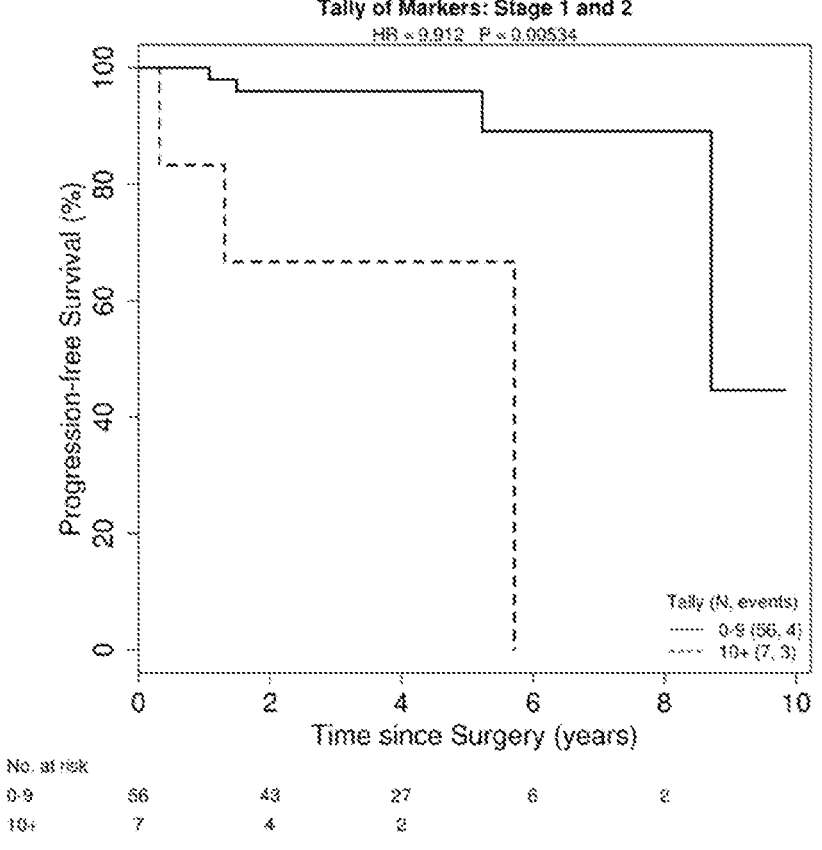
FIG. 2. shows a Kaplan-Meier plot for glycopeptides 1-39 set forth herein for a Tally of Markers for Stage 1 and 2 ccRCC.
Figure 3:
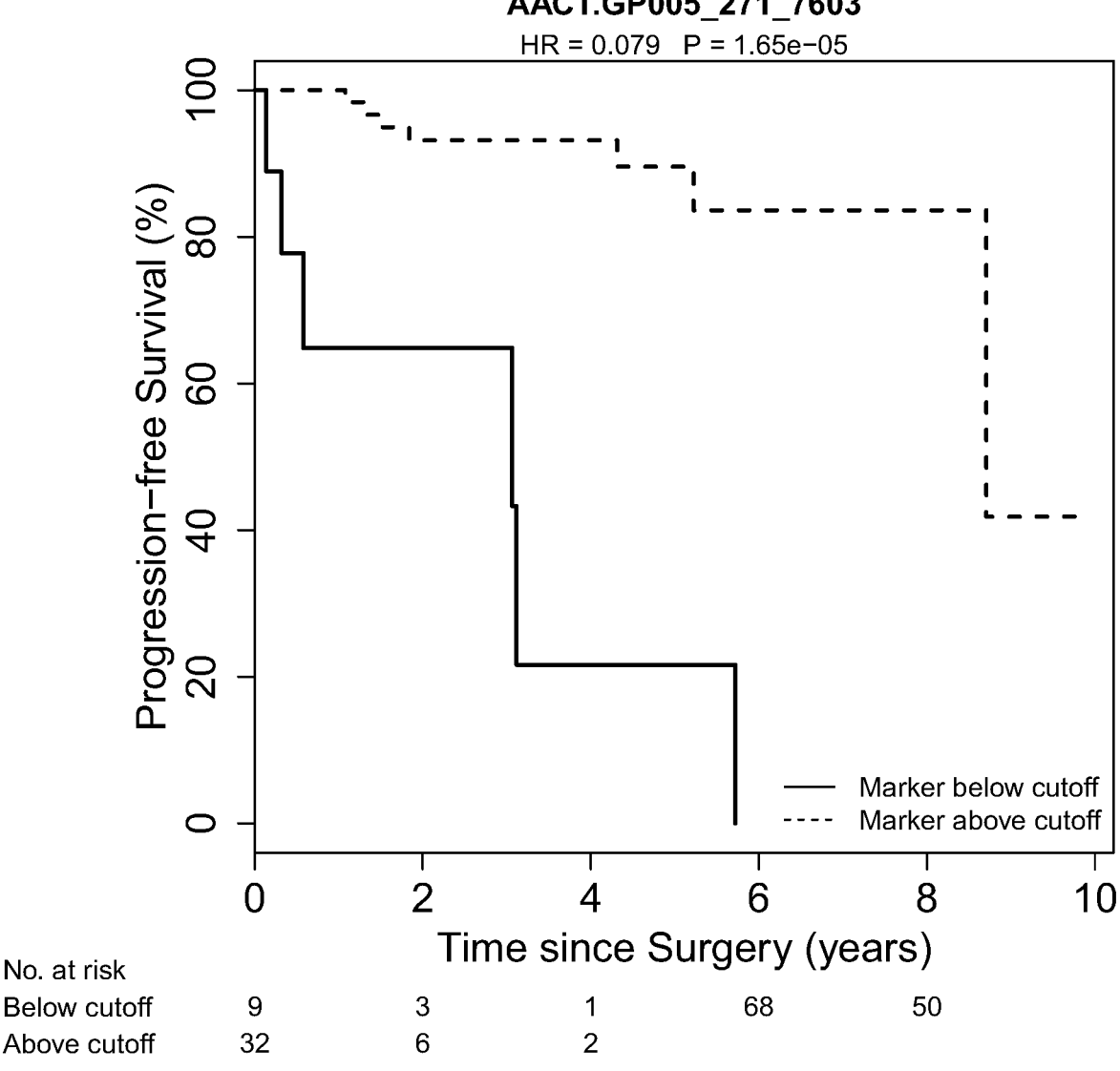
FIGS. 3-41 show survivability plots for certain glycopep-tide fragments set forth herein.
Figure 4:
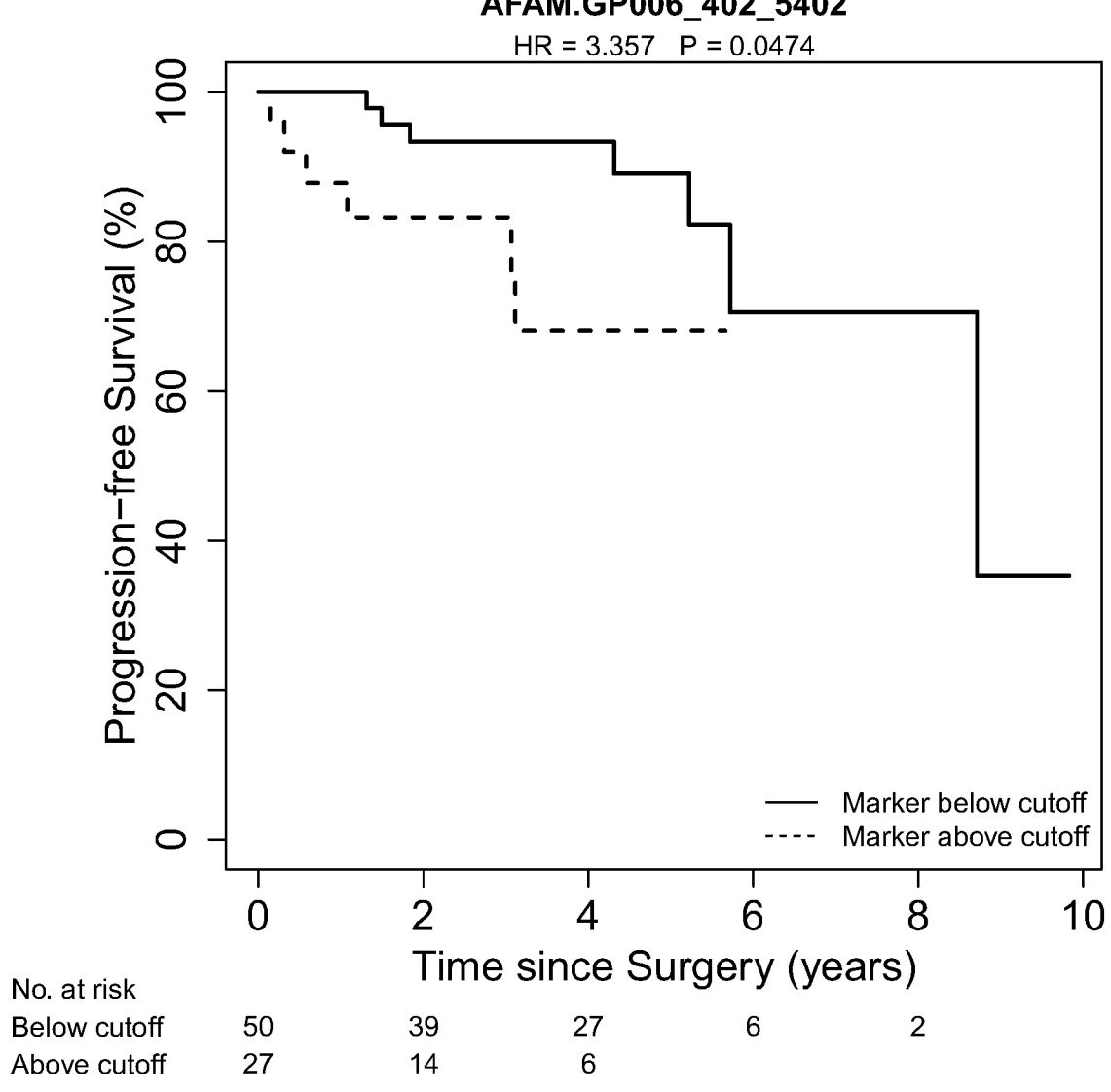
Figure 5:
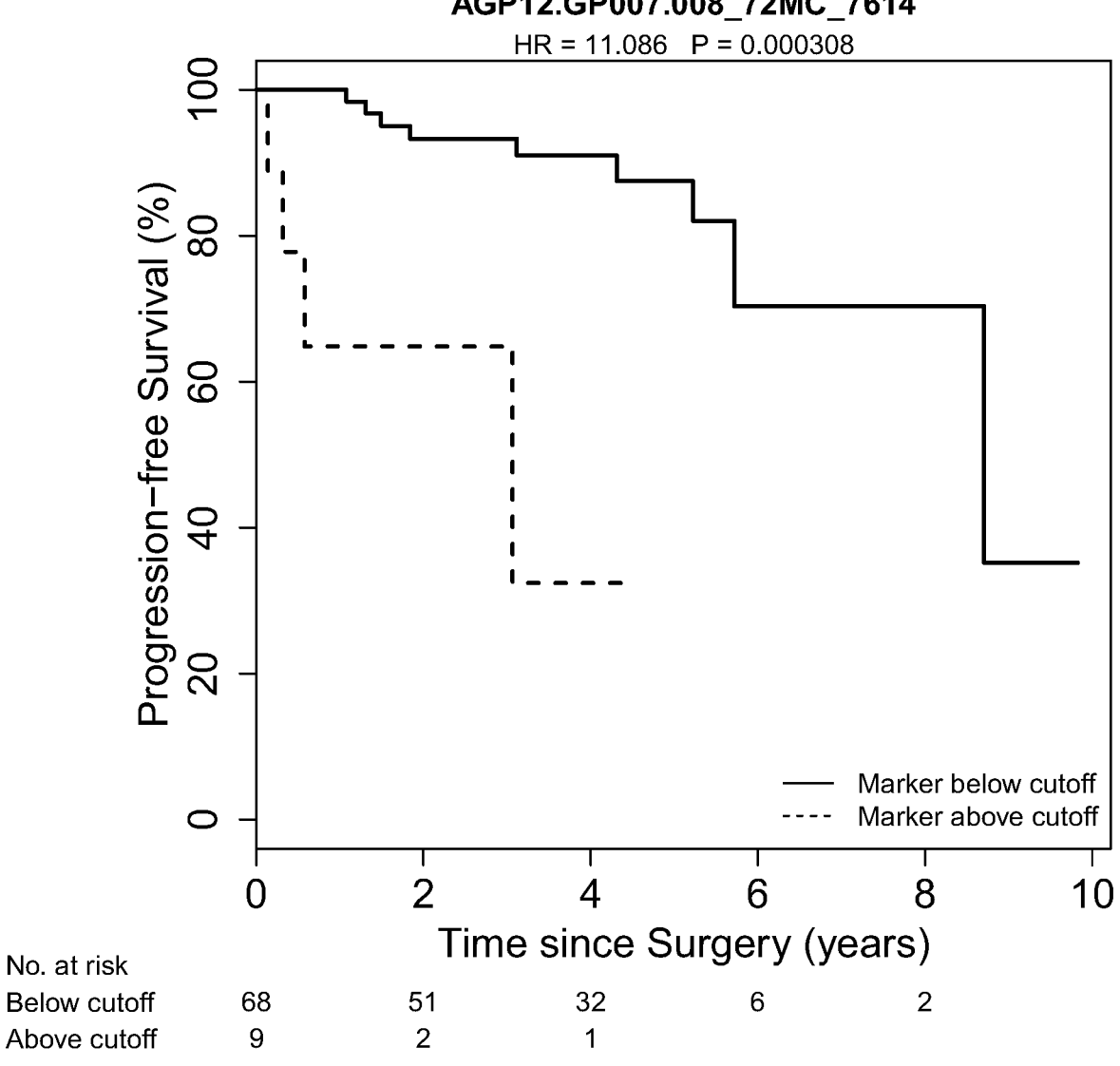
Figure 6:
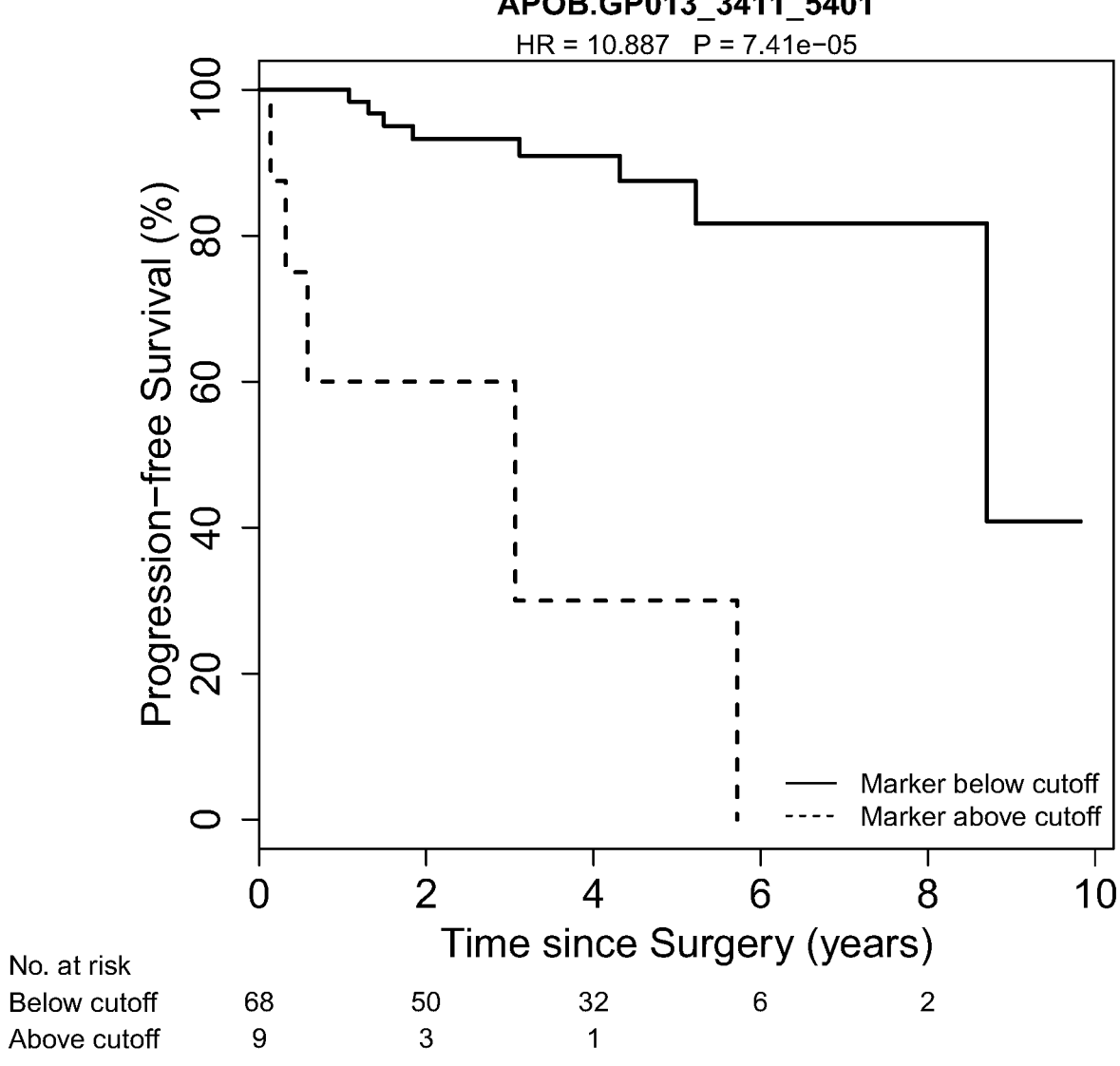
Figure 7:
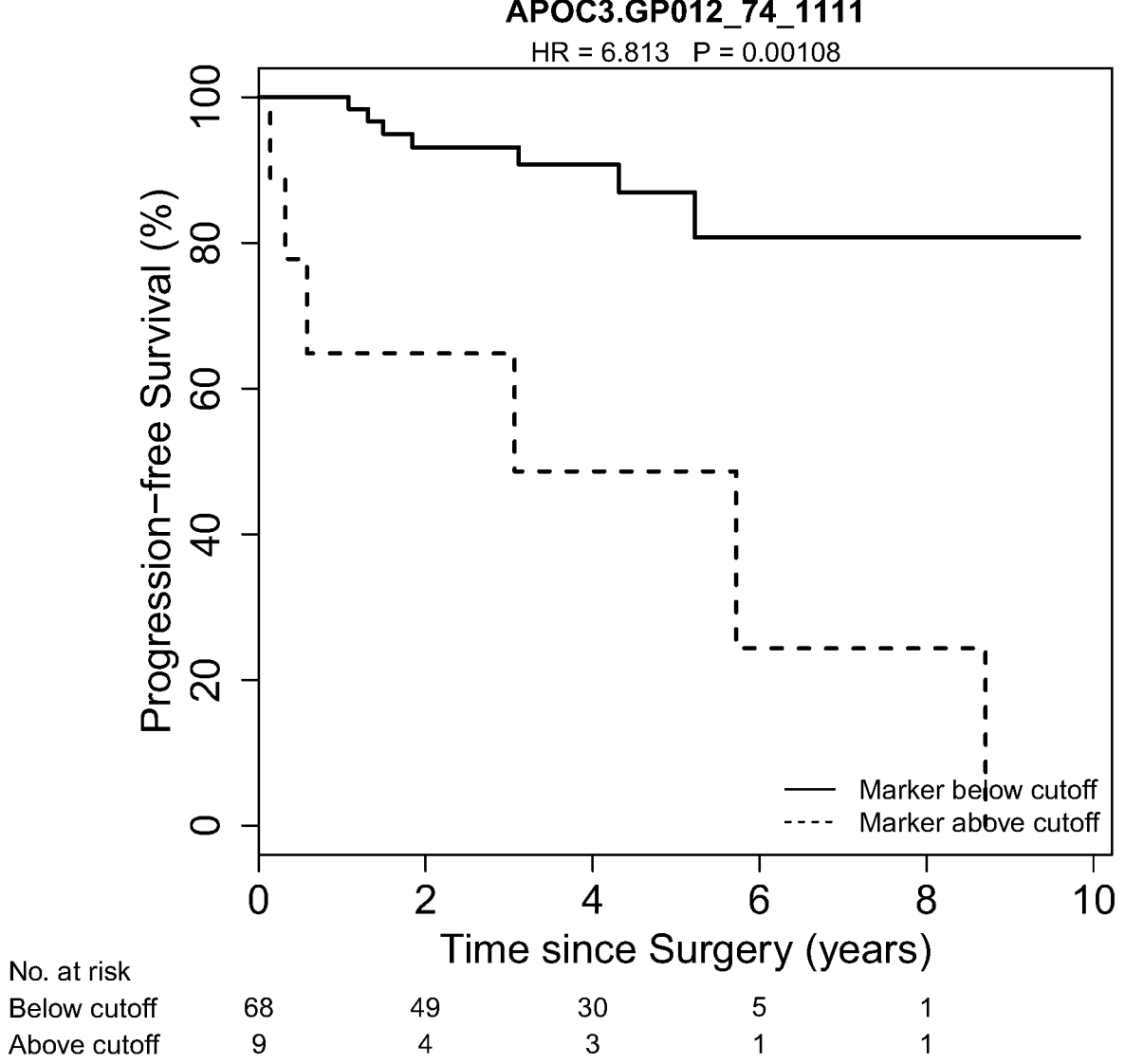
Figure 8:
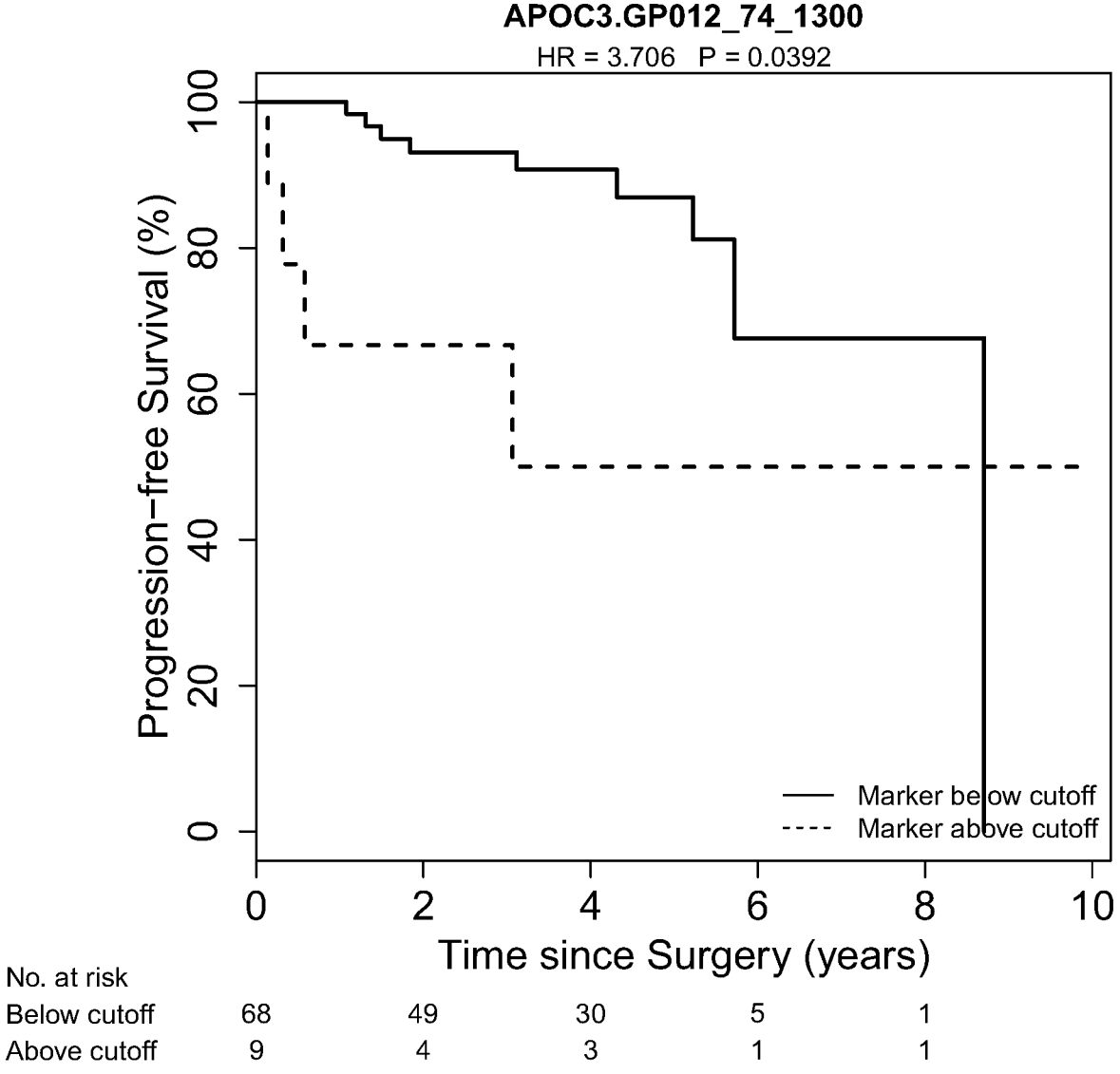
Figure 9:
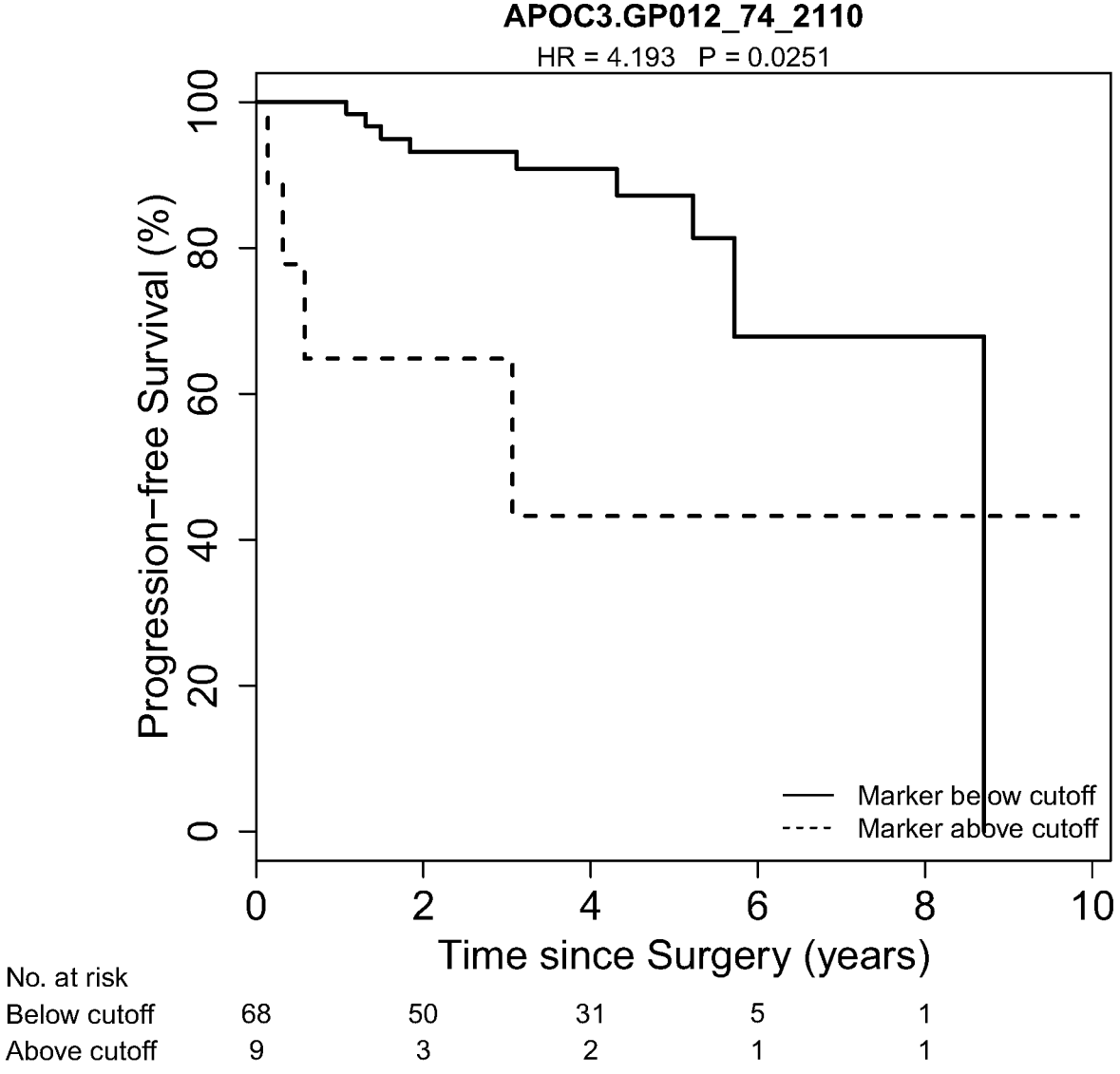
Figure 10:
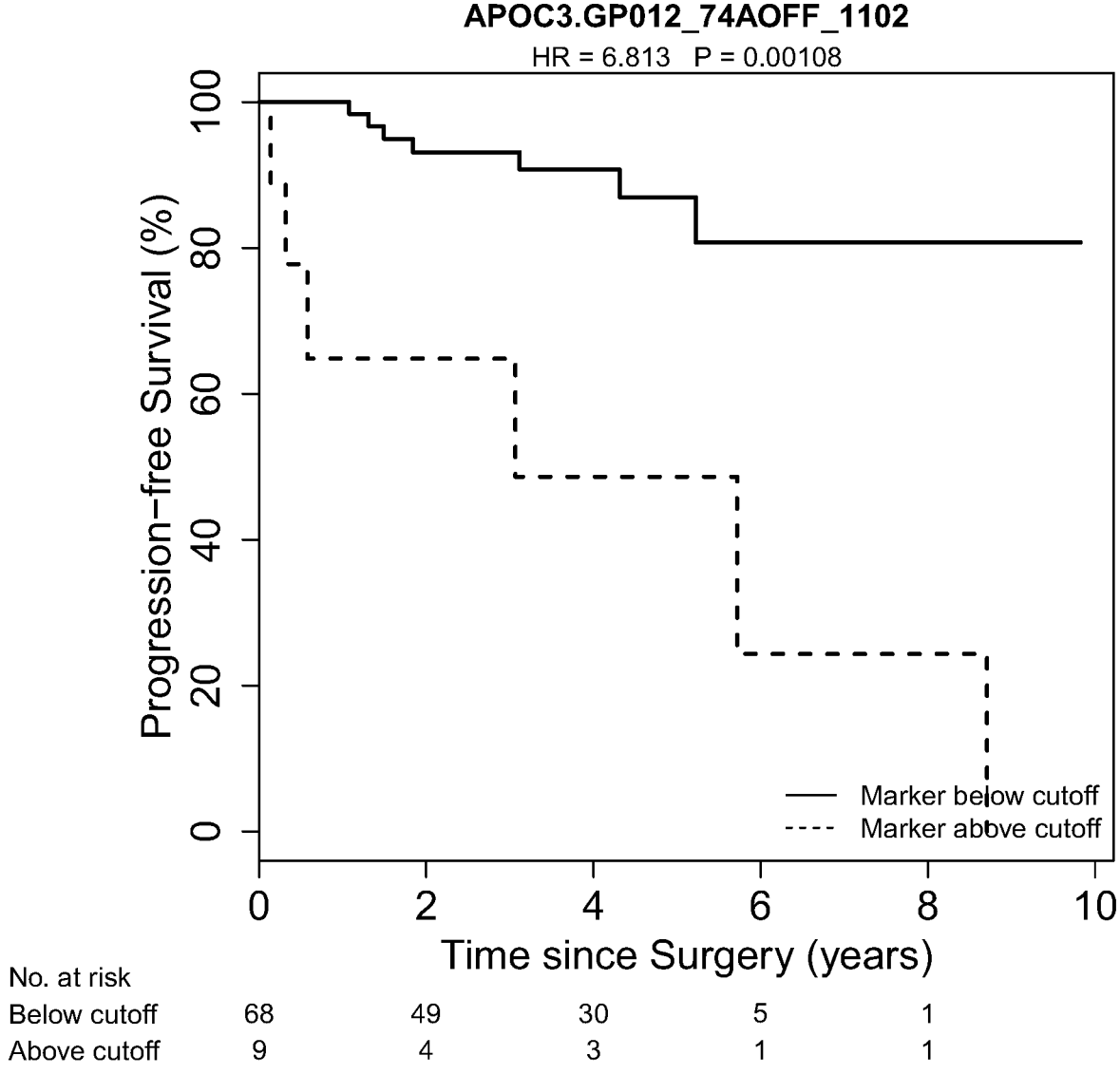
Figure 11:
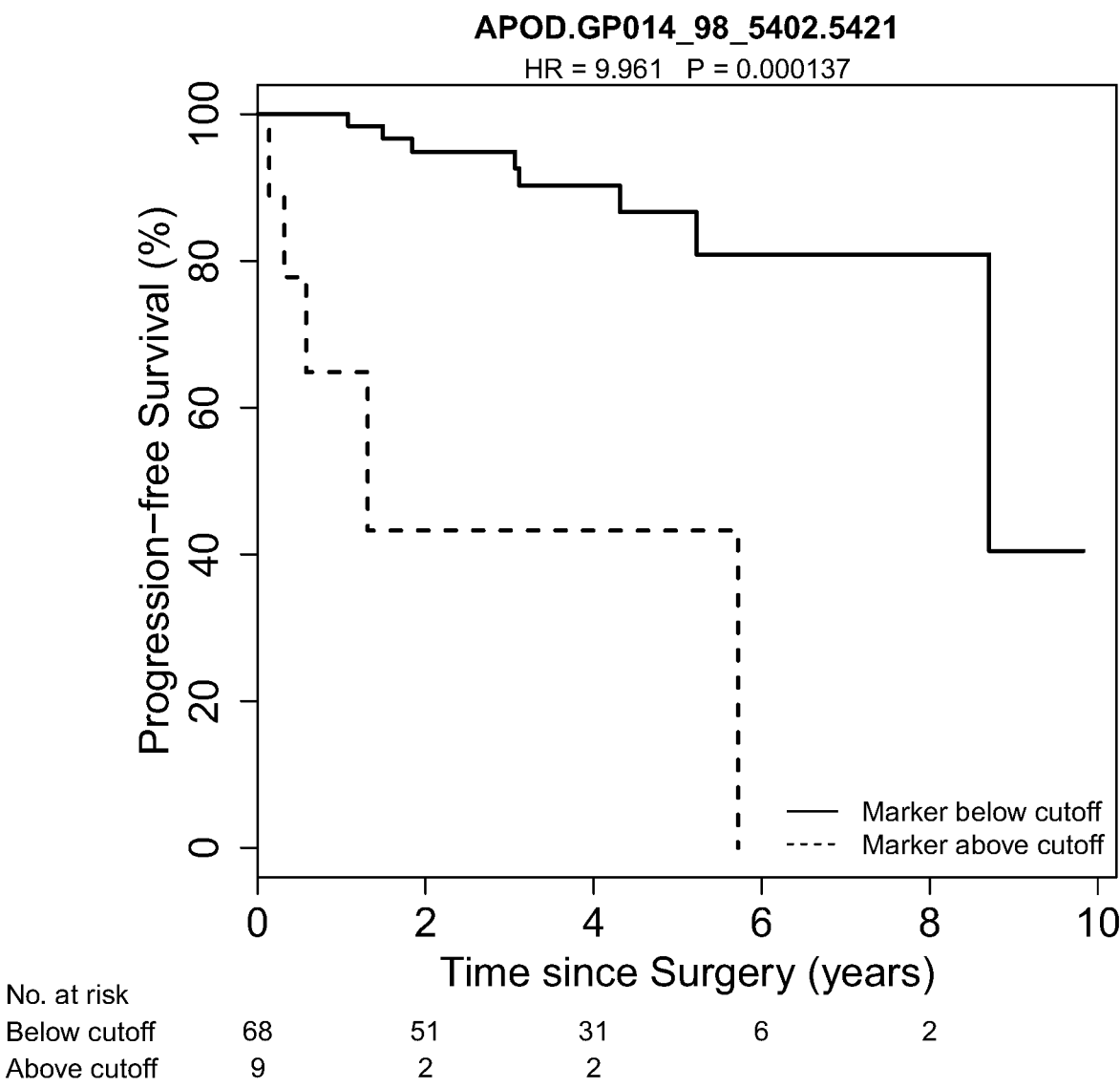
Figure 12:
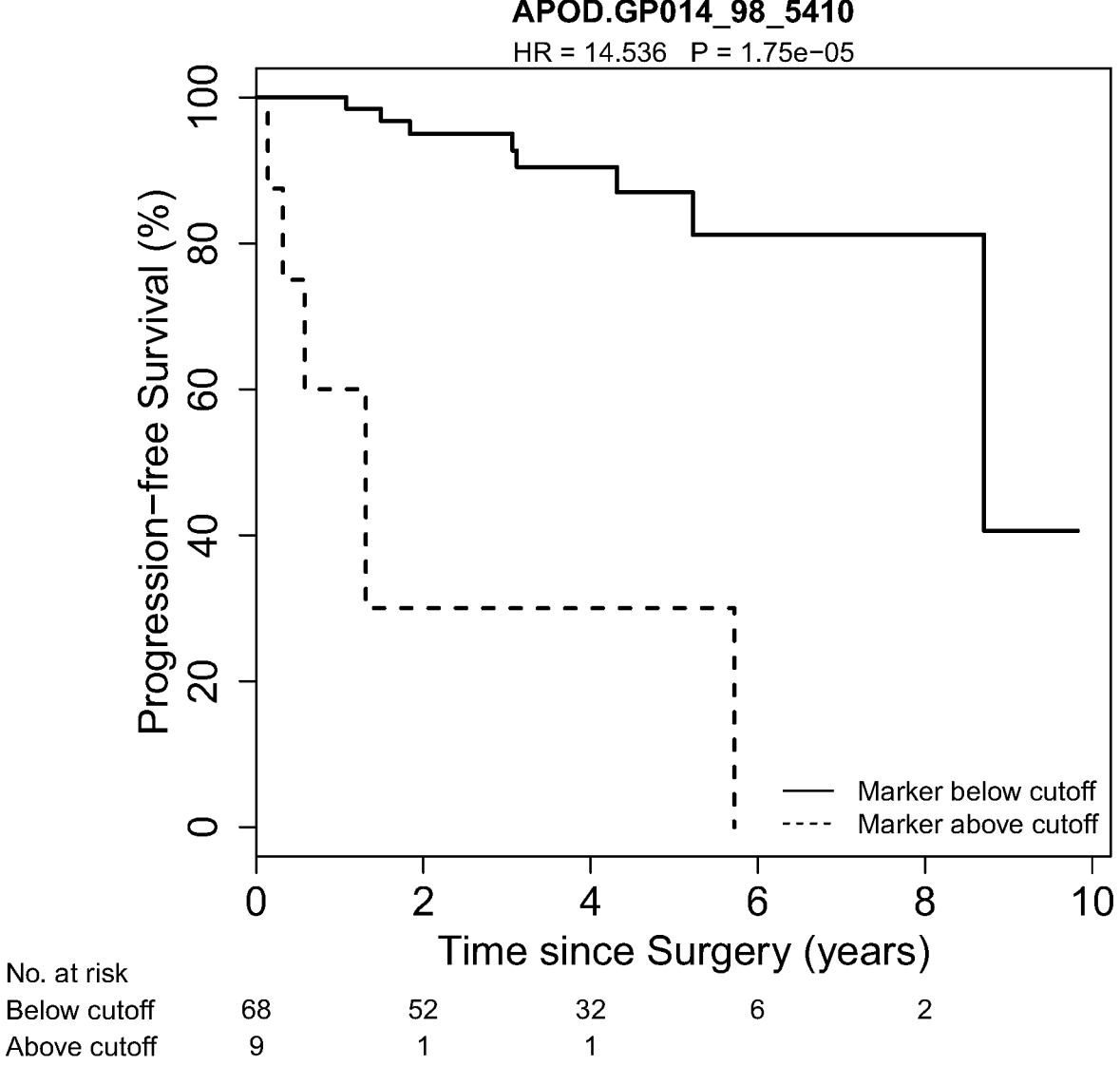
Figure 13:
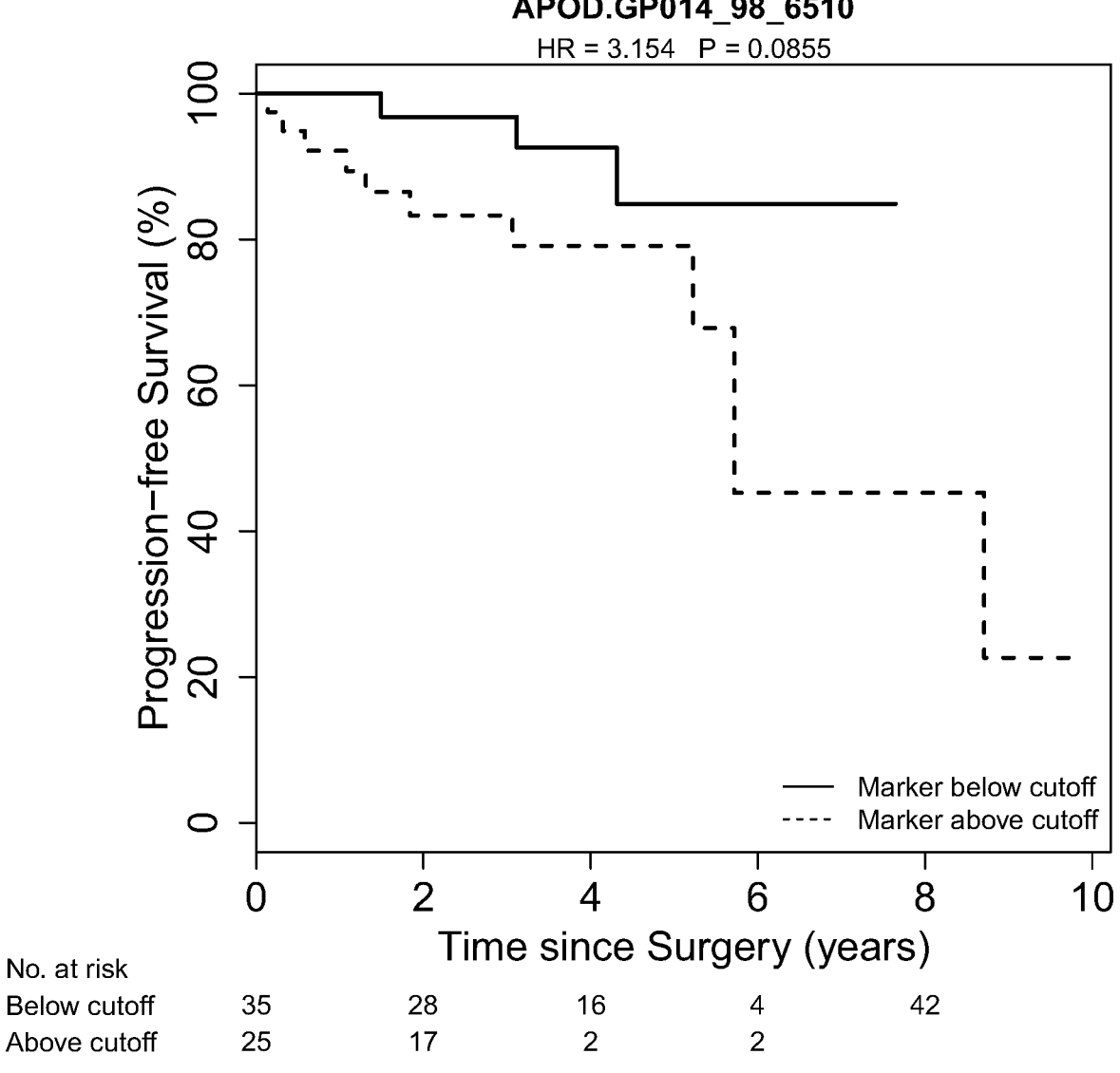
Figure 14:
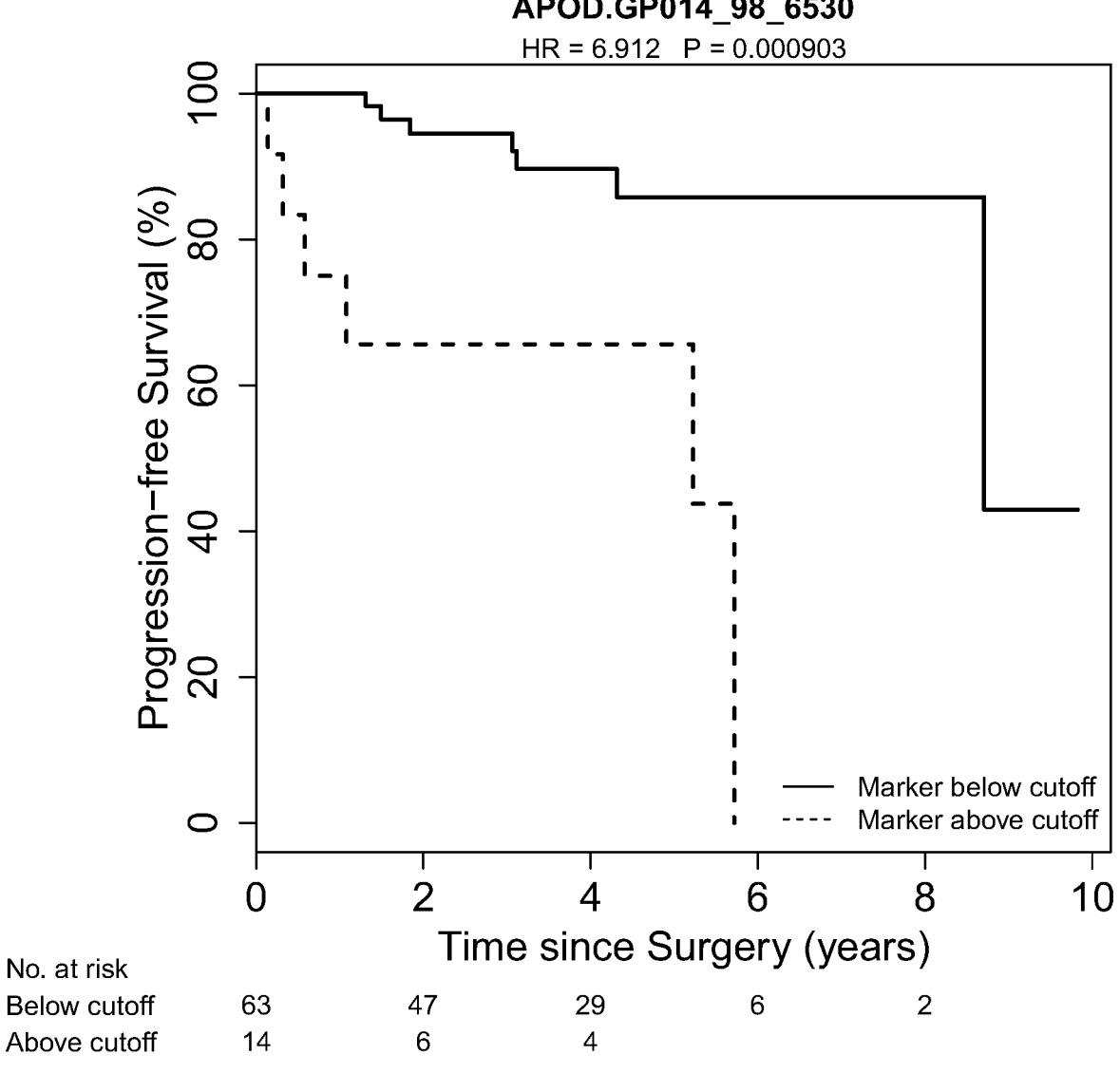
Figure 15:
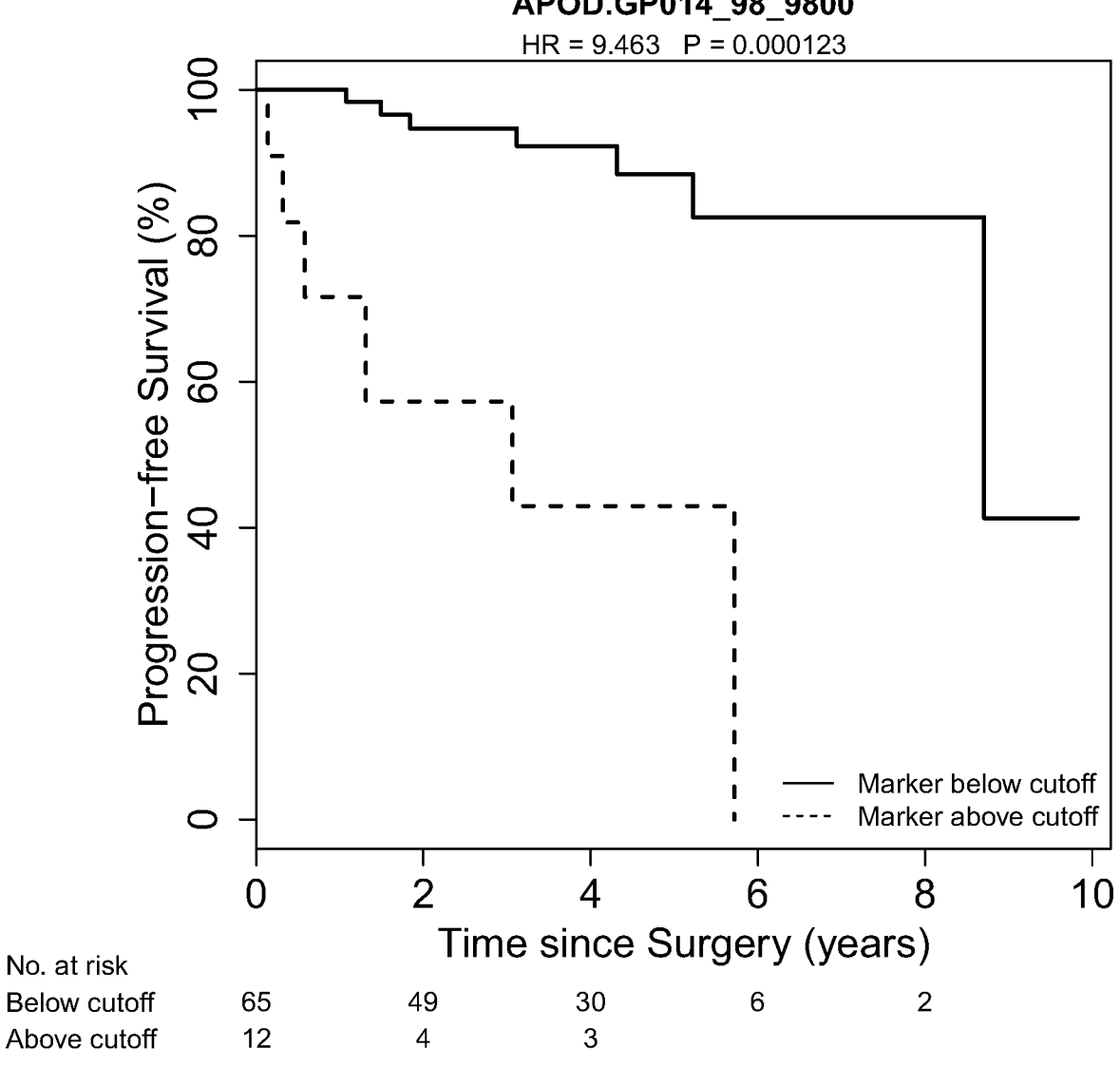
Figure 16:
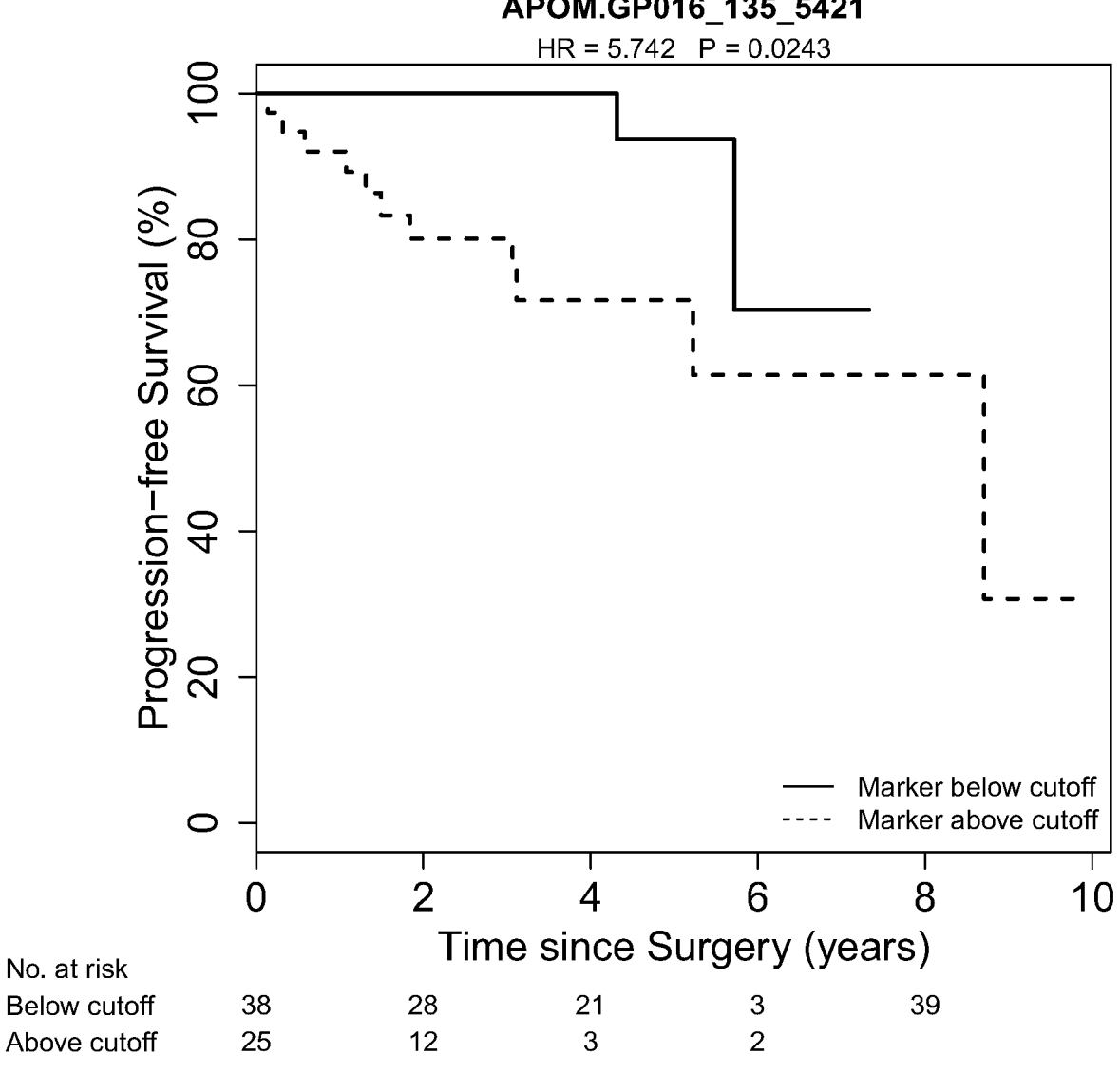
Figure 17:
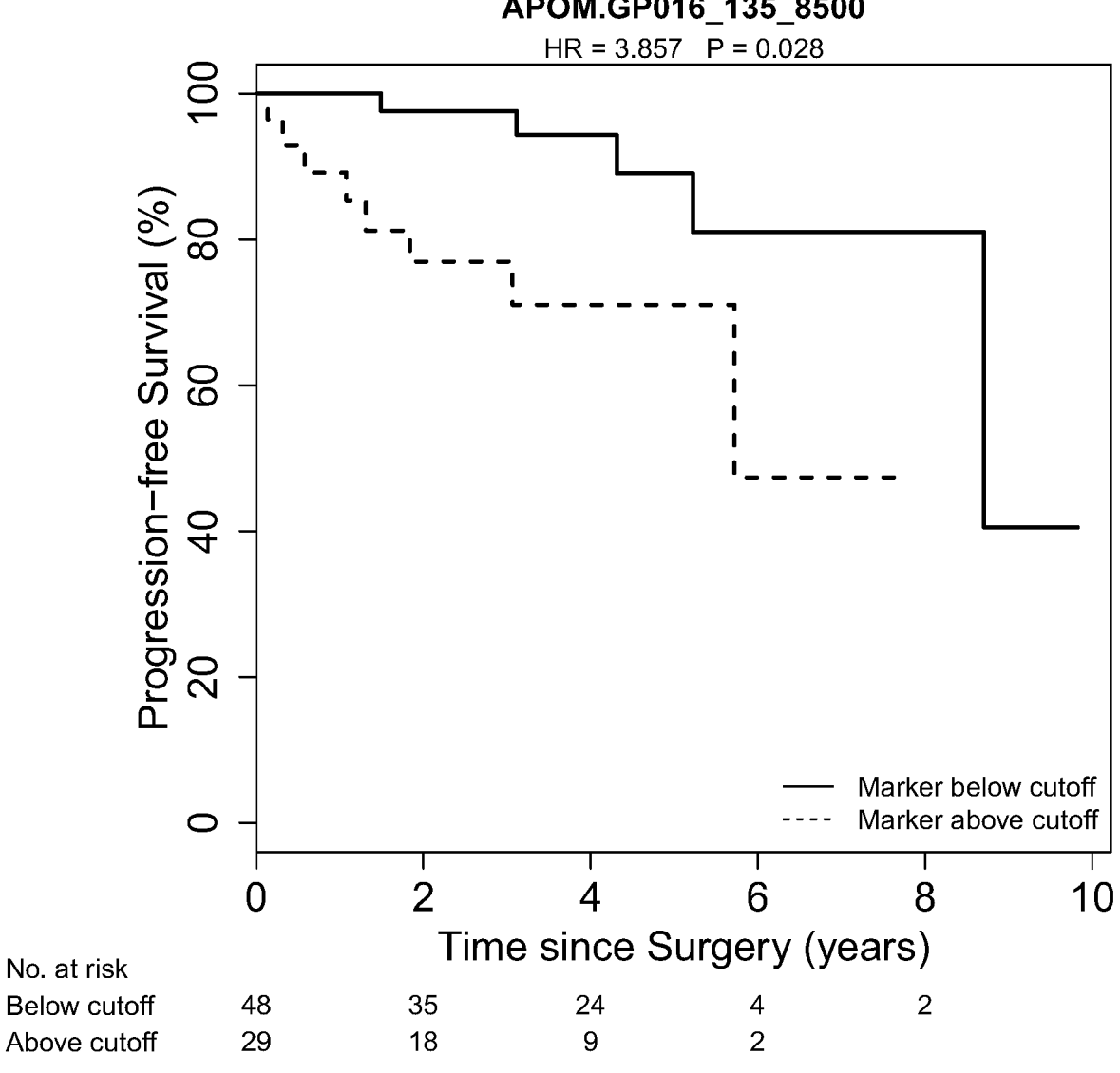
Figure 18:
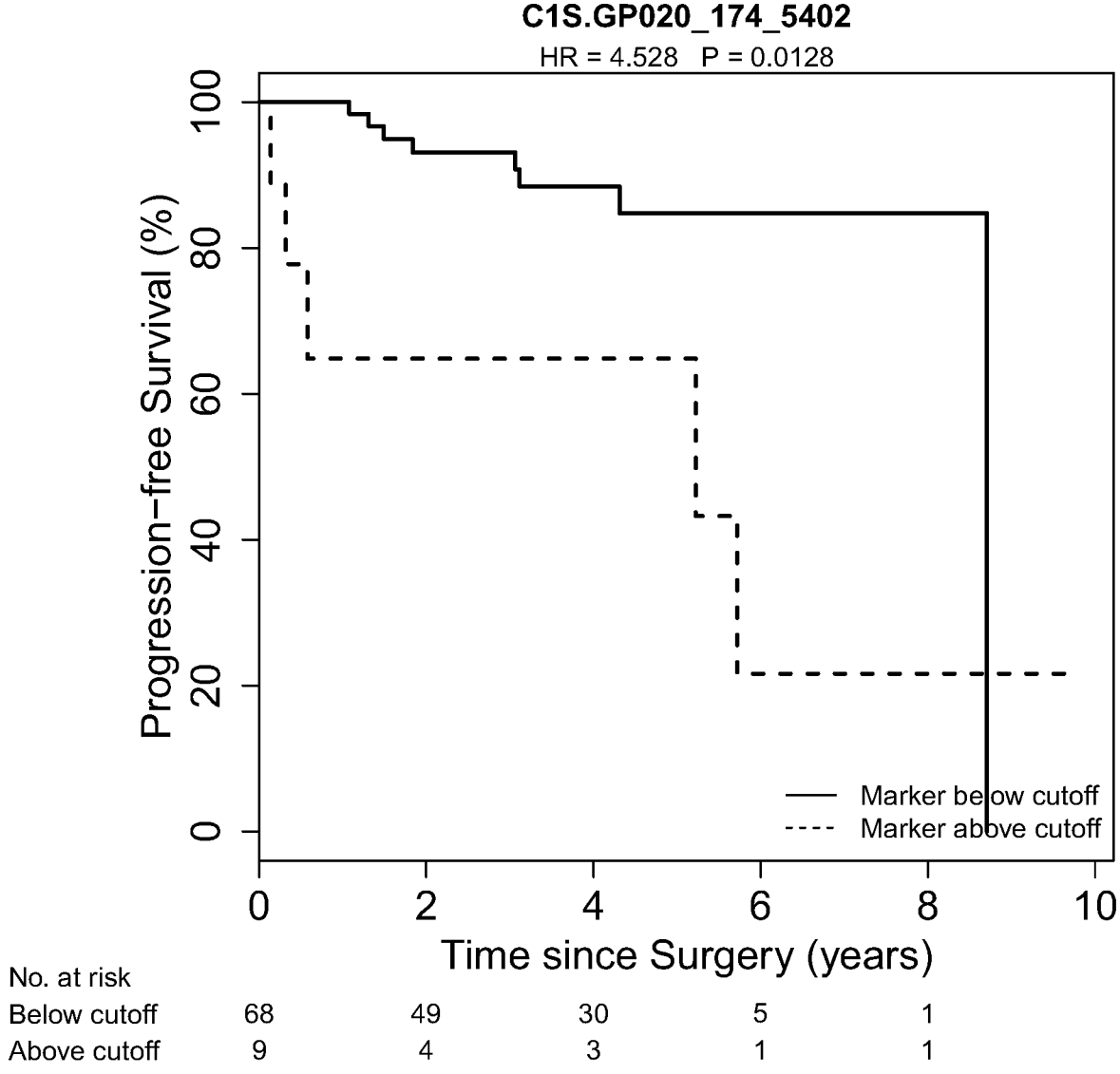
Figure 19:
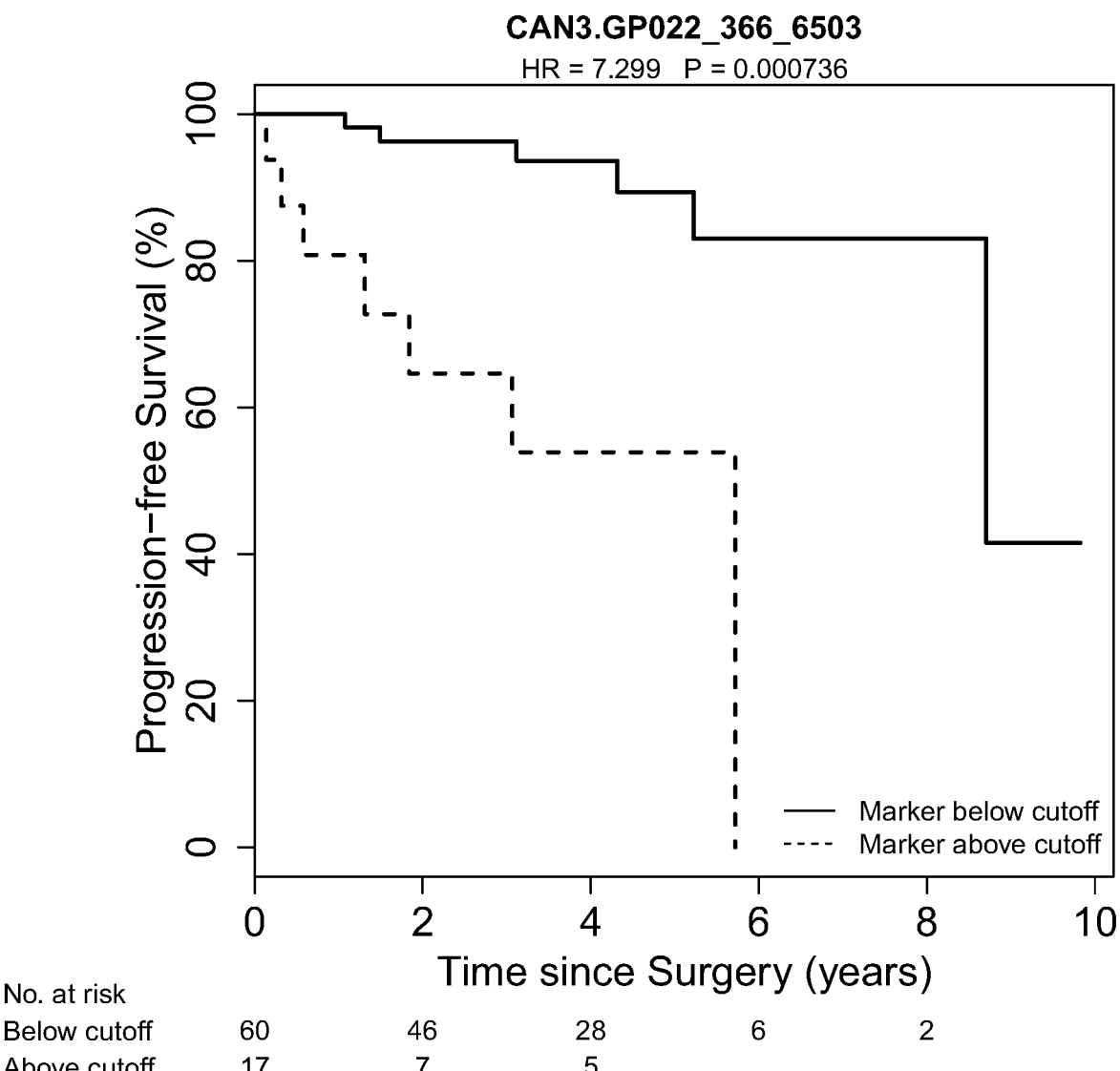
Figure 20:
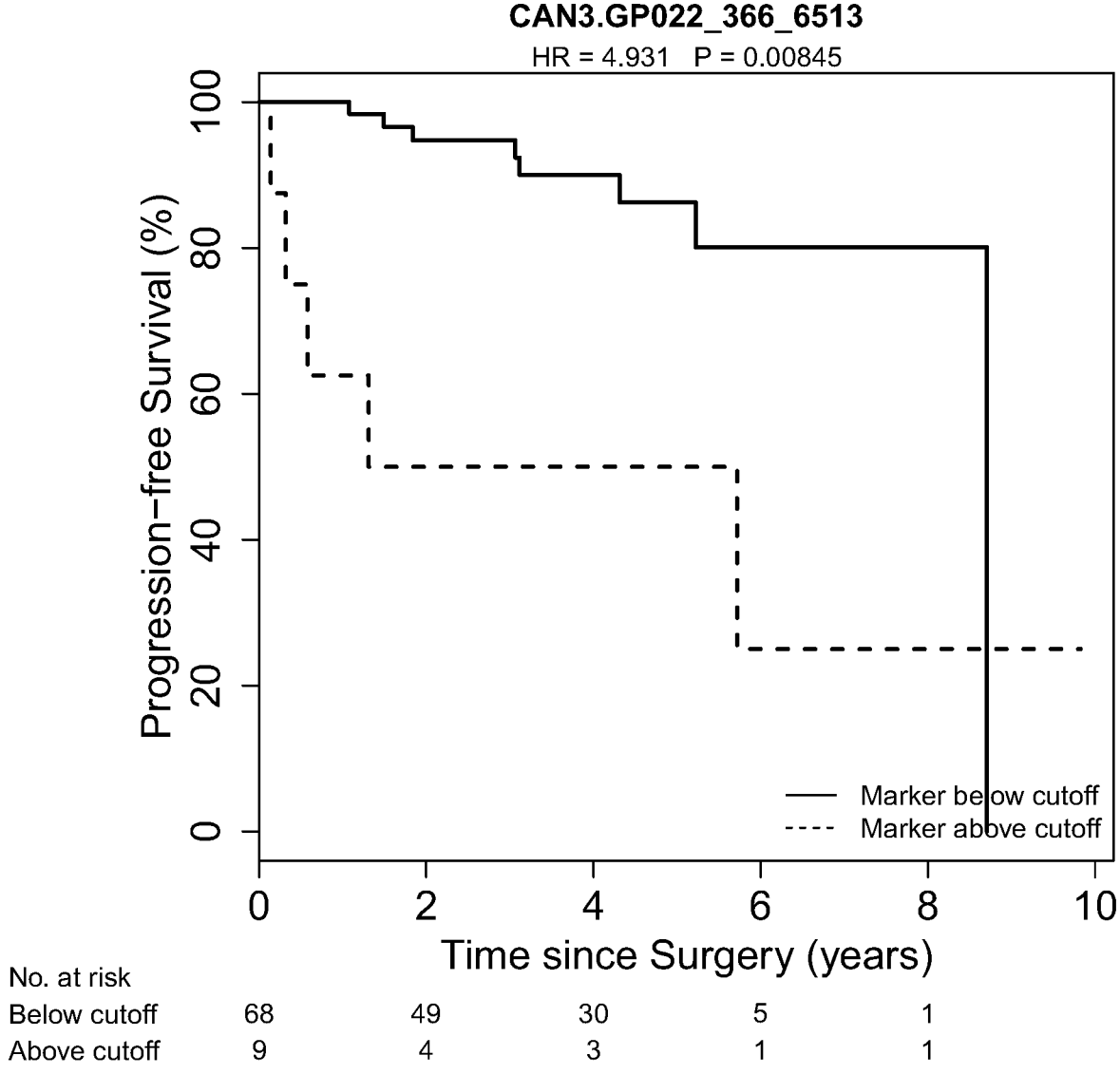
Figure 21:
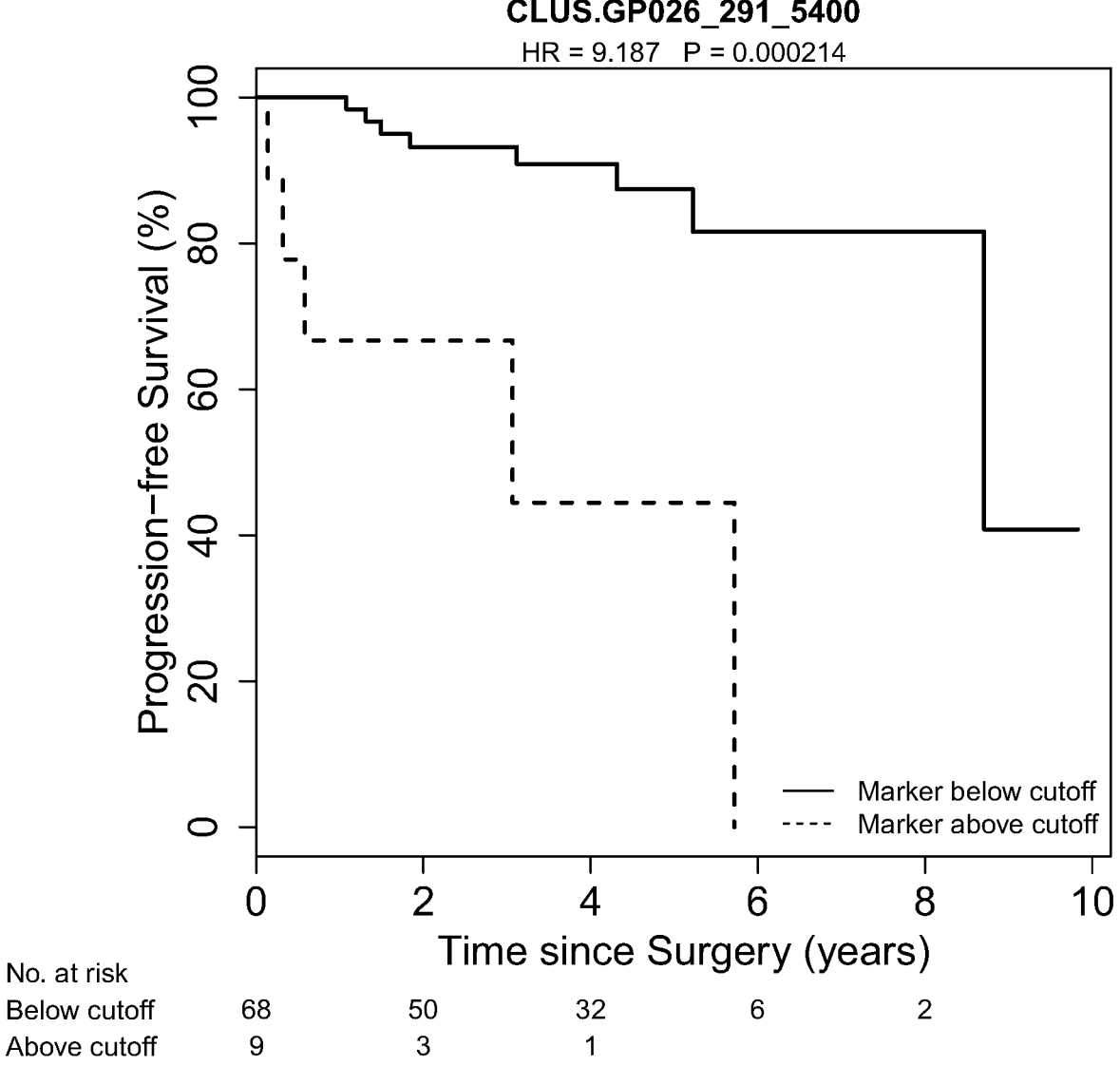
Figure 22:
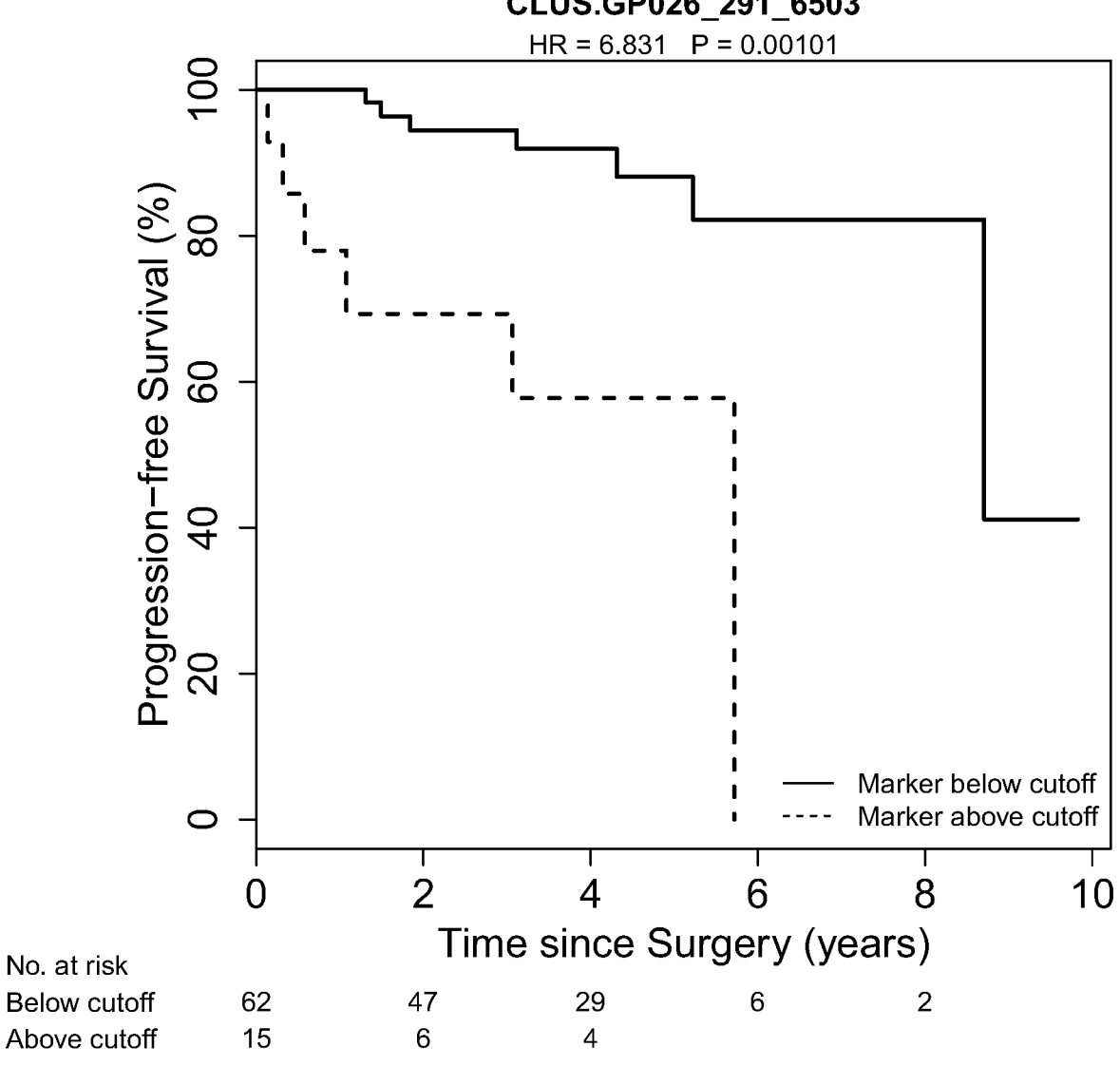
Figure 23:
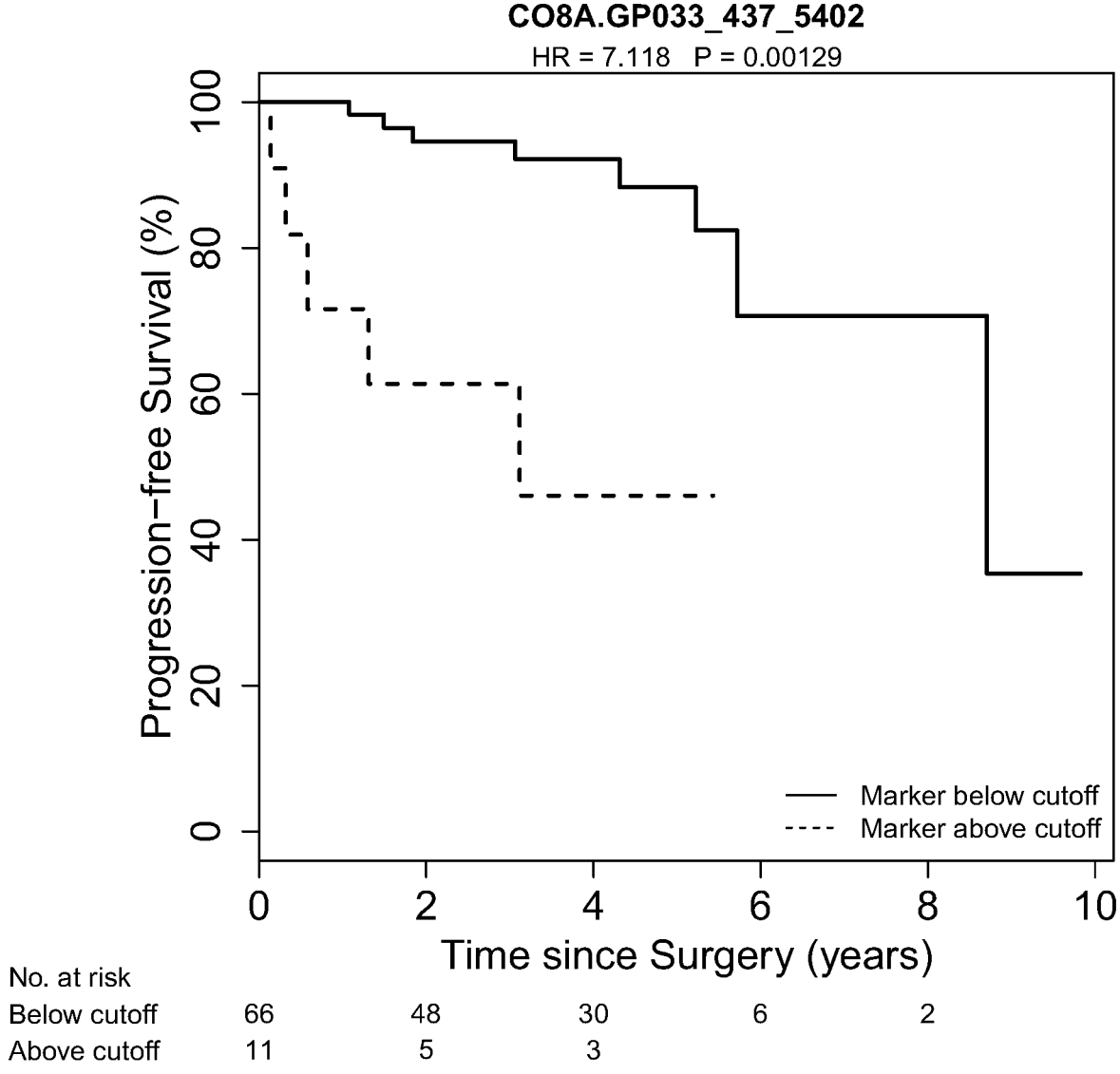
Figure 24:
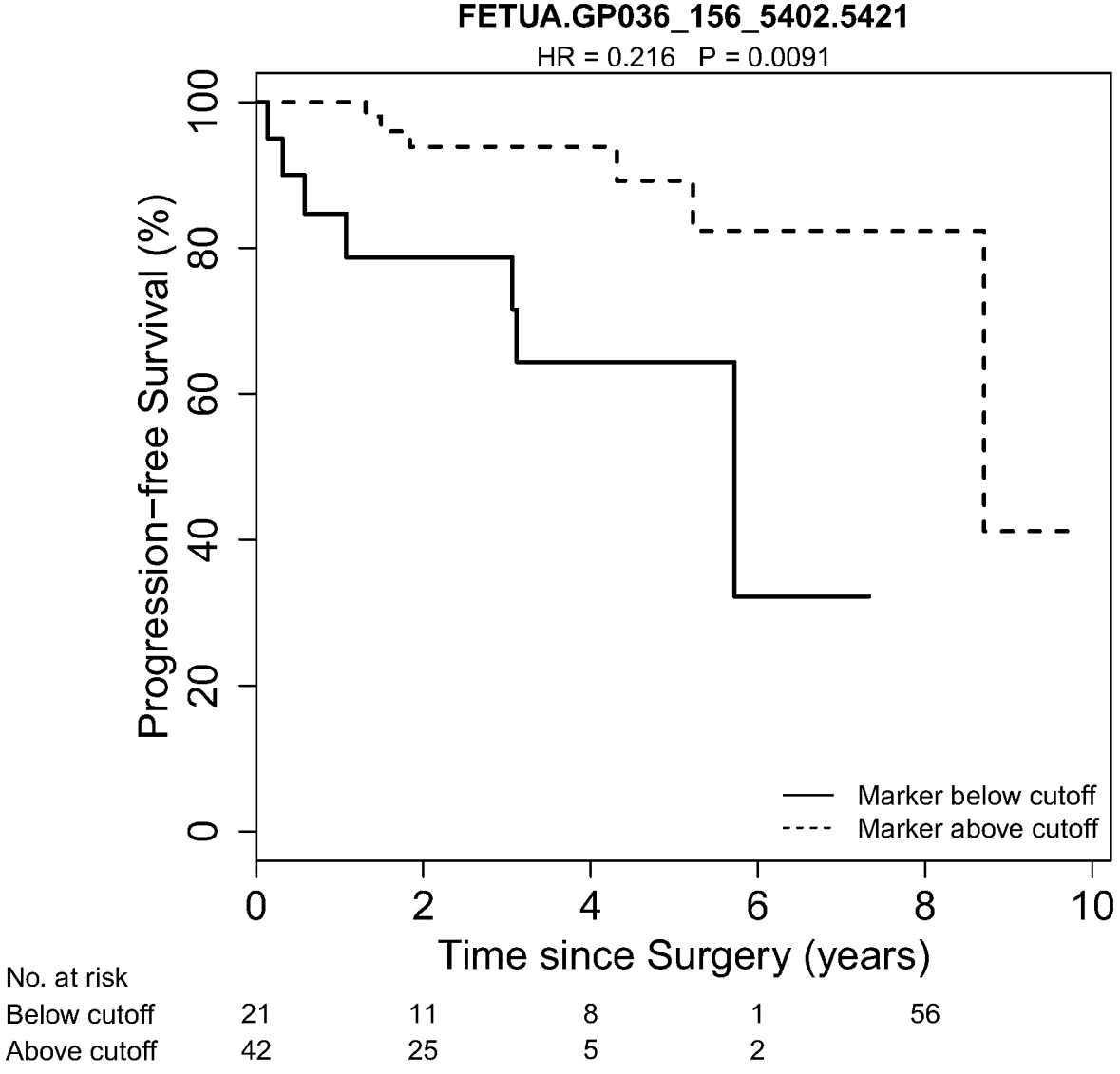
Figure 25:
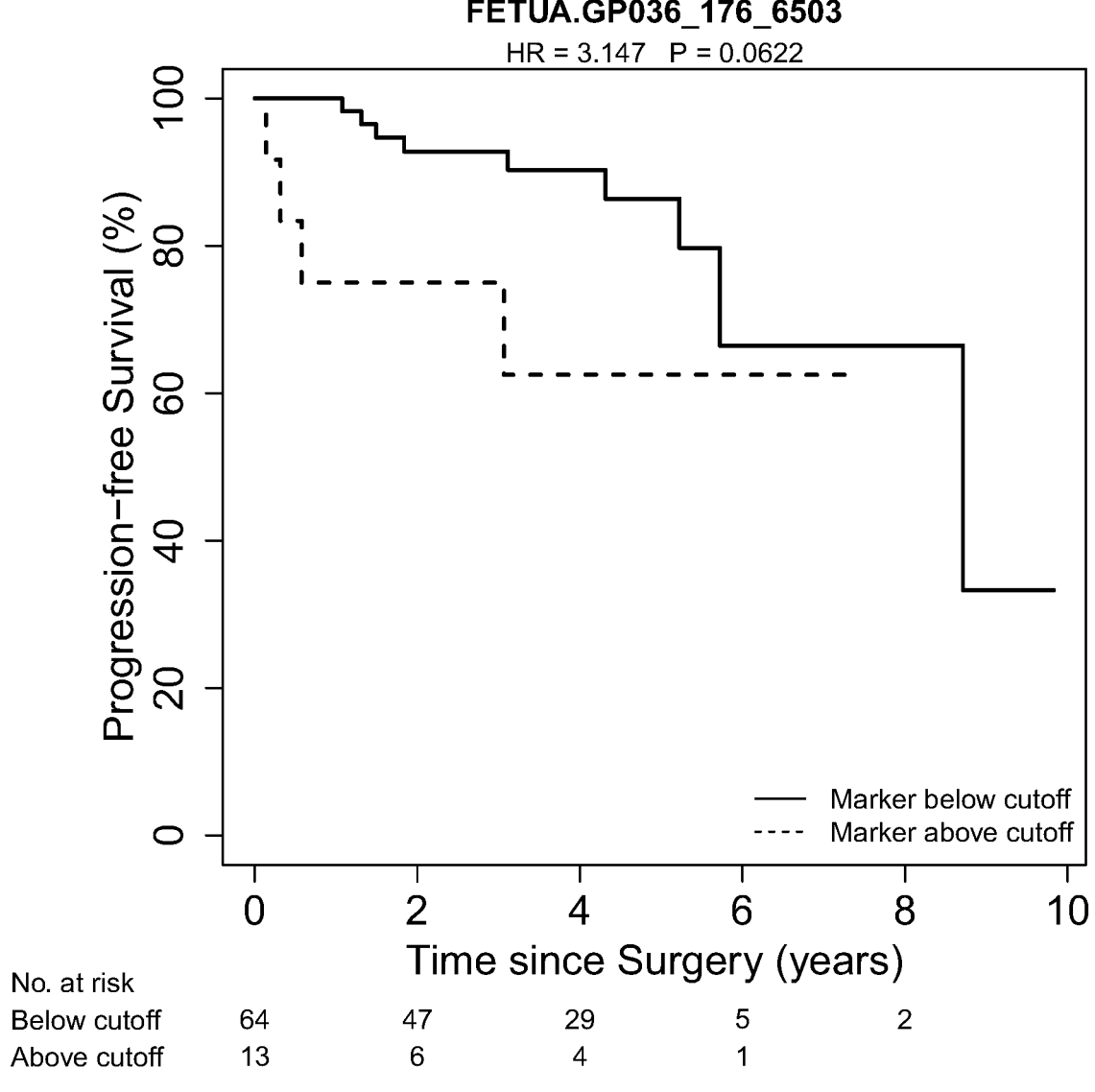
Figure 26:
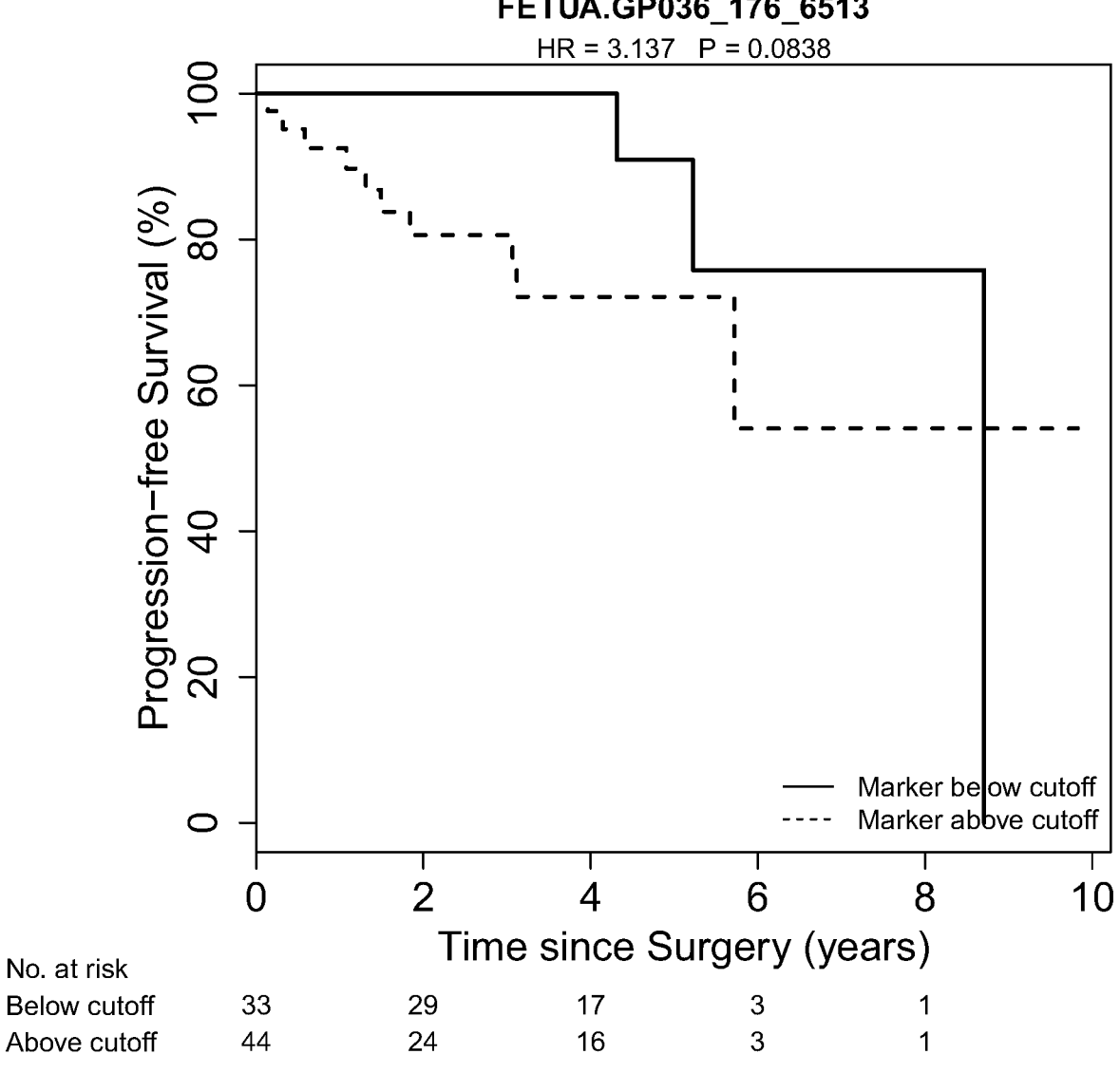
Figure 27:
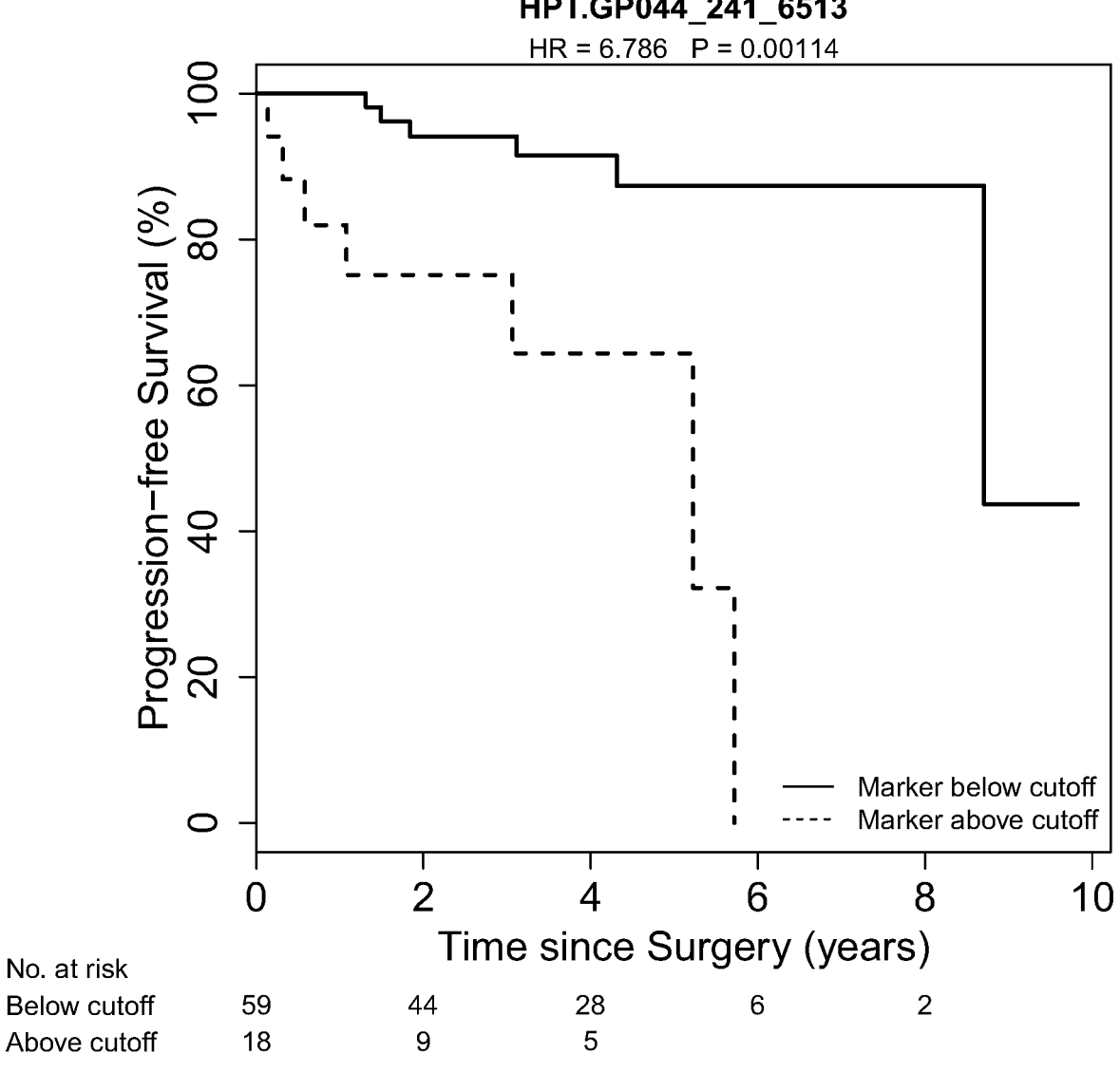
Figure 28:
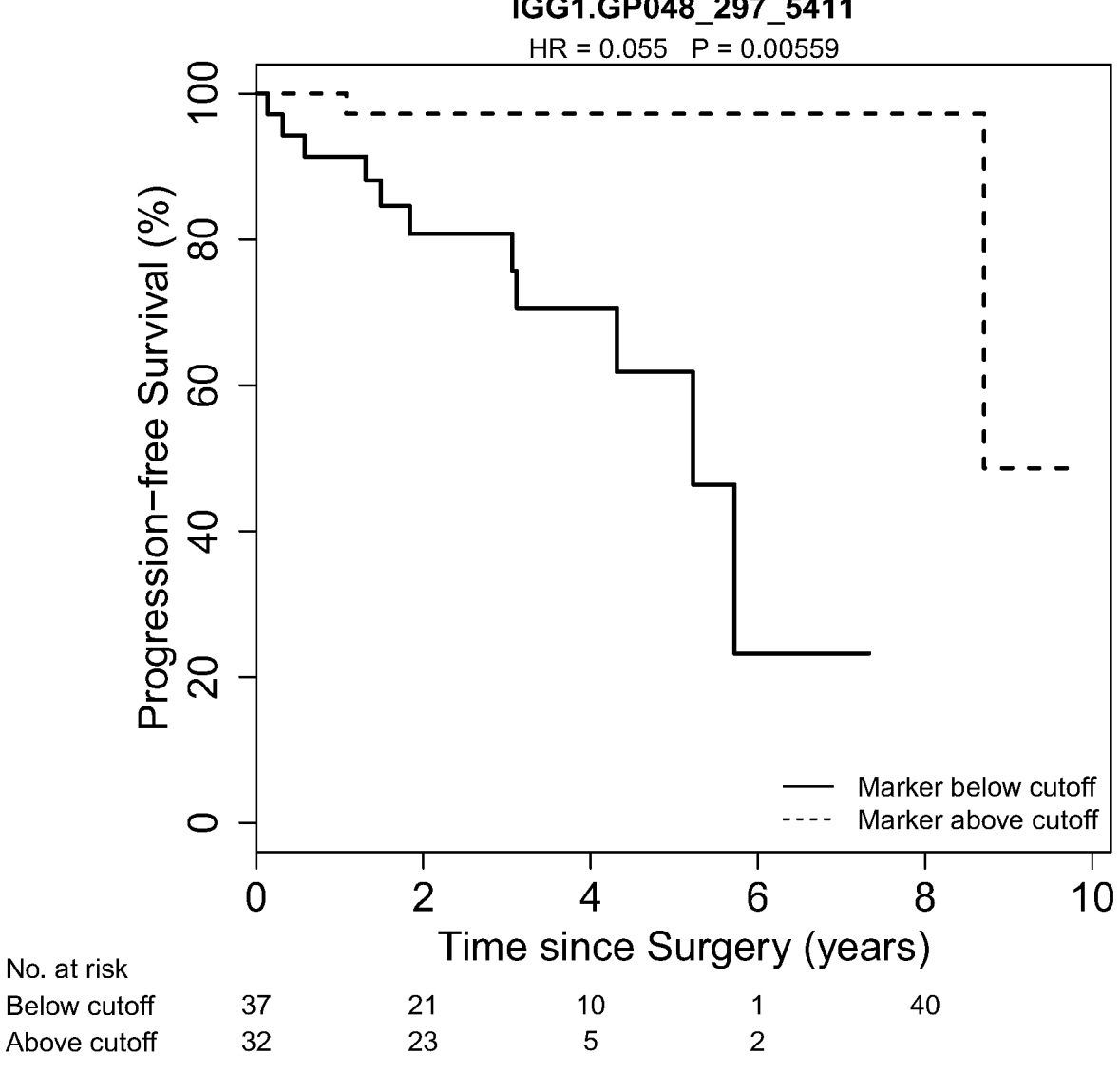
Figure 29:
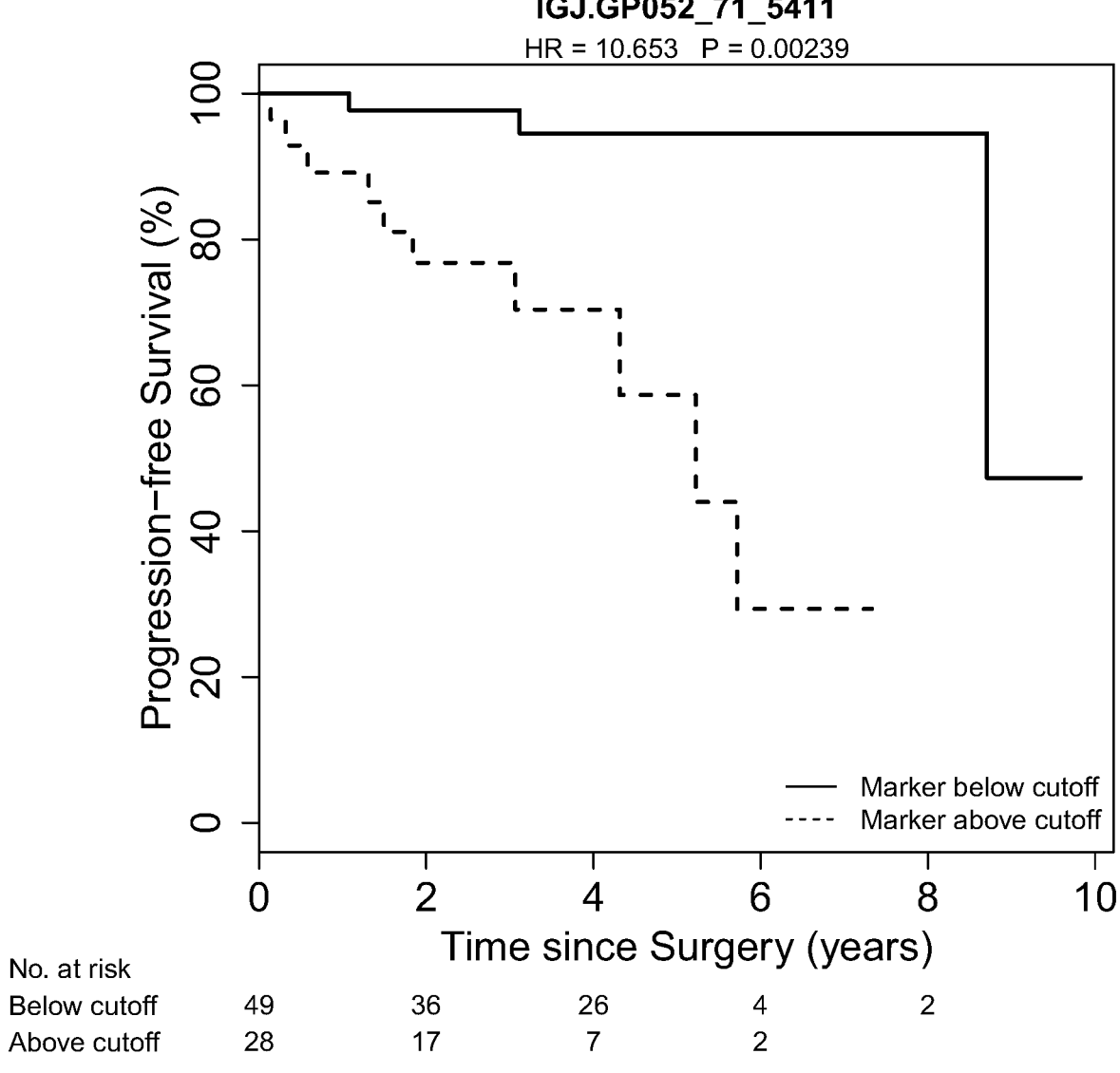
Figure 30:
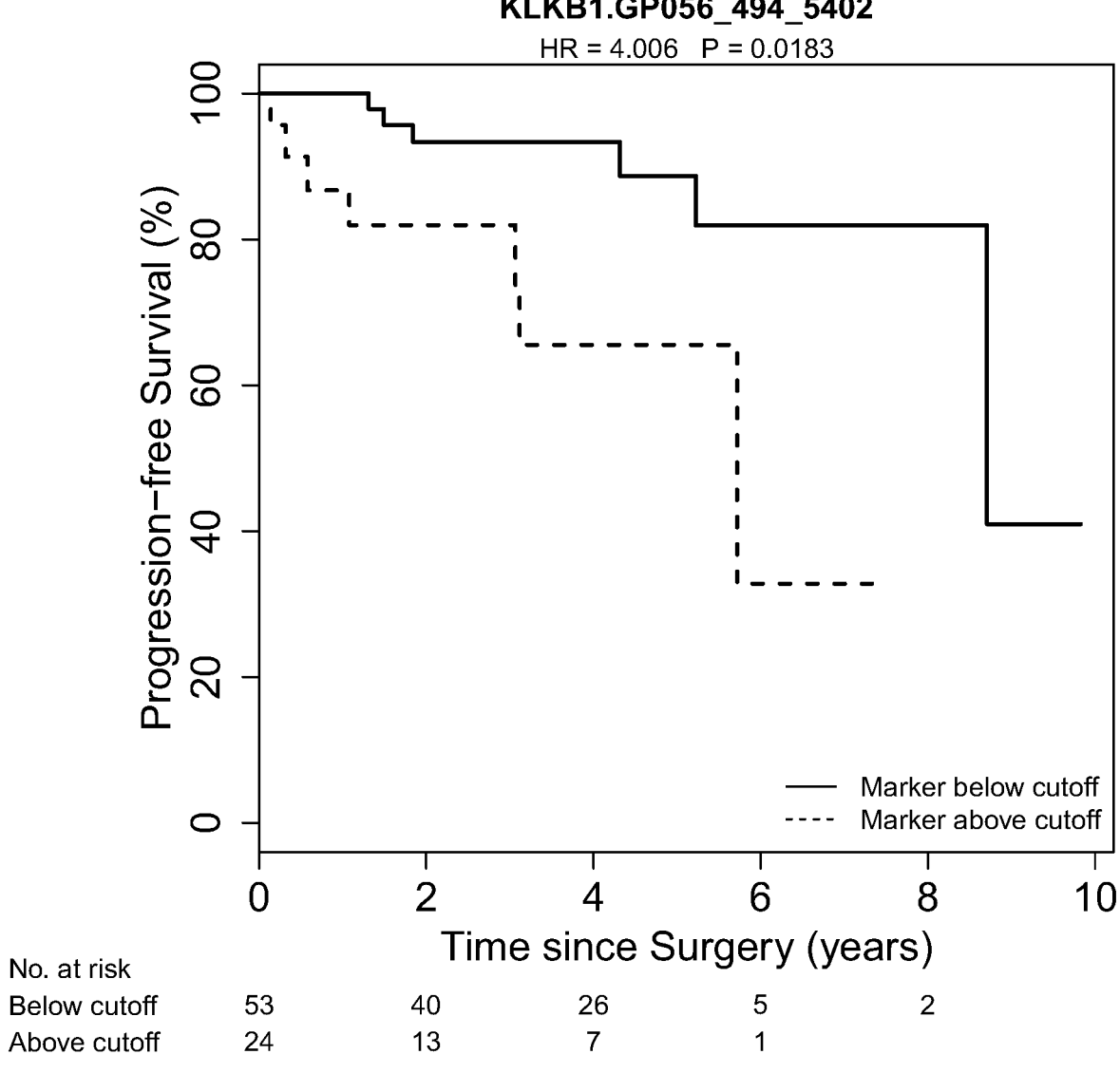
Figure 31:
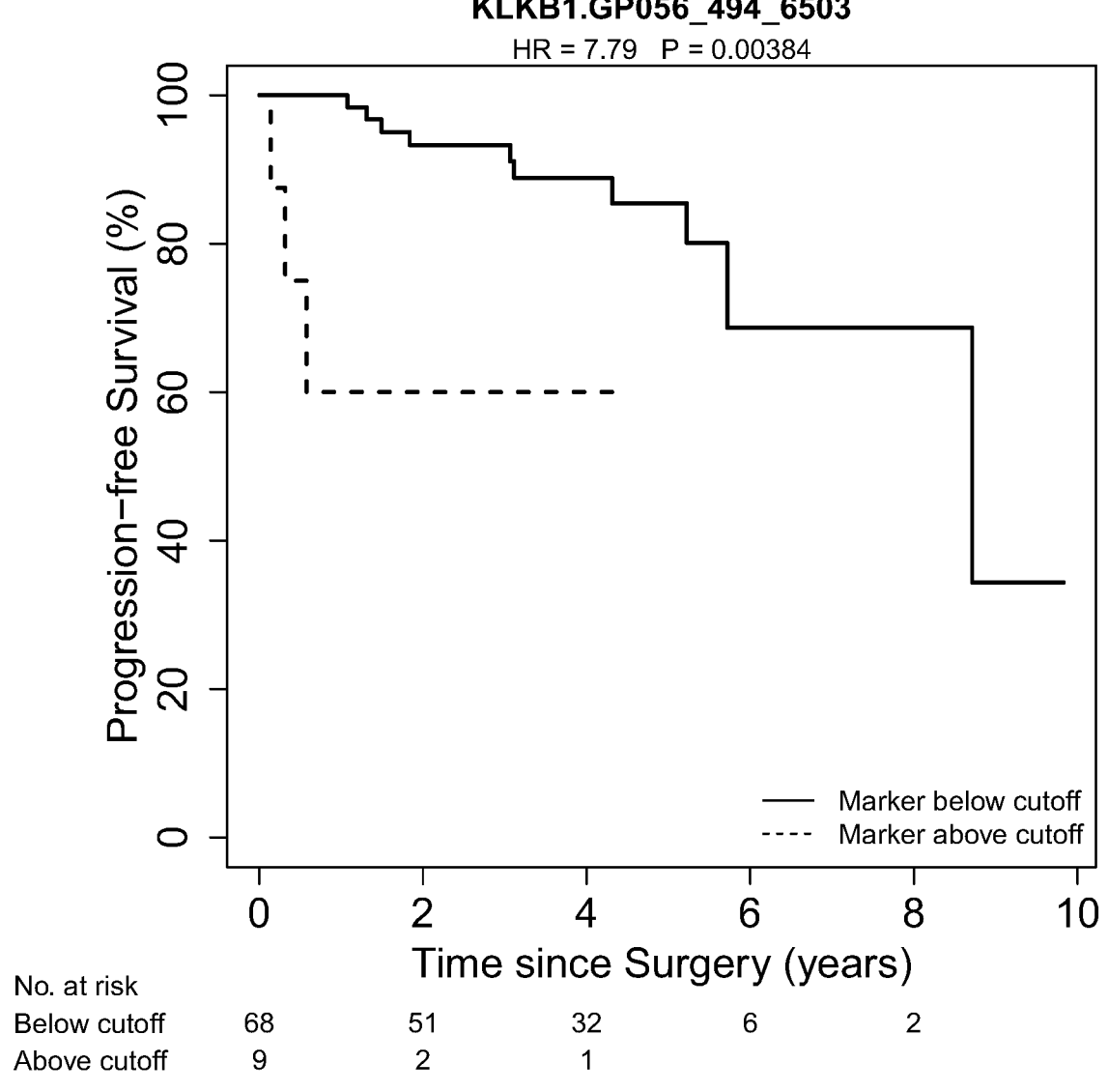
Figure 32:
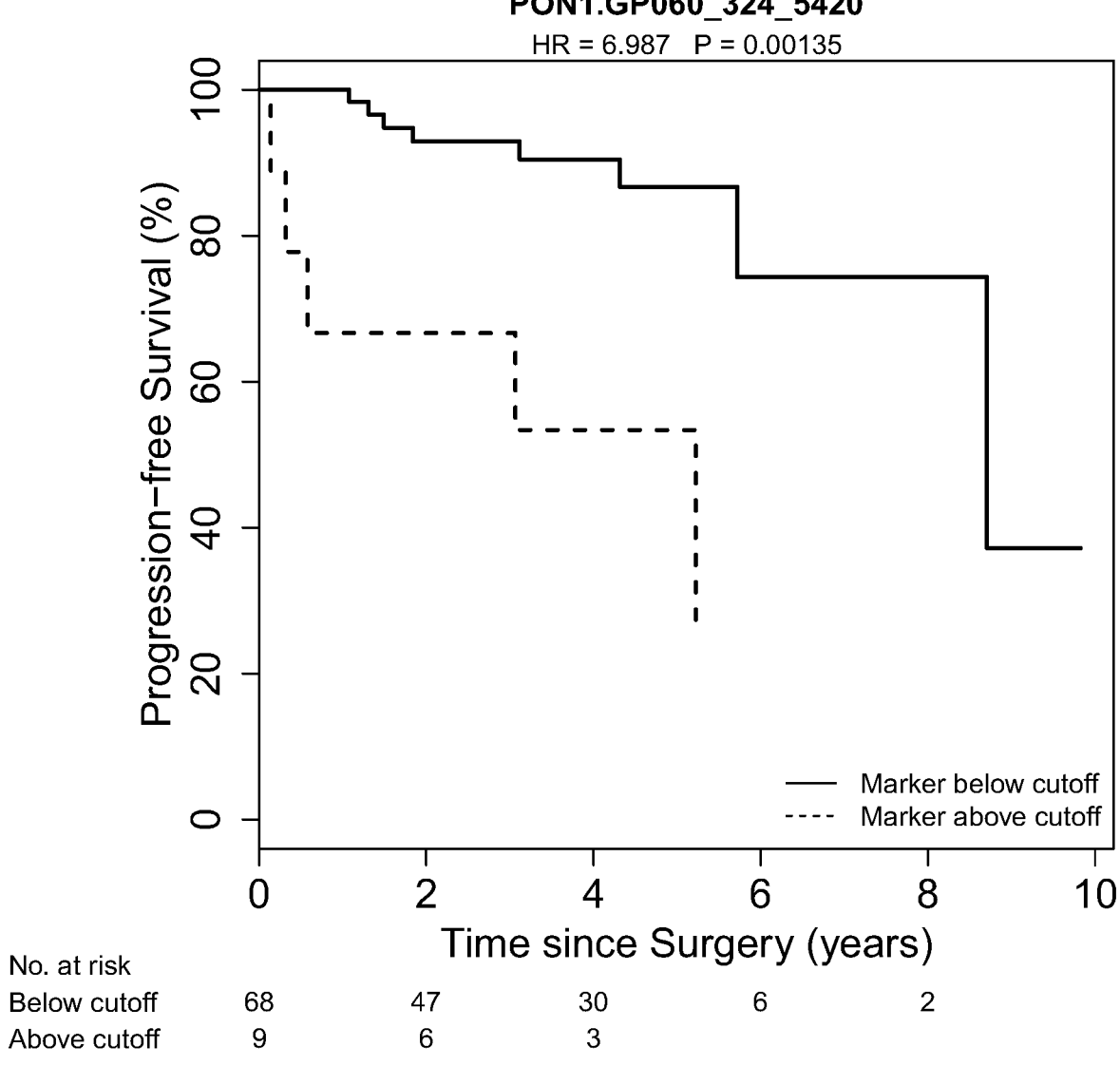
Figure 33:
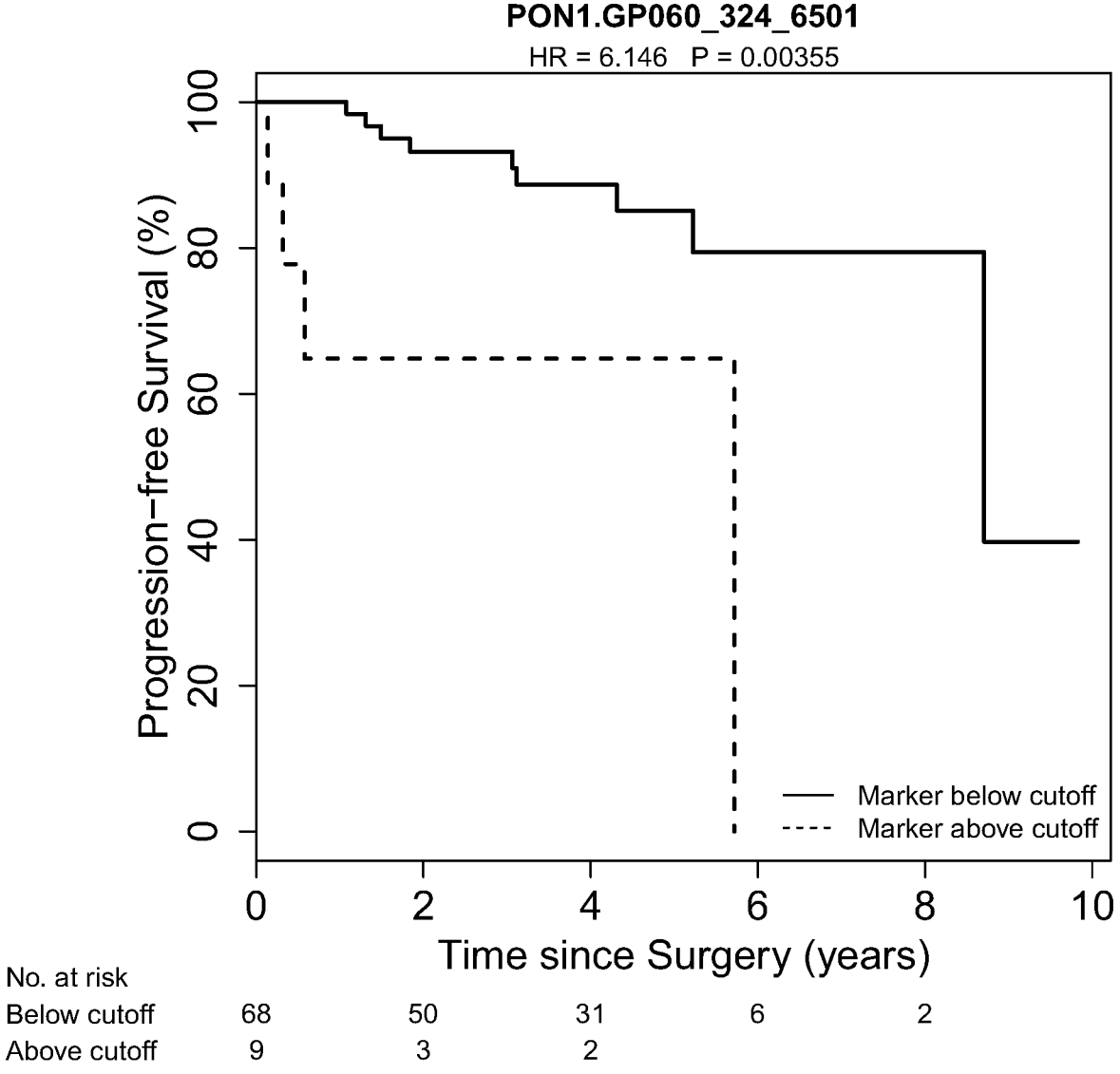
Figure 34:
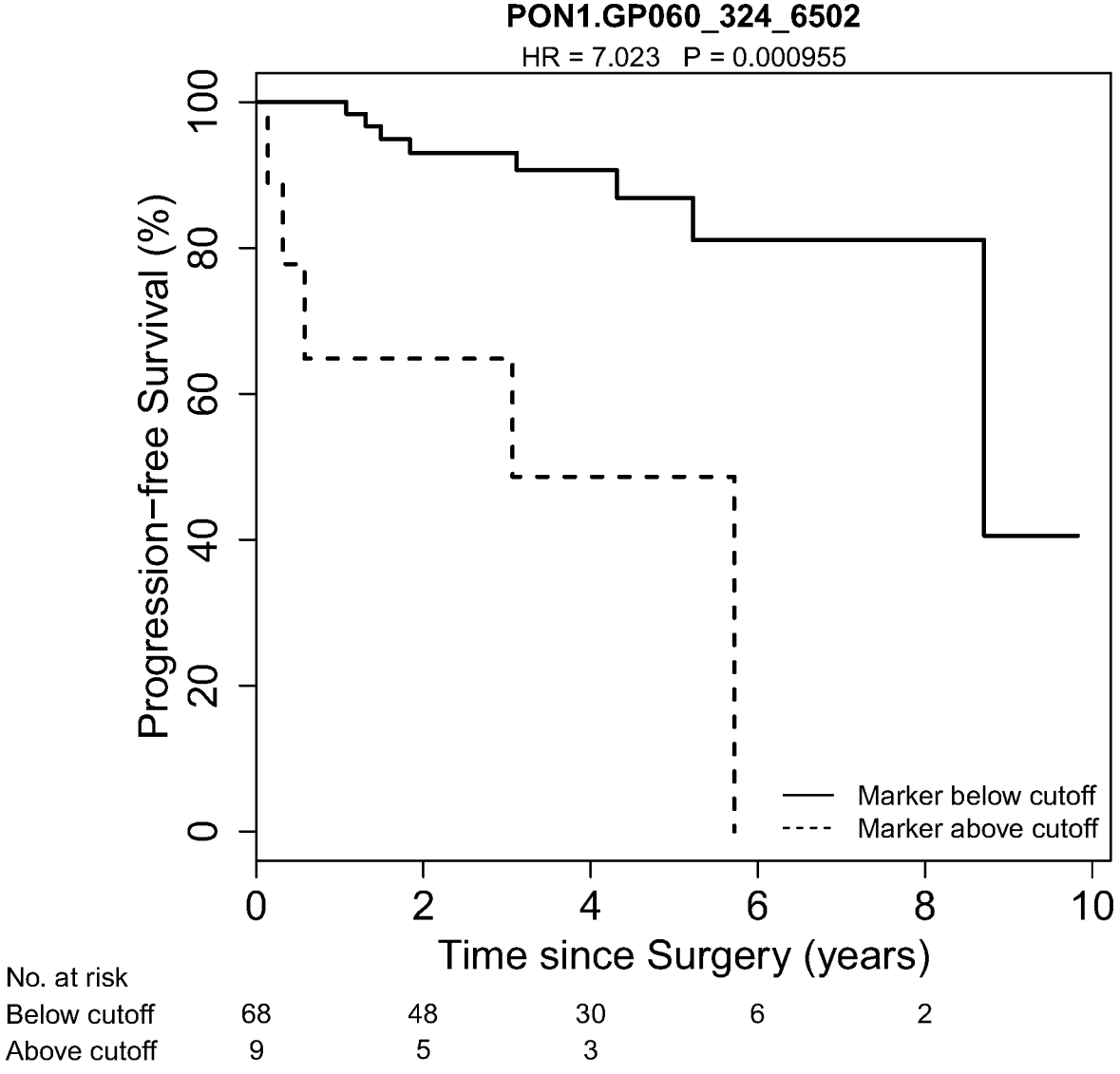
Figure 35:
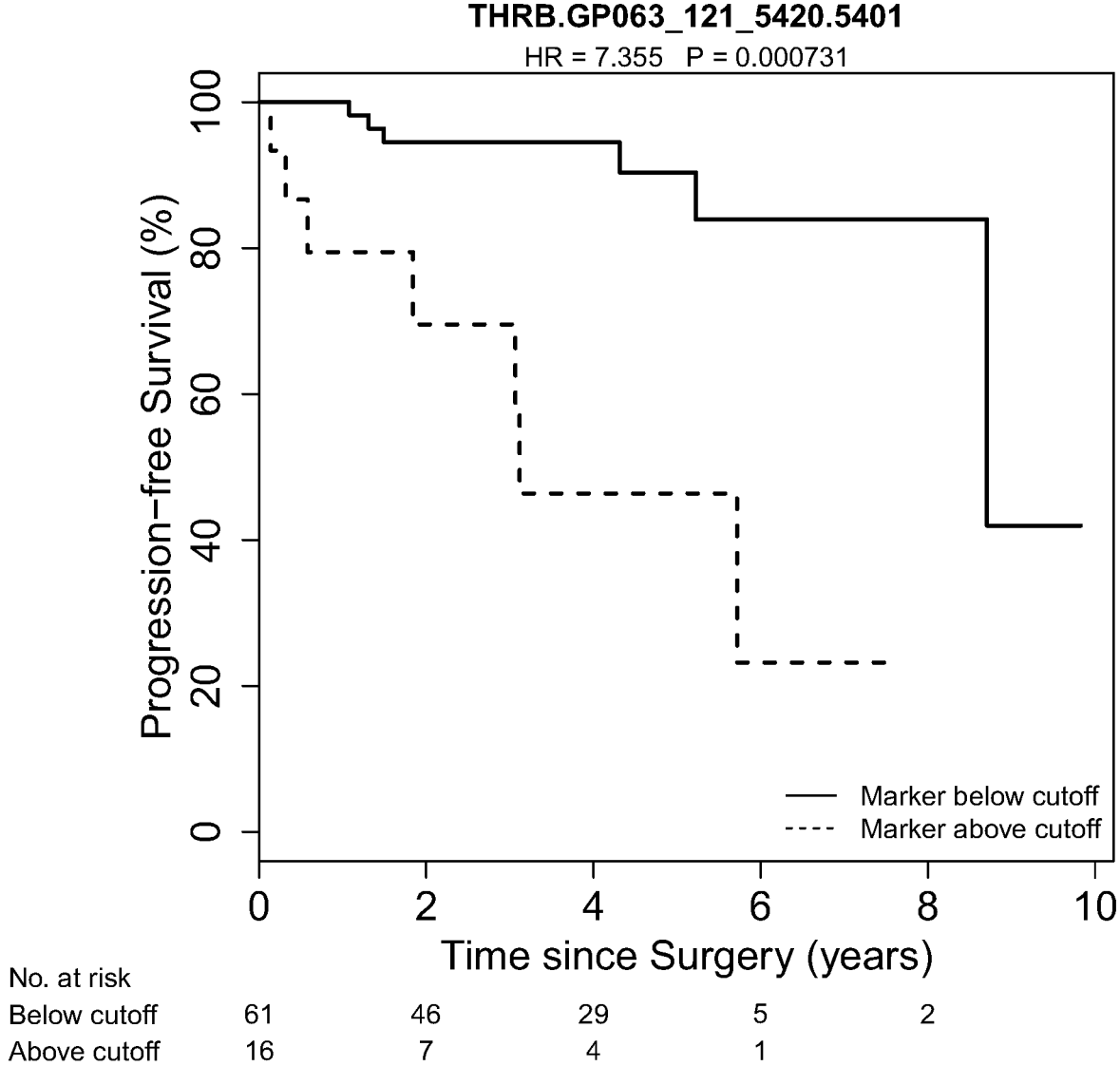
Figure 36:
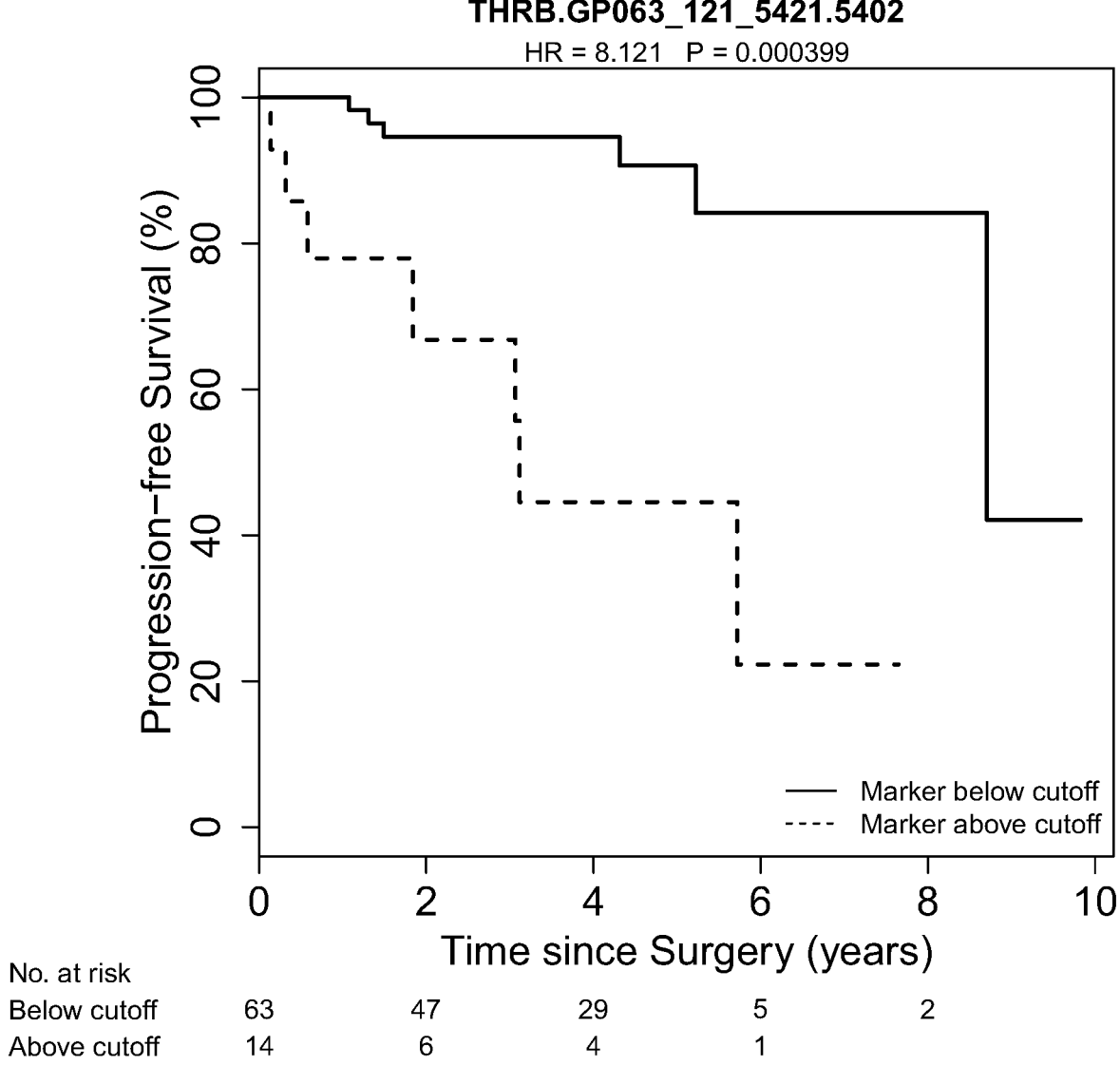
Figure 37:
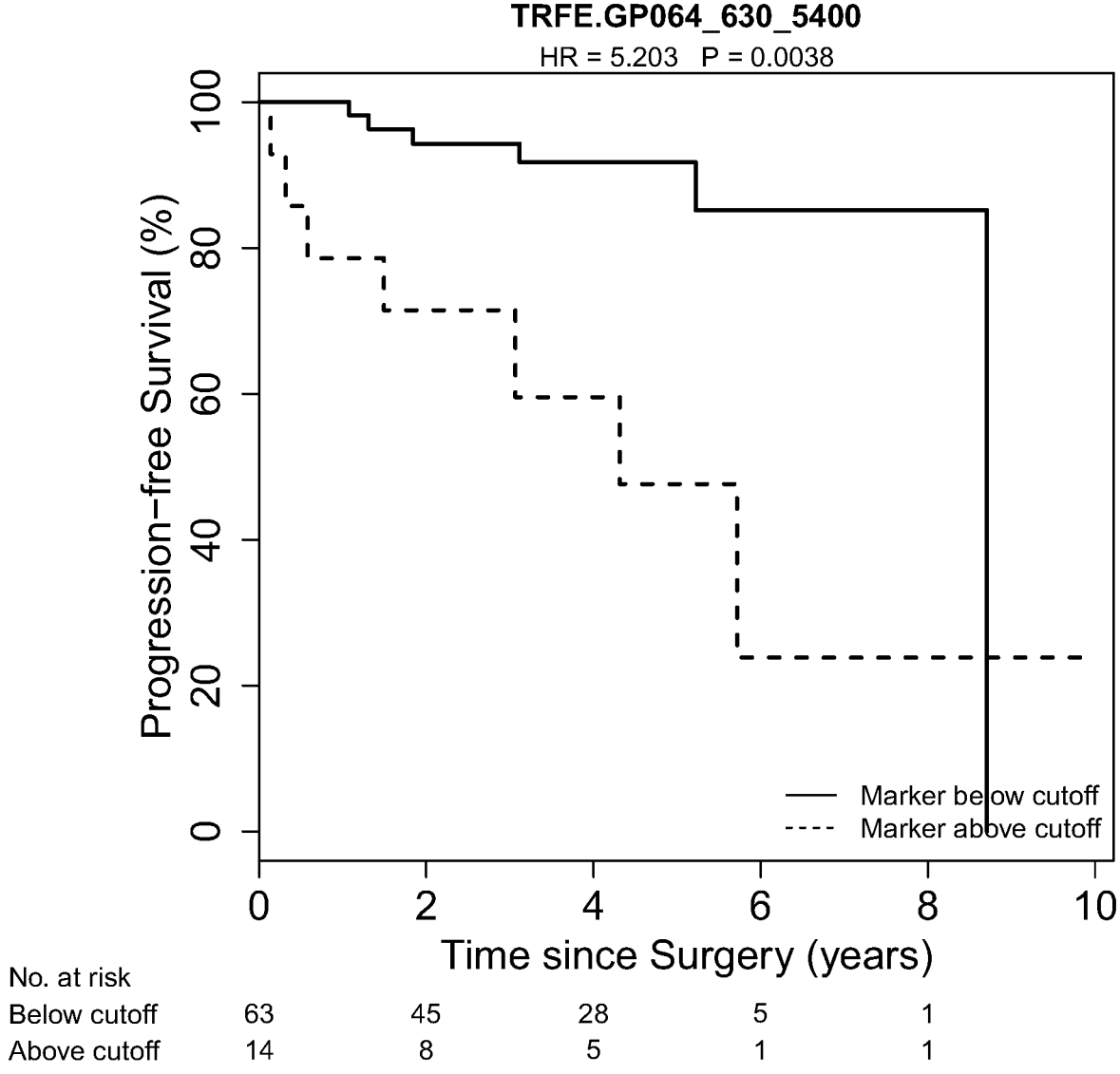
Figure 38:
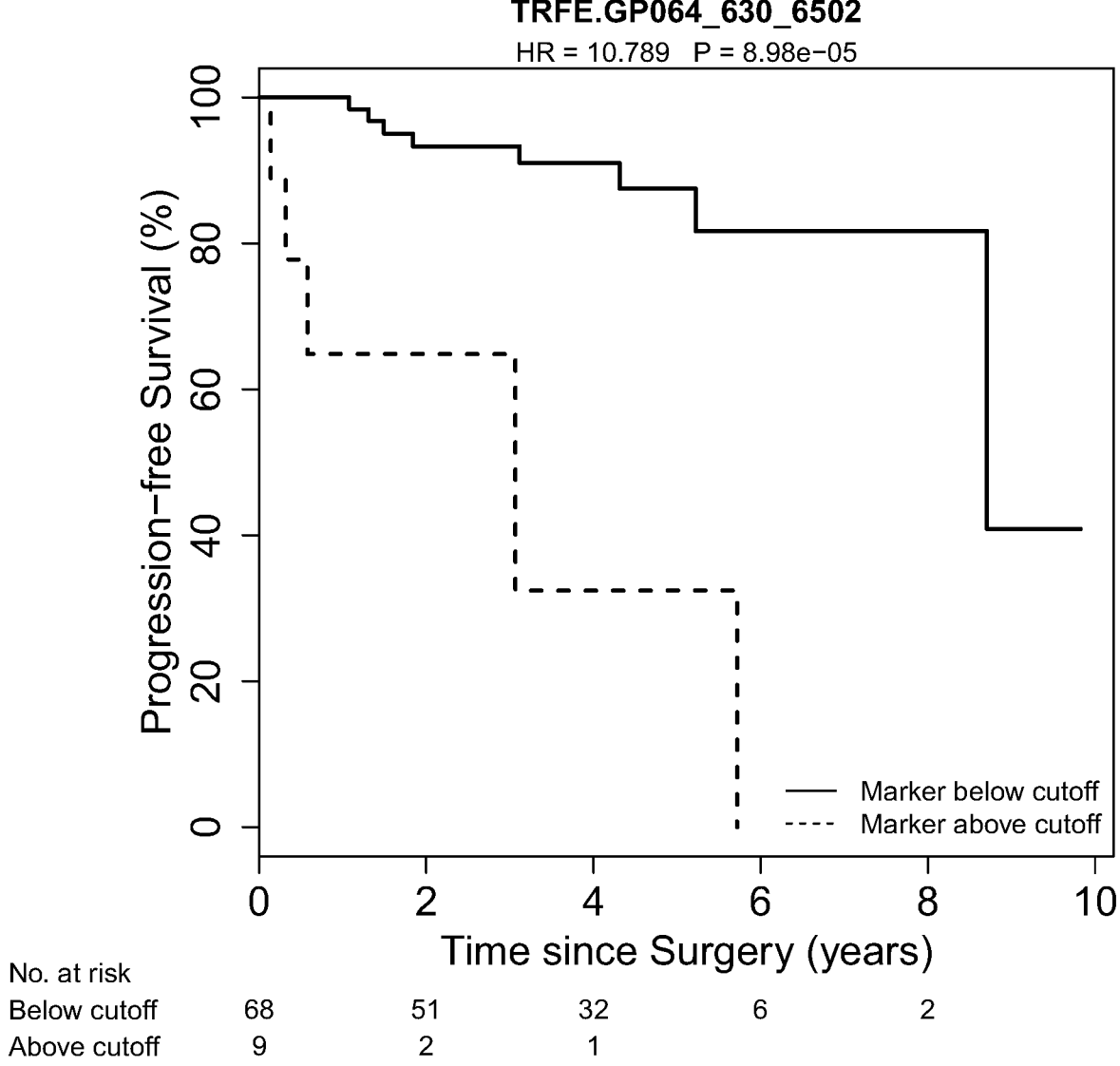
Figure 39:
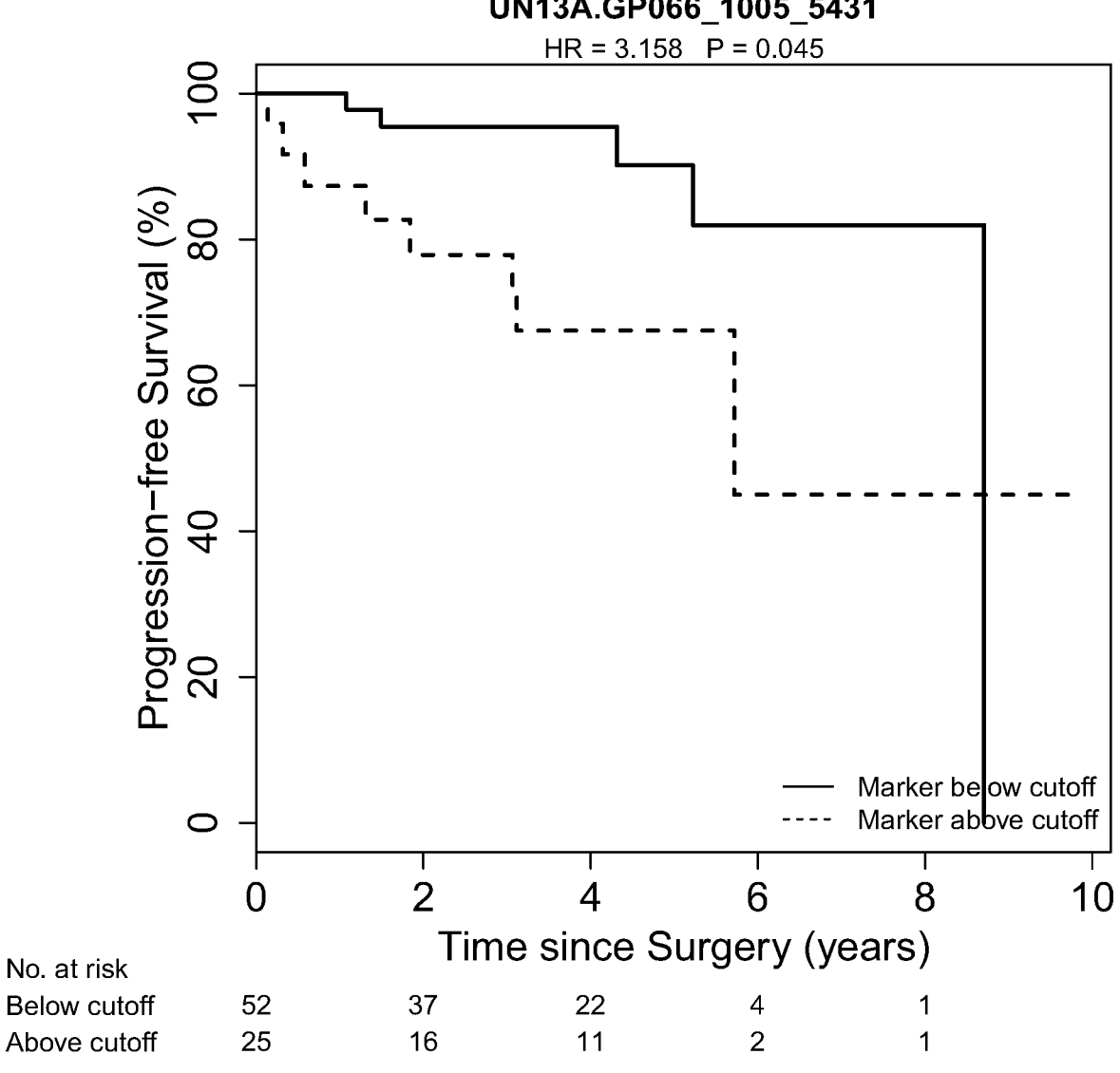
Figure 40:
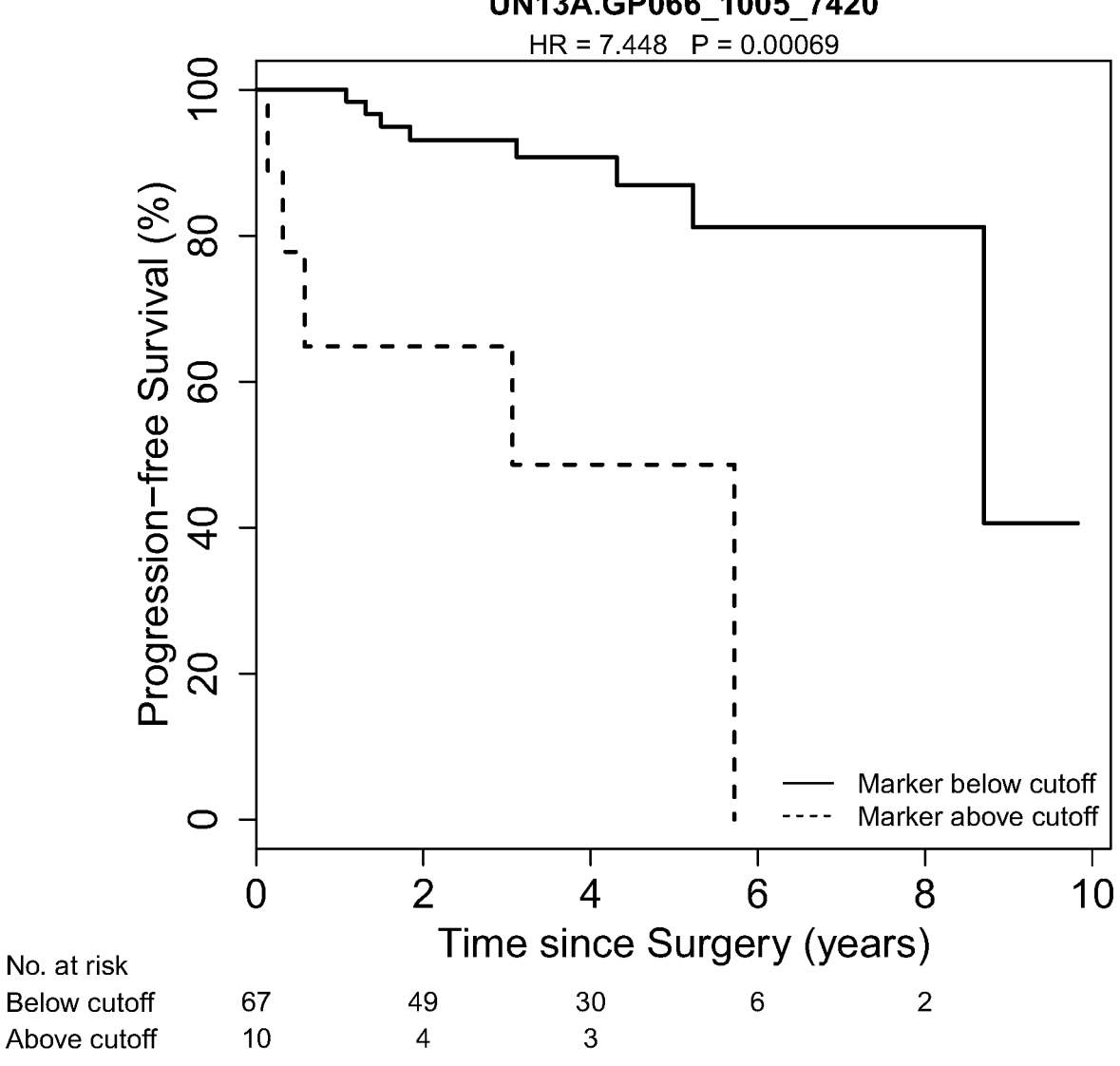
Figure 41:
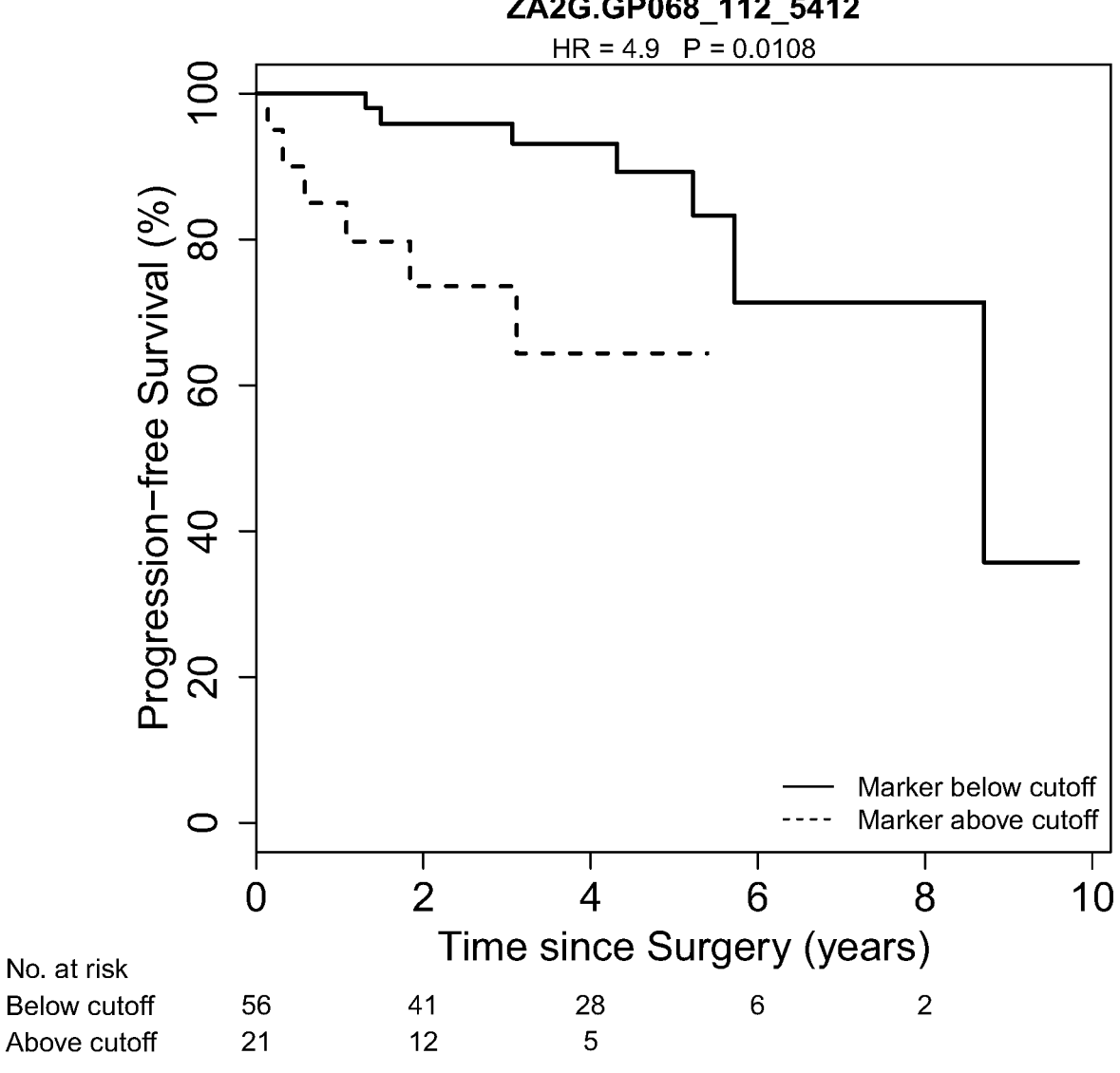

In FIG. 2, the solid line represents samples from patients having Stage 1 or Stage 2 ccRCC which includes 0-9 of the biomarker glycopeptides set forth in SEQ ID Nos.: 1-39. This patient would be considered as likely having less aggressive disease.

In FIG. 2, the dashed line represents samples from patients having Stage 1 or Stage 2 ccRCC which includes 10 or more of the biomarker glycopeptides set forth in SEQ ID Nos.: 1-39. This patient would be considered as likely having more aggressive disease.

A multivariable score for each patient was generated by summing the number of individual markers that were above the selected cutoffs, which is identified in FIGS. 3-41. Patients with 10 or more markers above those cutoffs were considered as having a glycosylation signature indicative of likely more aggressive disease and predisposed to increased risk of metastasis or death due to disease.

This "Tally" score is shown in FIG. 1 across all patients, and in FIG. 2 only for stage 1 and 2 patients for whom the prognosis would ordinarily have been considered good.

These metrics are then used in determining the course of treatment and surveillance for a patient's disease. For example, when patients with stage 1 or 2 cancer have a high Tally score, they are categorized as likely having more aggressive disease and then more frequently scanned (or checked medically) for disease progression. For example, whereas a patient with stage 1 or 2 cancer and a low Tally score would need to be seen by medical professionals yearly, a patient with stage 1 or 2 cancer and a high Tally score would need to be seen by medical professionals quarterly. Also, for example, when patients with stage 1 or 2 cancer also have a low tally score, they are categorized as likely having less aggressive disease and should need less frequent scanning (or checking medically) for disease progression. Patients with a high tally score would likely be considered candidates for new treatments or clinical trials of new therapeutics aimed at more aggressive forms of RCC to test their efficacy. Appropriately categorizing RCC patients with stage 1 or 2 cancer, as either likely to having more or less aggressive disease using the biomarkers set forth herein, results in significant improvements of overall medical outcome (e.g. progression-free survival, or survival), quality-of-life (e.g. potential; avoidance of aggressive treatments with severe adverse effects in patients with a low Tally score) for the patient, and health economic benefits for both the patient and the health care system.

Example 2

In this example, high-throughput proteomics were employed to evaluate expression of glycosylated peptides as novel markers for ccRCC PFS.

Methods: Plasma samples from newly diagnosed ccRCC were obtained from an established RCC tissue registry prior to their nephrectomy. Glycoproteomic analysis and identification was completed with Liquid Chromatography with tandem mass spectrometry (LC-MS/MS). Age-adjusted, Cox proportional hazard models were constructed to observe the association between glycopeptides and progression free survival (PFS). The cutoff which optimized Harrell's c-index was employed to dichotomize expression for PFS Kaplan-Meier curves.

Plasma samples of 77 ccRCC patients were analyzed: 48(62%) patients were male and 29 patients were female ($^{38}$%). The mean age was 61 years (range: 33-79 years). Of the patients, 54 were stage I (70%), 9 were stage II (11.7%), 12 were stage III (15.6%), one was stage IV (1.3%), and for one staging information was missing. The average length of follow-up was 3.4 (range: 0.04-9.83) years. A total of 13 patients had recurrent disease.

The glycoproteomic analysis herein identified 53 markers with false discovery rate less than 0.05, including 39 glycosylated peptides. See SEQ ID NOs: 1-39. Five of these glycosylated peptides had a continuous hazard ratio >6 (range 6.3-11.6). These included G2S glycan motif from Prothrombin (HR=6.47, P=9.53E-05), G2SF motif from Immunoglobulin J Chain (HR=10.69, P=0.001), Man5 motif from Clusterin (HR=7.37, P=0.002), G2S2 motif from Complement Component C8A (HR=11.59, P=0.002), and an undecorated hybrid-type glycan from Apolipoprotein M (HR=6.30, P=0.003). See SEQ ID NOs: 15, 19, 21, 27, and 33. Kaplan-Meier curves based on dichotomous expression of these five glycopeptides resulted in hazard ratios from 3.9-10.7, all with p-value <0.03.

This Example demonstrates that glycosylated peptides are biomarkers for ccRCC PFS.

Example 3

In this example, existing and internally developed bi-directional recurrent neural networks (RNNs) were employed in service of quantifying glycopeptide abundance from the raw output of a targeted mass spectrometry experiment done on a triple-quadrupole (QQQ).

Raw files were obtained for each sample run through the LC/MS, and uploaded to the relevant cloud storage location. The raw files were then processed by a data pipeline that first converts the vendor format to an open source format (mzML) via msconvert. Targeted quantification windows (matching the scheduled dMRM targets) were input into the peak integration software in the form of a series of Q1 m/z ratios, Q3, m/z ratios, and the windows of retention time (RT) over which each molecule elutes through the LC. These parameters define the selection of sequential intensities to be considered for integration.

Over this specified input window, the RNN determined where the peak begins and ends, subtracts baseline noise, and integrates the remaining peak area. These integrated values represented the molecular abundance of the targets, and were utilized in downstream analysis for determining disease prognosis and other precision medicine endpoints The RNN was trained on a very large, internal set of chromatographic peaks for which the beginning and end of the peaks were annotated manually. With the problem specified in this way, the RNN comes closer and closer to predicting the human-labeled truth over the many epochs of training necessary for deep neural networks. The RNN described has over 99% concordance with human labels in targets not utilized during training. See the methods in U.S. Provisional Patent Application No. 62/826,228, filed Mar. 29, 2019, and titled AUTOMATED DETECTION OF BOUNDARIES IN MASS SPECTROMETY DATA, the entire contents of which are herein incorporated by reference in its entirety for all purposes.

Tables

TABLE 3-continued

Transition Numbers with Precursor Ion and Product Ion (m/z)

| Transition No. | Precursor Ion | Product Ion |
|---|---|---|
| 13 | 1335.3 | 366.1 |
| 14 | 1185.3 | 366.1 |
| 15 | 1199.7 | 366.1 |
| 16 | 1147.8 | 366.1 |
| 17 | 1199.5 | 366.1 |
| 18 | 1236.2 | 366.1 |

TABLE 2

Transition Numbers for Glycopeptides from Glycopeptide Groups.

| Transition No. | Compound Group | Compound Name |
|---|---|---|
| 1 | AACT-GP005__271__7603 | GP005-P01011Alpha-1-antichymotrypsin1AACT |
| 2 | AFAM-GP006__402__5402 | GP006-P436521Afamin1AFAM |
| 3 | AGP12-GP007&008__72MC__7614 | GP007&008-P02763&P196521Alpha-1-acid glycoprotein 1&21AGP12 |
| 4 | APOB-GP013__3411__5401 | GP013-P041141Apolipoprotein B-1001APOB |
| 5 | APOC3-GP012__74__1111 | GP012-P026561Apolipoprotein C-III1APOC3 |
| 6 | APOC3-GP012__74__1300 | GP012-P026561Apolipoprotein C-III1APOC3 |
| 7 | APOC3-GP012__74__2110 | GP012-P026561Apolipoprotein C-III1APOC3 |
| 8 | APOC3-GP012__74Aoff__1102 | GP012-P026561Apolipoprotein C-III1APOC3 |
| 9 | APOD-GP014__98__5402/5421 | GP014-P050901Apolipoprotein D1APOD |
| 10 | APOD-GP014__98__5410 | GP014-P050901Apolipoprotein D1APOD |
| 11 | APOD-GP014__98__6510 | GP014-P050901Apolipoprotein D1APOD |
| 12 | APOD-GP014__98__6530 | GP014-P050901Apolipoprotein D1APOD |
| 13 | APOD-GP014__98__9800 | GP014-P050901Apolipoprotein D1APOD |
| 14 | APOM-GP016__135__5421 | GP016-O954451Apolipoprotein M1APOM |
| 15 | APOM-GP016__135__8500 | GP016-O954451Apolipoprotein M1APOM |
| 16 | C1S-GP020__174__5402 | GP020-P098711Complement C1s subcomponent1C1S |
| 17 | CAN3-GP022__366__6503 | GP022-P208071Calpain-31CAN3 |
| 18 | CAN3-GP022__366__6513 | GP022-P208071Calpain-31CAN3 |
| 19 | CLUS-GP026__291__5400 | GP026-P109091Clusterin1CLUS |
| 20 | CLUS-GP026__291__6503 | GP026-P109091Clusterin1CLUS |
| 21 | CO8A-GP033__437__5402 | GP033-P073571ComplementComponentC8AChain1CO8A |
| 22 | FETUA-GP036__156__5402/5421 | GP036-P027651Alpha-2-HS-glycoprotein1FETUA |
| 23 | FETUA-GP036__176__6503 | GP036-P027651Alpha-2-HS-glycoprotein1FETUA |
| 24 | FETUA-GP036__176__6513 | GP036-P027651Alpha-2-HS-glycoprotein1FETUA |
| 25 | HPT-GP044__241__6513 | GP044-P007381Haptoglobin1HPT |
| 26 | IgG1-GP048__297__5411 | GP048-P018571Immunoglobulin heavy constant gamma 11IgG1 |
| 27 | IgJ-GP052__71__5411 | GP052-P015911Immunoglobulin J chain1Ig-J |
| 28 | KLKB1-GP056__494__5402 | GP056-P039521Plasma Kallikrein1KLKB1 |
| 29 | KLKB1-GP056__494__6503 | GP056-P039521Plasma Kallikrein1KLKB1 |
| 30 | PON1-GP060__324__5420 | GP060-P271691Serum paraoxonase/arylesterase 11PON1 |
| 31 | PON1-GP060__324__6501 | GP060-P271691Serum paraoxonase/arylesterase 11PON1 |
| 32 | PON1-GP060__324__6502 | GP060-P271691Serum paraoxonase/arylesterase 11PON1 |
| 33 | THRB-GP063__121__5420/5401 | GP063-P007341Prothrombin1THRB |
| 34 | THRB-GP063__121__5421/5402 | GP063-P007341Prothrombin1THRB |
| 35 | TRFE-GP064__630__5400 | GP064-P027871Serotransferrin1TRFE |
| 36 | TRFE-GP064__630__6502 | GP064-P027871Serotransferrin1TRFE |
| 37 | UN13A-GP066__1005__5431 | GP066-Q9UPW81Protein unc-13HomologA1UN13A |
| 39 | UN13A-GP066__1005__7420 | GP066-Q9UPW81Protein unc-13HomologA1UN13A |
| 39 | ZA2G-GP068__112__5412 | GP068-P253111Zinc-alpha-2-glycoprotein1ZA2G |

TABLE 3

Transition Numbers with Precursor Ion and Product Ion (m/z)

| Transition No. | Precursor Ion | Product Ion |
|---|---|---|
| 1 | 1245.8 | 366.1 |
| 2 | 1227.2 | 366.1 |
| 3 | 1313.1 | 366.1 |
| 4 | 1174.2 | 366.1 |
| 5 | 980.4 | 274.1 |
| 6 | 970.1 | 366.1 |
| 7 | 937.4 | 366.1 |
| 8 | 1005.1 | 274.1 |
| 9 | 1115.7 | 366.1 |
| 10 | 1341.6 | 366.1 |
| 11 | 1098 | 366.1 |
| 12 | 1171 | 366.1 |

TABLE 3-continued

Transition Numbers with Precursor Ion and Product Ion (m/z)

| Transition No. | Precursor Ion | Product Ion |
|---|---|---|
| 19 | 856.3 | 366.1 |
| 20 | 952.1 | 366.1 |
| 21 | 1180.1 | 366.1 |
| 22 | 995.1 | 366.1 |
| 23 | 1307.1 | 366.1 |
| 24 | 1343.8 | 366.1 |
| 25 | 1201.5 | 366.1 |
| 26 | 1083.8 | 366.1 |
| 27 | 1096.8 | 366.1 |
| 28 | 1114.7 | 366.1 |
| 29 | 1277.8 | 366.1 |
| 30 | 1057.7 | 366.1 |

TABLE 3-continued

Transition Numbers with Precursor Ion and Product Ion (m/z)

| Transition No. | Precursor Ion | Product Ion |
|---|---|---|
| 31 | 1149.3 | 366.1 |
| 32 | 1221.5 | 366.1 |
| 33 | 904.4 | 366.1 |
| 34 | 1001.4 | 366.1 |
| 35 | 1035.6 | 366.1 |
| 36 | 1018.1 | 366.1 |
| 37 | 1227.5 | 366.1 |
| 39 | 1199.2 | 366.1 |
| 39 | 1472.6 | 366.1 |

Fragmentor setting is 380V, and the cell accelerator voltage is 5

MSI and MS2 resolution was <1 unit.

TABLE 4

Transition Numbers with Retention Time, ΔRetention Time, & Collision Energy

| Transition No. | Ret Time (min) | Delta Ret Time | Collision Energy |
|---|---|---|---|
| 1 | 19.7 | 1.2 | 35 |
| 2 | 16.8 | 1.2 | 30 |
| 3 | 39.4 | 3 | 27 |
| 4 | 10.9 | 1.2 | 30 |
| 5 | 29.9 | 1.6 | 24 |
| 6 | 29.4 | 1.6 | 23 |
| 7 | 29.1 | 1.6 | 22 |
| 8 | 30 | 2 | 24 |
| 9 | 21.8 | 1.2 | 34 |
| 10 | 21.8 | 1.2 | 35 |
| 11 | 21.5 | 1.2 | 34 |
| 12 | 22.2 | 1.2 | 35 |
| 13 | 21.8 | 1.2 | 39 |
| 14 | 26.4 | 2 | 36 |
| 15 | 26.7 | 2 | 36 |
| 16 | 25.2 | 2 | 30 |
| 17 | 25.2 | 2 | 36 |
| 18 | 24.3 | 2 | 37 |
| 19 | 3.4 | 1.2 | 25 |
| 20 | 3.7 | 1.2 | 30 |
| 21 | 11.2 | 1.2 | 36 |
| 22 | 20.1 | 1.2 | 24 |
| 23 | 22 | 1.2 | 33 |
| 24 | 22 | 1.2 | 34 |
| 25 | 22.2 | 1.2 | 30 |
| 26 | 6 | 1 | 27 |
| 27 | 12.5 | 1 | 25 |
| 28 | 19.5 | 1.2 | 34 |
| 29 | 20.8 | 1.2 | 38 |
| 30 | 25.3 | 2 | 33 |
| 31 | 25.2 | 2 | 35 |
| 32 | 24.9 | 2 | 37 |
| 33 | 3.1 | 1.2 | 29 |
| 34 | 3.1 | 1.2 | 31 |
| 35 | 22 | 1.2 | 25 |

TABLE 4-continued

Transition Numbers with Retention Time, ΔRetention Time, & Collision Energy

| Transition No. | Ret Time (min) | Delta Ret Time | Collision Energy |
|---|---|---|---|
| 36 | 23.3 | 1.6 | 25 |
| 37 | 24.3 | 2 | 37 |
| 39 | 25.9 | 2 | 36 |
| 39 | 19.6 | 1.2 | 43 |

Cell accelerator voltage was 5.

TABLE 5

Glycopeptide Mass, Glycan Residue, and Glycosylation Site

| Transition No. | mass | Glycoform Code | Glycosylation Site |
|---|---|---|---|
| 1 | 4978.0052 | 7603 | 271 |
| 2 | 3678.4347 | 5402 | 402-MC |
| 3 | 6557.7345 | 7614 | 72 |
| 4 | 3519.4768 | 5401 | 3411 |
| 5 | 2938.3018 | 1111 | 74 |
| 6 | 2907.3073 | 1300 | 74 |
| 7 | 2809.2592 | 2110 | 74 |
| 8 | 3012.3022 | 1102 | 74-Aoff |
| 9 | 4457.8848 | 5402 | 98 |
| 10 | 4021.7519 | 5410 | 98 |
| 11 | 4386.8841 | 6510 | 98 |
| 12 | 4678.9999 | 6530 | 98 |
| 13 | 5336.2228 | 9800 | 98 |
| 14 | 4736.9348 | 5421 | 135 |
| 15 | 4842.9614 | 8500 | 135 |
| 16 | 5730.4016 | 5402 | 174 |
| 17 | 4677.7917 | 6503 | 366 |
| 18 | 4823.8496 | 6513 | 366 |
| 19 | 2566.011 | 5400 | 291 |
| 20 | 3804.4294 | 6503 | 291 |
| 21 | 3537.3894 | 5402 | 437 |
| 22 | 3975.6117 | 5402 | 156 |
| 23 | 5225.1458 | 6503 | 176 |
| 24 | 5371.2037 | 6513 | 176 |
| 25 | 4801.0618 | 6513 | 241 |
| 26 | 3248.2396 | 5411 | 297 |
| 27 | 3287.3444 | 5411 | 71 |
| 28 | 4450.9493 | 5402 | 494 |
| 29 | 5107.1769 | 6503 | 494 |
| 30 | 4227.8826 | 5420 | 324 |
| 31 | 4591.9944 | 6501 | 324 |
| 32 | 4883.0898 | 6502 | 324 |
| 33 | 2709.1121 | 5401 | 121 |
| 34 | 3000.2075 | 5402 | 121 |
| 35 | 4136.6984 | 5400 | 630 |
| 36 | 5084.0214 | 6502 | 630 |
| 37 | 4904.956 | 5431 | 1005 |
| 39 | 4791.9083 | 7420 | 1005 |
| 39 | 4415.7804 | 5412 | 112 |

TABLE 6

Compound Group Name and Abbreviation

| Compound Group | Protein Abbreviation | Uniprot.ID |
|---|---|---|
| GP005-P0101|Alpha-1-antichymotrypsin|AACT | AACT | P01011 |
| GP006-P43652|Afamin|AFAM | AFAM | P43652 |
| GP007&008-P02763&P19652|Alpha-1-acid glycoprotein 1&2|AGP12 | AGP1 & AGP2 | P02763 & P19652 |
| GP013-P04114|Apolipoprotein B-100|APOB | APOB | P04114 |
| GP012-P02656|Apolipoprotein C-III|APOC3 | APOC3 | P02656 |
| GP012-P02656|Apolipoprotein C-III|APOC3 | APOC3 | P02656 |
| GP012-P02656|Apolipoprotein C-III|APOC3 | APOC3 | P02656 |

TABLE 6-continued

Compound Group Name and Abbreviation

| Compound Group | Protein Abbreviation | Uniprot.ID |
|---|---|---|
| GP012-P02656\|Apolipoprotein C-III\|APOC3 | APOC3 | P02656 |
| GP014-P05090\|Apolipoprotein D\|APOD | APOD | P05090 |
| GP014-P05090\|Apolipoprotein D\|APOD | APOD | P05090 |
| GP014-P05090\|Apolipoprotein D\|APOD | APOD | P05090 |
| GP014-P05090\|Apolipoprotein D\|APOD | APOD | P05090 |
| GP014-P05090\|Apolipoprotein D\|APOD | APOD | P05090 |
| GP016-O95445\|Apolipoprotein M\|APOM | APOM | O95445 |
| GP016-O95445\|Apolipoprotein M\|APOM | APOM | O95445 |
| GP020-P09871\|(Complement C1s subcomponent\|C1S | C1S | P09871 |
| GP022-P20807\|Calpain-3\|CAN3 | CAN3 | P20807 |
| GP022-P20807\|Calpain-3\|CAN3 | CAN3 | P20807 |
| GP026-P10909\|Clusterin\|CLUS | CLUS | P10909 |
| GP026-P10909\|Clusterin\|CLUS | CLUS | P10909 |
| GP033-P07357\|ComplementComponentC8AChain\|CO8A | CO8A | P07357 |
| GP036-P02765\|Alpha-2-HS-glycoprotein\|FETUA | FETUA | P02765 |
| GP036-P02765\|Alpha-2-HS-glycoprotein\|FETUA | FETUA | P02765 |
| GP036-P02765\|Alpha-2-HS-glycoprotein\|FETUA | FETUA | P02765 |
| GP044-P00738\|Haptoglobin\|HPT | HPT | P00738 |
| GP048-P01857\|Immunoglobulin heavy constant gamma 1\|IgG1 | IgG1 | P01857 |
| GP052-P01591\|Immunoglobulin J chain\|Ig-J | IgJ | P01591 |
| GP056-P03952\|Plasma Kallikrein\|KLKB1 | KLKB1 | P03952 |
| GP056-P03952\|Plasma Kallikrein\|KLKB1 | KLKB1 | P03952 |
| GP060-P27169\|Serum paraoxonase/arylesterase 1\|PON1 | PON1 | P27169 |
| GP060-P27169\|Serum paraoxonase/arylesterase 1\|PON1 | PON1 | P27169 |
| GP060-P27169\|Serum paraoxonase/arylesterase 1\|PON1 | PON1 | P27169 |
| GP063-P00734\|Prothrombin\|THRB | THRB | P00734 |
| GP063-P00734\|Prothrombin\|THRB | THRB | P00734 |
| GP064-P02787\|Serotransferrin\|TRFE | TRFE | P02787 |
| GP064-P02787\|Serotransferrin\|TRFE | TRFE | P02787 |
| GP066-Q9UPW8\|Protein unc-13HomologA\|UN13A | UN13A | Q9UPW8 |
| GP066-Q9UPW8\|Protein unc-13HomologA\|UN13A | UN13A | Q9UPW8 |
| GP068-P25311\|Zinc-alpha-2-glycoprotein\|ZA2G | ZA2G | P25311 |

TABLE 7

Mass Spectroscopy Parameters

| Transition No. | HR | P | FDR |
|---|---|---|---|
| 1 | 0.000627004 | 0.000822194 | 0.017391813 |
| 2 | 3.211105911 | 0.004470156 | 0.045059175 |
| 3 | 2.231057601 | 0.001734651 | 0.023628755 |
| 4 | 1.520876905 | 5.59E−05 | 0.005115952 |
| 5 | 1.837783538 | 0.000176337 | 0.006348136 |
| 6 | 1.40562085 | 0.001011918 | 0.018214522 |
| 7 | 1.209703839 | 0.000701319 | 0.016831656 |
| 8 | 4.469501489 | 0.000226663 | 0.006735649 |
| 9 | 1.977144667 | 0.00021306 | 0.006735649 |
| 10 | 2.287887166 | 0.000423227 | 0.011850362 |
| 11 | 1.988151701 | 0.000490231 | 0.013004015 |
| 12 | 2.221200898 | 0.000117597 | 0.005249887 |
| 13 | 2.16732263 | 0.000137689 | 0.005338094 |
| 14 | 3.157467577 | 0.001636036 | 0.023558915 |
| 15 | 6.304743403 | 0.002973123 | 0.033298979 |
| 16 | 3.328016653 | 0.002754052 | 0.032900961 |
| 17 | 1.471706533 | 0.001192277 | 0.019384122 |
| 18 | 1.781858011 | 0.000101507 | 0.005115952 |
| 19 | 7.378623026 | 0.001715405 | 0.023628755 |
| 20 | 1.68099237 | 0.000124997 | 0.005249887 |
| 21 | 11.58630636 | 0.002235992 | 0.028895894 |
| 22 | 0.006627301 | 0.002952436 | 0.033298979 |
| 23 | 3.912630724 | 0.005151944 | 0.049068055 |
| 24 | 2.009471726 | 4.26E−05 | 0.005115952 |
| 25 | 2.206016757 | 0.003352442 | 0.036731107 |
| 26 | 0.164228803 | 0.003478143 | 0.037297538 |
| 27 | 10.6863785 | 0.001349836 | 0.020310346 |
| 28 | 3.077119447 | 0.001010504 | 0.018214522 |
| 29 | 1.191114813 | 0.005159934 | 0.049068055 |
| 30 | 1.508306523 | 0.000698579 | 0.016831656 |
| 31 | 1.302815931 | 7.51E−05 | 0.005115952 |
| 32 | 1.26439213 | 0.001370142 | 0.020310346 |

TABLE 7-continued

Mass Spectroscopy Parameters

| Transition No. | HR | P | FDR |
|---|---|---|---|
| 33 | 6.471779357 | 9.53E−05 | 0.005115952 |
| 34 | 4.780741577 | 2.65E−05 | 0.005115952 |
| 35 | 1.370565469 | 8.10E−05 | 0.005115952 |
| 36 | 1.335404869 | 1.44E−05 | 0.005115952 |
| 37 | 1.551551073 | 9.02E−05 | 0.005115952 |
| 39 | 1.313910204 | 3.59E−05 | 0.005115952 |
| 39 | 2.154403301 | 0.002792543 | 0.032900961 |

In the above table, HR=Hazard Ratio from Continuous Cox proportional hazard models. P=p-value from those models. FDR=false discovery rate by Benjamini-Hochberg method, a p-value corrected for multiple comparisons.

TABLE 8

Glycan and Compositions

| Glycan | Glycan Composition |
|---|---|
| 3200 | $Hex_3HexNAc_2$ |
| 3210 | $Hex_3HexNAc_2Fuc_1$ |
| 3300 | $Hex_3HexNAC_3$ |
| 3310 | $Hex_3HexNAc_3Fuc_1$ |
| 3320 | $Hex_3HexNAc_3Fuc_2$ |
| 3400 | $Hex_3HexNAc_4$ |
| 3410 | $Hex_3HexNAc_4Fuc_1$ |
| 3420 | $Hex_3HexNAc_4Fuc_2$ |
| 3500 | $Hex_3HexNAc_5$ |
| 3510 | $Hex_3HexNAc_5Fuc_1$ |
| 3520 | $Hex_3HexNAc_5Fuc_2$ |

TABLE 8-continued

Glycan and Compositions

| Glycan | Glycan Composition |
| --- | --- |
| 3600 | $Hex_3HexNAc_6$ |
| 3610 | $Hex_3HexNAc_6Fuc_1$ |
| 3620 | $Hex_3HexNAc_6Fuc_2$ |
| 3630 | $Hex_3HexNAc_6Fuc_3$ |
| 3700 | $Hex_3HexNAc_7$ |
| 3710 | $Hex_3HexNAc_7Fuc_1$ |
| 3720 | $Hex_3HexNAc_7Fuc_2$ |
| 3730 | $Hex_3HexNAc_7Fuc_3$ |
| 3740 | $Hex3HexNAc_7Fuc_4$ |
| 4200 | $Hex_4HexNAc_2$ |
| 4210 | $Hex_4HexNAc_2Fuc_1$ |
| 4300 | $Hex_4HexNAc_3$ |
| 4301 | $Hex_4HexNAc_3Neu5Ac_1$ |
| 4310 | $Hex_4HexNAc_3Fuc_1$ |
| 4311 | $Hex_4HexNAc_3Fuc_1Neu5Ac_1$ |
| 4320 | $Hex_4HexNAc_3Fuc_2$ |
| 4400 | $Hex_4HexNAc_4$ |
| 4401 | $Hex_4HexNAc_4Neu5Ac_1$ |
| 4410 | $Hex_4HexNAc_4Fuc_1$ |
| 4411 | $Hex_4HexNAc_4Fuc_1Neu5Ac_1$ |
| 4420 | $Hex_4HexNAc_4Fuc_2$ |
| 4421 | $Hex_4HexNAc_4Fuc_2Neu5Ac_1$ |
| 4430 | $Hex_4HexNAc_4Fuc_3$ |
| 4431 | $Hex_4HexNAc_4Fuc_3Neu5Ac_1$ |
| 4500 | $Hex_4HexNAc_5$ |
| 4501 | $Hex_4HexNAc_5Neu5Ac_1$ |
| 4510 | $Hex_4HexNAc_5Fuc_1$ |
| 4511 | $Hex_4HexNAc_5Fuc_1Neu5Ac_1$ |
| 4520 | $Hex_4HexNAc_5Fuc_2$ |
| 4521 | $Hex_4HexNAc_5Fuc_2Neu5Ac_1$ |
| 4530 | $Hex_4HexNAc_5Fuc_3$ |
| 4531 | $Hex_4HexNAc_5Fuc_3Neu5Ac_1$ |
| 4540 | $Hex_4HexNAc_5Fuc_4$ |
| 4541 | $Hex_4HexNAc_5Fuc_4Neu5Ac_1$ |
| 4600 | $Hex_4HexNAc_6$ |
| 4601 | $Hex_4HexNAc_6Neu5Ac_1$ |
| 4610 | $Hex_4HexNAC_6Fuc_1$ |
| 4611 | $Hex_4HexNAc_6Fuc_1Neu5Ac_1$ |
| 4620 | $Hex_4HexNAc_6Fuc_2$ |
| 4621 | $Hex_4HexNAc_6Fuc_2Neu5Ac_1$ |
| 4630 | $Hex_4HexNAc_6Fuc_3$ |
| 4631 | $Hex_4HexNAc_6Fuc_3Neu5Ac_1$ |
| 4641 | $Hex_4HexNAc_6Fuc_4Neu5Ac_1$ |
| 4650 | $Hex_4HexNAc_6Fuc_5$ |
| 4700 | $Hex_4HexNAc_7$ |
| 4701 | $Hex4HexNAc_7Neu5Ac_1$ |
| 4710 | $Hex_4HexNAc_7Fuc_1$ |
| 4711 | $Hex_4HexNAc_7Fuc_1Neu5Ac_1$ |
| 4720 | $Hex_4HexNAc_7Fuc_2$ |
| 4730 | $Hex_4HexNAc_7Fuc_3$ |
| 5200 | $Hex_5HexNAc_2$ |
| 5210 | $Hex_5HexNAc_2Fuc_1$ |
| 5300 | $Hex_5HexNAc_3$ |
| 5301 | $Hex_5HexNAc_3Neu5Ac_1$ |
| 5310 | $Hex_5HexNAc_3Fuc_1$ |
| 5311 | $Hex_5HexNAc_3Fuc_1Neu5Ac_1$ |
| 5320 | $Hex_5HexNAc_3Fuc_2$ |
| 5400 | $Hex_5HexNAc_4$ |
| 5401 | $Hex_5HexNAc_4Neu5Ac_1$ |
| 5402 | $Hex_5HexNAc_4Neu5Ac_2$ |
| 5410 | $Hex_5HexNAc_4Fuc_1$ |
| 5411 | $Hex_5HexNAc_4Fuc_1Neu5Ac_1$ |
| 5412 | $Hex_5HexNAc_4Fuc_1Neu5Ac_2$ |
| 5420 | $Hex_5HexNAc_4Fuc_2$ |
| 5421 | $Hex_5HexNAc_4Fuc_2Neu5Ac_1$ |
| 5430 | $Hex_5HexNAc_4Fuc_3$ |
| 5431 | $Hex_5HexNAc_4Fuc_3Neu5Ac_1$ |
| 5432 | $Hex_5HexNAc_4Fuc_3Neu5Ac_2$ |
| 5500 | $Hex_5HexNAc_5$ |
| 5501 | $Hex_5HexNAc_5Neu5Ac_1$ |
| 5502 | $Hex_5HexNAc_5Neu5Ac_2$ |
| 5510 | $Hex_5HexNAc_5Fuc_1$ |
| 5511 | $Hex_5HexNAc_5Fuc_1Neu5Ac_1$ |
| 5512 | $Hex_5HexNAc_5Fuc_1Neu5Ac_2$ |
| 5520 | $Hex_5HexNAc_5Fuc_2$ |
| 5521 | $Hex_5HexNAc_5Fuc_2Neu5Ac_1$ |

TABLE 8-continued

Glycan and Compositions

| Glycan | Glycan Composition |
| --- | --- |
| 5522 | $Hex_5HexNAc_5Fuc_2Neu5Ac_2$ |
| 5530 | $Hex_5HexNAc_5Fuc_3$ |
| 5531 | $Hex_5HexNAc_5Fuc_3Neu5Ac_1$ |
| 5541 | $Hex_5HexNAc_5Fuc_4Neu5Ac_1$ |
| 5600 | $Hex_5HexNAc_6$ |
| 5601 | $Hex_5HexNAc_6Neu5Ac_1$ |
| 5602 | $Hex_5HexNAc_6Neu5Ac_2$ |
| 5610 | $Hex_5HexNAc_6Fuc_1$ |
| 5611 | $Hex_5HexNAc_6Fuc_1Neu5Ac_1$ |
| 5612 | $Hex_5HexNAc_6Fuc_1Neu5Ac_2$ |
| 5620 | $Hex_5HexNAc_6Fuc_2$ |
| 5621 | $Hex_5HexNAc_6Fuc_2Neu5Ac_1$ |
| 5631 | $Hex_5HexNAc_6Fuc_3Neu5Ac_1$ |
| 5650 | $Hex_5HexNAc_6Fuc_5$ |
| 5700 | $Hex_5HexNAc_7$ |
| 5701 | $Hex_5HexNAc_7Neu5Ac_1$ |
| 5702 | $Hex_5HexNAc_7Neu5Ac_2$ |
| 5710 | $Hex_5HexNAc_7Fuc_1$ |
| 5711 | $Hex_5HexNAc_7Fuc_1Neu5Ac_1$ |
| 5712 | $Hex_5HexNAc_7Fuc_1Neu5Ac_2$ |
| 5720 | $Hex_5HexNAc_7Fuc_2$ |
| 5721 | $Hex_5HexNAc_7Fuc_2Neu5Ac_1$ |
| 5730 | $Hex_5HexNAc_7Fuc_3$ |
| 5731 | $Hex_5HexNAc_7Fuc_3Neu5Ac_1$ |
| 6200 | $Hex_6HexNAc_2$ |
| 6210 | $Hex_6HexNAc_2Fuc_1$ |
| 6300 | $Hex_6HexNAc_3$ |
| 6301 | $Hex_6HexNAc_3Neu5Ac_1$ |
| 6310 | $Hex_6HexNAc_3Fuc_1$ |
| 6311 | $Hex_6HexNAc_3Fuc_1Neu5Ac_1$ |
| 6320 | $Hex_6HexNAc_3Fuc_2$ |
| 6400 | $Hex_6HexNAc_4$ |
| 6401 | $Hex_6HexNAc_4Neu5Ac_1$ |
| 6402 | $Hex_6HexNAc_4Neu5Ac_2$ |
| 6410 | $Hex_6HexNAc_4Fuc_1$ |
| 6411 | $Hex_6HexNAc_4Fuc_1Neu5Ac_1$ |
| 6412 | $Hex_6HexNAc_4Fuc_1Neu5Ac_2$ |
| 6420 | $Hex_6HexNAc_4Fuc_2$ |
| 6421 | $Hex_6HexNAc_4Fuc_2Neu5Ac_1$ |
| 6432 | $Hex_6HexNAc_4Fuc_3Neu5Ac_2$ |
| 6500 | $Hex_6HexNAc_5$ |
| 6501 | $Hex_6HexNAc_5Neu5Ac_1$ |
| 6502 | $Hex_6HexNAc_5Neu5Ac_2$ |
| 6503 | $Hex_6HexNAc_5Neu5Ac_3$ |
| 6510 | $Hex_6HexNAc_5Fuc_1$ |
| 6511 | $Hex_6HexNAc_5Fuc_1Neu5Ac_1$ |
| 6512 | $Hex_6HexNAc_5Fuc_1Neu5Ac_2$ |
| 6513 | $Hex_6HexNAc_5Fuc_1Neu5Ac_3$ |
| 6520 | $Hex_6HexNAc_5Fuc_2$ |
| 6521 | $Hex_6HexNAc_5Fuc_2Neu5Ac_1$ |
| 6522 | $Hex_6HexNAc_5Fuc_2Neu5Ac_2$ |
| 6530 | $Hex_6HexNAc_5Fuc_3$ |
| 6531 | $Hex_6HexNAc_5Fuc_3Neu5Ac_1$ |
| 6532 | $Hex_6HexNAc_5Fuc_3Neu5Ac_2$ |
| 6540 | $Hex_6HexNAc_5Fuc_4$ |
| 6541 | $Hex_6HexNAc_5Fuc_4Neu5Ac_1$ |
| 6600 | $Hex_6HexNAc_6$ |
| 6601 | $Hex_6HexNAc_6Neu5Ac_1$ |
| 6602 | $Hex_6HexNAc_6Neu5Ac_2$ |
| 6603 | $Hex_6HexNAc_6Neu5Ac_3$ |
| 6610 | $Hex_6HexNAc_6Fuc_1$ |
| 6611 | $Hex_6HexNAc_6Fuc_1Neu5Ac_1$ |
| 6612 | $Hex_6HexNAc_6Fuc_1Neu5Ac_2$ |
| 6613 | $Hex_6HexNAc_6Fuc_1Neu5Ac_3$ |
| 6620 | $Hex_6HexNAc_6Fuc_2$ |
| 6621 | $Hex_6HexNAc_6Fuc_2Neu5Ac_1$ |
| 6622 | $Hex_6HexNAc_6Fuc_2Neu5Ac_2$ |
| 6623 | $Hex_6HexNAc_6Fuc_2Neu5Ac_3$ |
| 6630 | $Hex_6HexNAc_6Fuc_3$ |
| 6631 | $Hex_6HexNAc_6Fuc_3Neu5Ac_1$ |
| 6632 | $Hex_6HexNAc_6Fuc_3Neu5Ac_2$ |
| 6640 | $Hex_6HexNAc_6Fuc_4$ |
| 6641 | $Hex_6HexNAc_6Fuc_4Neu5Ac_1$ |
| 6642 | $Hex_6HexNAc_6Fuc_4Neu5Ac_2$ |
| 6652 | $Hex_6HexNAc_6Fuc_5Neu5Ac_2$ |
| 6700 | $Hex_6HexNAc_7$ |

TABLE 8-continued

Glycan and Compositions

| Glycan | Glycan Composition |
|---|---|
| 6701 | $Hex_6HexNAc_7Neu5Ac_1$ |
| 6711 | $Hex_6HexNAc_7Fuc_1Neu5Ac_1$ |
| 6721 | $Hex_6HexNAc_7Fuc_2Neu5Ac_1$ |
| 6703 | $Hex_6HexNAc_7Neu5Ac_3$ |
| 6713 | $Hex_6HexNAc_7Fuc_1Neu5Ac_3$ |
| 6710 | $Hex_6HexNAc_7Fuc_1$ |
| 6711 | $Hex_6HexNAc_7Fuc_1Neu5Ac_1$ |
| 6712 | $Hex_6HexNAc_7Fuc_1Neu5Ac_2$ |
| 6713 | $Hex_6HexNAc_7Fuc_1Neu5Ac_3$ |
| 6720 | $Hex_6HexNAc_7Fuc_2$ |
| 6721 | $Hex_6HexNAc_7Fuc_2Neu5Ac_1$ |
| 6730 | $Hex_6HexNAc_7Fuc_3$ |
| 6731 | $Hex_6HexNAc_7Fuc_3Neu5Ac_1$ |
| 6740 | $Hex_6HexNAc_7Fuc_4$ |
| 7200 | $Hex_7HexNAc_2$ |
| 7210 | $Hex_7HexNAc_2Fuc_1$ |
| 7400 | $Hex_7HexNAc_4$ |
| 7401 | $Hex_7HexNAc_4Neu5Ac_1$ |
| 7410 | $Hex_7HexNAc_4Fuc_1$ |
| 7411 | $Hex_7HexNAc_4Fuc_1Neu5Ac_1$ |
| 7412 | $Hex_7HexNAc_4Fuc_1Neu5Ac_2$ |
| 7420 | $Hex_7HexNAc_4Fuc_2$ |
| 7421 | $Hex_7HexNAc_4Fuc_2Neu5Ac_1$ |
| 7430 | $Hex_7HexNAc_4Fuc_3$ |
| 7431 | $Hex_7HexNAc_4Fuc_3Neu5Ac_1$ |
| 7432 | $Hex_7HexNAc_4Fuc_3Neu5Ac_2$ |
| 7500 | $Hex_7HexNAc_5$ |
| 7501 | $Hex_7HexNAc_5Neu5Ac_1$ |
| 7510 | $Hex_7HexNAc_5Fuc_1$ |
| 7511 | $Hex_7HexNAc_5Fuc_1Neu5Ac_1$ |
| 7512 | $Hex_7HexNAc_5Fuc_1Neu5Ac_2$ |
| 7600 | $Hex_7HexNAc_6$ |
| 7601 | $Hex_7HexNAc_6Neu5Ac_1$ |
| 7602 | $Hex_7HexNAc_6Neu5Ac_2$ |
| 7603 | $Hex_7HexNAc_6Neu5Ac_3$ |
| 7604 | $Hex_7HexNAc_6Neu5Ac_4$ |
| 7610 | $Hex_7HexNAc_6Fuc_1$ |
| 7611 | $Hex_7HexNAc_6Fuc_1Neu5Ac_1$ |
| 7612 | $Hex_7HexNAc_6Fuc_1Neu5Ac_2$ |
| 7613 | $Hex_7HexNAc_6Fuc_1Neu5Ac_3$ |
| 7614 | $Hex_7HexNAc_6Fuc_1Neu5Ac_4$ |

TABLE 8-continued

Glycan and Compositions

| Glycan | Glycan Composition |
|---|---|
| 7620 | $Hex_7HexNAC_6Fuc_2$ |
| 7621 | $Hex_7HexNAc_6Fuc_2Neu5Ac_1$ |
| 7622 | $Hex_7HexNAc_6Fuc_2Neu5Ac_2$ |
| 7623 | $Hex_7HexNAc_6Fuc_2Neu5Ac_3$ |
| 7632 | $Hex_7HexNAc_6Fuc_3Neu5Ac_2$ |
| 7640 | $Hex_7HexNAc_6Fuc_4$ |
| 7700 | $Hex_7HexNAc_7$ |
| 7701 | $Hex_7HexNAc_7Neu5Ac_1$ |
| 7702 | $Hex_7HexNAc_7Neu5Ac_2$ |
| 7703 | $Hex_7HexNAc_7Neu5Ac_3$ |
| 7710 | $Hex_7HexNAc_7Fuc_1$ |
| 7711 | $Hex_7HexNAc_7Fuc_1Neu5Ac_1$ |
| 7712 | $Hex_7HexNAc_7Fuc_1Neu5Ac_2$ |
| 7713 | $Hex_7HexNAc_7Fuc_1Neu5Ac_3$ |
| 7714 | $Hex_7HexNAc_7Fuc_1Neu5Ac_4$ |
| 7720 | $Hex_7HexNAc_7Fuc_2$ |
| 7721 | $Hex_7HexNAc_7Fuc_2Neu5Ac_1$ |
| 7722 | $Hex_7HexNAc_7Fuc_2Neu5Ac_2$ |
| 7730 | $Hex_7HexNAc_7Fuc_3$ |
| 7731 | $Hex_7HexNAc_7Fuc_3Neu5Ac_1$ |
| 7732 | $Hex_7HexNAc_7Fuc_3Neu5Ac_2$ |
| 7740 | $Hex_7HexNAc_7Fuc_4$ |
| 7741 | $Hex_7HexNAc_7Fuc_4Neu5Ac_1$ |
| 7751 | $Hex_7HexNAc_7Fuc_5Neu5Ac_1$ |
| 8200 | $Hex_8HexNAc_2$ |
| 9200 | $Hex_9HexNAc_2$ |
| 9210 | $Hex_9HexNAc_2Fuc_1$ |
| 10200 | $Hex_10HexNAc_2$ |
| 11200 | $Hex_11HexNAc_2$ |
| 12200 | $Hex_12HexNAc_2$ |

The embodiments and examples described above are intended to be merely illustrative and non-limiting. Those skilled in the art will recognize or will be able to ascertain using no more than routine experimentation, numerous equivalents of specific compounds, materials and procedures described herein. All such equivalents are considered to be within the scope and are encompassed by the appended claims.

What is claimed is:

1. A method for classifying a biological sample from an individual having clear cell renal cell carcinoma (ccRCC), the method comprising:

quantifying one or more glycopeptides to obtain quantification information, wherein the quantifying is based on information obtained from a liquid chromatography/mass spectrometry (LC/MS) analysis of a prepared sample from the biological sample for the LC/MS analysis, wherein the one or more glycopeptides include one or more of SEQ ID NO:1 comprising glycan 7603 at residue 271; SEQ ID NO:2 comprising glycan 5402 at residue 402-MC; SEQ ID NO:3 comprising glycan 7614 at residue 72; SEQ ID NO:4 comprising glycan 5401 at residue 3411; SEQ ID NO:5 comprising glycan 1111 at residue 74; SEQ ID NO:6 comprising glycan 1300 at residue 74; SEQ ID NO:7 comprising glycan 2110 at residue 74; SEQ ID NO:8 comprising glycan 1102 at residue 74-Aoff; SEQ ID NO:9 comprising glycan 5402 at residue 98; SEQ ID NO:10 comprising glycan 5410 at residue 98; SEQ ID NO:11 comprising glycan 6510 at residue 98; SEQ ID NO:12 comprising glycan 6530 at residue 98; SEQ ID NO:13 comprising glycan 9800 at residue 98; SEQ ID NO:14 comprising glycan 5421 at residue 135; SEQ ID NO:15 comprising glycan 8500 at residue 135; SEQ ID NO:16 comprising glycan 5402 at residue 174; SEQ ID NO:17 comprising glycan 6503 at residue 366; SEQ ID NO:18 comprising glycan 6513 at residue 366; SEQ ID NO:19 comprising glycan 5400 at residue 291; SEQ ID NO:20 comprising glycan 6503 at residue 291; SEQ ID NO:21 comprising glycan 5402 at residue 437; SEQ ID NO:22 comprising glycan 5402 at residue 156; SEQ ID NO:23 comprising glycan 6503 at residue 176; SEQ ID NO:24 comprising glycan 6513 at residue 176; SEQ ID NO:25 comprising glycan 6513 at residue 241; SEQ ID NO:26 comprising glycan 5411 at residue 297; SEQ ID NO:27 comprising glycan 5411 at residue 71; SEQ ID NO:28 comprising glycan 5402 at residue 494; SEQ ID NO:29 comprising glycan 6503 at residue 494; SEQ ID NO:30 comprising glycan 5420 at residue 324; SEQ ID NO:31 comprising glycan 6501 at residue 324; SEQ ID NO:32 comprising glycan 6502 at residue 324; SEQ ID NO:33 comprising glycan 5401 at residue 121; SEQ ID NO:34 comprising glycan 5402 at residue 121; SEQ ID NO:35 comprising glycan 5400 at residue 630; SEQ ID NO:36 comprising glycan 6502 at residue 630; SEQ ID NO:37 comprising glycan 5431 at residue 1005; SEQ ID NO:38 comprising glycan 7420 at residue 1005; or SEQ ID NO:39 comprising glycan 5412 at residue 112;

inputting the quantification information of the one or more glycopeptides into a trained machine learning model to generate an output probability; and outputting the output probability for ccRCC progression-free survival classification of the biological sample.

2. The method of claim 1, wherein the output probability is designed for predicting progression-free survival for the individual having ccRCC based on whether the output probability is above or below a classification for ccRCC progression-free survival.

3. The method of claim 1, further comprising predicting progression-free survival for the individual having ccRCC based on whether the output probability is above or below the threshold for the classification for ccRCC progression-free survival.

4. The method of claim 3, wherein the predicting progression-free survival for the individual having ccRCC comprises predicting progression-free survival of the individual having ccRCC after surgical resection of a primary tumor.

5. The method of claim 3, the predicting progression-free survival for the individual having ccRCC comprises predicting progression-free survival of the individual having ccRCC after a nephrectomy, and wherein the biological sample was collected from the individual prior to the nephrectomy.

6. The method of claim 1, further comprising training the machine learning model.

7. The method of claim 1, wherein the quantifying one or more glycopeptides comprises quantifying three or more or quantifying five or more of the one or more glycopeptides.

8. The method of claim 1, wherein the LC/MS analysis comprises multiple-reaction-monitoring (MRM).

9. The method of claim 8, wherein the MRM LC/MS analysis comprises monitoring one or more of transitions 1-39.

10. The method of claim 9, wherein the MRM LC/MS analysis comprises monitoring transitions 15, 19, 21, 27, and 33.

11. The method of claim 1, wherein the LC/MS analysis comprises use of a triple quadrupole (QQQ) mass spectrometer.

12. The method of claim 1, further comprising preparing the prepared sample from the biological sample for the LC/MS analysis.

13. The method of claim 1, further comprising performing the LC/MS analysis on the biological sample.

14. The method of claim 1, further comprising obtaining the biological sample from the individual.

15. The method of claim 1, wherein the biological sample is a blood sample, a plasma sample, or a serum sample.

16. The method of claim 1, wherein the biological sample is obtained from the individual after surgical resection of a primary tumor.

17. The method of claim 1, wherein the individual has stage 1 or stage 2 ccRCC.

18. A method for classifying a biological sample from an individual having clear cell renal cell carcinoma (ccRCC), the method comprising:

quantifying one or more glycopeptides to obtain quantification information, wherein the quantifying is based on information obtained from a liquid chromatography/mass spectrometry (LC/MS) analysis of a prepared sample from the biological sample for the LC/MS analysis, wherein the one or more glycopeptides include one or more of SEQ ID NO:1 comprising glycan 7603 at residue 271; SEQ ID NO:2 comprising glycan 5402 at residue 402-MC; SEQ ID NO:3 comprising glycan 7614 at residue 72; SEQ ID NO:4 comprising glycan 5401 at residue 3411; SEQ ID NO:5 comprising glycan 1111 at residue 74; SEQ ID NO:6 comprising glycan 1300 at residue 74; SEQ ID NO:7 comprising glycan 2110 at residue 74; SEQ ID NO:8 comprising glycan 1102 at residue 74-Aoff; SEQ ID NO:9 comprising glycan 5402 at residue 98; SEQ ID NO:10 comprising glycan 5410 at residue 98; SEQ ID NO:11 comprising glycan 6510 at residue 98; SEQ ID NO:12 comprising glycan 6530 at residue 98; SEQ ID NO:13 comprising glycan 9800 at residue 98; SEQ ID NO:14 comprising glycan 5421 at residue 135; SEQ ID NO:15 comprising glycan 8500 at residue 135; SEQ ID NO:16 comprising glycan 5402 at residue 174; SEQ ID NO:17 comprising glycan 6503 at residue 366; SEQ ID NO:18 comprising glycan 6513 at residue 366; SEQ ID NO:19 comprising glycan 5400 at residue 291; SEQ ID NO:20 comprising glycan 6503 at residue 291; SEQ ID NO:21 comprising glycan 5402 at residue 437; SEQ ID NO:22 comprising glycan 5402 at residue 156; SEQ ID NO:23 comprising glycan 6503 at residue 176; SEQ ID NO:24 comprising glycan 6513 at residue 176; SEQ ID NO:25 comprising glycan 6513 at residue 241; SEQ ID NO:26 comprising glycan 5411 at residue 297; SEQ ID NO:27 comprising glycan 5411 at residue 71; SEQ ID NO:28 comprising glycan 5402 at residue 494; SEQ ID NO:29 comprising glycan 6503 at residue 494; SEQ ID NO:30 comprising glycan 5420 at residue 324; SEQ ID NO:31 comprising glycan 6501 at residue 324; SEQ ID NO:32 comprising glycan 6502 at residue 324; SEQ ID NO:33 comprising glycan 5401 at residue 121; SEQ ID NO:34 comprising glycan 5402 at residue 121; SEQ ID NO:35 comprising glycan 5400 at residue 630; SEQ ID NO:36 comprising glycan 6502 at residue 630; SEQ ID NO:37 comprising glycan 5431 at residue 1005; SEQ ID NO:38 comprising glycan 7420 at residue 1005; or SEQ ID NO:39 comprising glycan 5412 at residue 112; and generating a multivariable score based on the quantification information for ccRCC progression-free survival classification of the biological sample, wherein the multivariable score is based on a sum of instances of the one or more glycopeptides being above an associated cut-off value.

19. The method of claim 18, wherein the multivariable score is designed for predicting progression-free survival for the individual having ccRCC.

20. The method of claim 18, further comprising predicting progression-free survival for the individual having ccRCC based on the multivariable score.

21. The method of claim 20, wherein the predicting progression-free survival for the individual having ccRCC comprises predicting progression-free survival of the individual having ccRCC when less than 10 of the one or more glycopeptides are above an associated cut-off value.

22. The method of claim 18, wherein the quantifying one or more glycopeptides comprises quantifying 11 or more, quantifying 21 or more, or quantifying 31 or more of the one or more glycopeptides.

23. The method of claim 18, wherein the LC/MS analysis comprises multiple-reaction-monitoring (MRM).

24. The method of claim 23, wherein the MRM LC/MS analysis comprises monitoring one or more of transitions 1-39.

25. The method of claim 24, wherein the MRM LC/MS analysis comprises monitoring transitions 15, 19, 21, 27, and 33.

26. The method of claim 18, wherein the LC/MS analysis comprises use of a triple quadrupole (QQQ) mass spectrometer.

27. The method of claim 18, further comprising preparing the prepared sample from the biological sample for the LC/MS analysis.

28. The method of claim 19, further comprising performing the LC/MS analysis on the biological sample.

29. The method of claim 18, further comprising obtaining the biological sample from the individual.

30. The method of claim 17, wherein the biological sample is a blood sample, a plasma sample, or a serum sample.

31. The method of claim 17, wherein the individual has stage 1 or stage 2 ccRCC.

32. The method of claim 17, wherein the biological sample is obtained from the individual after surgical resection of a primary tumor.

33. The method of claim 20, further comprising administering a therapeutically effective amount of a therapeutic agent to the individual based on the predicting progression-free survival for the individual having ccRCC.

34. A method comprising:
(a) obtaining a biological sample from an individual having clear cell renal cell carcinoma (ccRCC);
(b) preparing the biological sample for a liquid chromatography/mass spectrometry (LC/MS) analysis comprising multiple-reaction-monitoring (MRM); and
(c) performing the MRM LC/MS analysis comprising monitoring one or more of transitions 1-39.

35. The method of claim 34, wherein the MRM LC/MS analysis comprising monitoring transitions 1-39.

* * * * *

SEQUENCE LISTING

<160> NUMBER OF SEQ ID NOS: 39

<210> SEQ ID NO 1
<211> LENGTH: 16
<212> TYPE: PRT
<213> ORGANISM: Artificial Sequence
<220> FEATURE:
<223> OTHER INFORMATION: AACT-GP005_271_7603

<400> SEQUENCE: 1

Tyr Thr Gly Asn Ala Ser Ala Leu Phe Ile Leu Pro Asp Gln Asp Lys
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: AFAM-GP006_402_5402

<400> SEQUENCE: 2

Tyr Ala Glu Asp Lys Phe Asn Glu Thr Thr Glu Lys
1               5                   10

```
<210> SEQ ID NO 3
<211> LENGTH: 24
<212> TYPE: PRT
<213> ORGANISM: Artificial Sequence
<220> FEATURE:
<223> OTHER INFORMATION: AGP12-GP007&008_72MC_7614

<400> SEQUENCE: 3

Ser Val Gln Glu Ile Gln Ala Thr Phe Phe Tyr Phe Thr Pro Asn Lys
1               5                   10                  15

Thr Glu Asp Thr Ile Phe Leu Arg
            20

<210> SEQ ID NO 4
<211> LENGTH: 15
<212> TYPE: PRT
<213> ORGANISM: Artificial Sequence
<220> FEATURE:
<223> OTHER INFORMATION: APOB-GP013_3411_5401

<400> SEQUENCE: 4

Phe Val Glu Gly Ser His Asn Ser Thr Val Ser Leu Thr Thr Lys
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: APOC3-GP012_74_1111

<400> SEQUENCE: 5

Phe Ser Glu Phe Trp Asp Leu Asp Pro Glu Val Arg Pro Thr Ser Ala
1               5                   10                  15

Val Ala Ala

<210> SEQ ID NO 6
<211> LENGTH: 19
<212> TYPE: PRT
<213> ORGANISM: Artificial Sequence
<220> FEATURE:
<223> OTHER INFORMATION: APOC3-GP012_74_1300

<400> SEQUENCE: 6

Phe Ser Glu Phe Trp Asp Leu Asp Pro Glu Val Arg Pro Thr Ser Ala
1               5                   10                  15

Val Ala Ala

<210> SEQ ID NO 7
<211> LENGTH: 19
<212> TYPE: PRT
<213> ORGANISM: Artificial Sequence
<220> FEATURE:
<223> OTHER INFORMATION: APOC3-GP012_74_2110

<400> SEQUENCE: 7

Phe Ser Glu Phe Trp Asp Leu Asp Pro Glu Val Arg Pro Thr Ser Ala
1               5                   10                  15

Val Ala Ala

<210> SEQ ID NO 8
<211> LENGTH: 18
<212> TYPE: PRT
<213> ORGANISM: Artificial Sequence
<220> FEATURE:
```

<223> OTHER INFORMATION: APOC3-GP012_74Aoff_1102

<400> SEQUENCE: 8

Phe Ser Glu Phe Trp Asp Leu Asp Pro Glu Val Arg Pro Thr Ser Ala
1               5                   10                  15

Val Ala

<210> SEQ ID NO 9
<211> LENGTH: 22
<212> TYPE: PRT
<213> ORGANISM: Artificial Sequence
<220> FEATURE:
<223> OTHER INFORMATION: APOD-GP014_98_5402/5421

<400> SEQUENCE: 9

Ala Asp Gly Thr Val Asn Gln Ile Glu Gly Glu Ala Thr Pro Val Asn
1               5                   10                  15

Leu Thr Glu Pro Ala Lys
            20

<210> SEQ ID NO 10
<211> LENGTH: 22
<212> TYPE: PRT
<213> ORGANISM: Artificial Sequence
<220> FEATURE:
<223> OTHER INFORMATION: APOD-GP014_98_5410

<400> SEQUENCE: 10

Ala Asp Gly Thr Val Asn Gln Ile Glu Gly Glu Ala Thr Pro Val Asn
1               5                   10                  15

Leu Thr Glu Pro Ala Lys
            20

<210> SEQ ID NO 11
<211> LENGTH: 22
<212> TYPE: PRT
<213> ORGANISM: Artificial Sequence
<220> FEATURE:
<223> OTHER INFORMATION: APOD-GP014_98_6510

<400> SEQUENCE: 11

Ala Asp Gly Thr Val Asn Gln Ile Glu Gly Glu Ala Thr Pro Val Asn
1               5                   10                  15

Leu Thr Glu Pro Ala Lys
            20

<210> SEQ ID NO 12
<211> LENGTH: 22
<212> TYPE: PRT
<213> ORGANISM: Artificial Sequence
<220> FEATURE:
<223> OTHER INFORMATION: APOD-GP014_98_6530

<400> SEQUENCE: 12

Ala Asp Gly Thr Val Asn Gln Ile Glu Gly Glu Ala Thr Pro Val Asn
1               5                   10                  15

Leu Thr Glu Pro Ala Lys
            20

<210> SEQ ID NO 13
<211> LENGTH: 22
<212> TYPE: PRT
<213> ORGANISM: Artificial Sequence
<220> FEATURE:

<223> OTHER INFORMATION: APOD-GP014_98_9800

<400> SEQUENCE: 13

Ala Asp Gly Thr Val Asn Gln Ile Glu Gly Glu Ala Thr Pro Val Asn
1               5                   10                  15

Leu Thr Glu Pro Ala Lys
            20

<210> SEQ ID NO 14
<211> LENGTH: 23
<212> TYPE: PRT
<213> ORGANISM: Artificial Sequence
<220> FEATURE:
<223> OTHER INFORMATION: APOM-GP016_135_5421

<400> SEQUENCE: 14

Thr Glu Leu Phe Ser Ser Ser Cys Pro Gly Gly Ile Met Leu Asn Glu
1               5                   10                  15

Thr Gly Gln Gly Tyr Gln Arg
            20

<210> SEQ ID NO 15
<211> LENGTH: 23
<212> TYPE: PRT
<213> ORGANISM: Artificial Sequence
<220> FEATURE:
<223> OTHER INFORMATION: APOM-GP016_135_8500

<400> SEQUENCE: 15

Thr Glu Leu Phe Ser Ser Ser Cys Pro Gly Gly Ile Met Leu Asn Glu
1               5                   10                  15

Thr Gly Gln Gly Tyr Gln Arg
            20

<210> SEQ ID NO 16
<211> LENGTH: 32
<212> TYPE: PRT
<213> ORGANISM: Artificial Sequence
<220> FEATURE:
<223> OTHER INFORMATION: C1S-GP020_174_5402

<400> SEQUENCE: 16

Asn Cys Gly Val Asn Cys Ser Gly Asp Val Phe Thr Ala Leu Ile Gly
1               5                   10                  15

Glu Ile Ala Ser Pro Asn Tyr Pro Lys Pro Tyr Pro Glu Asn Ser Arg
            20                  25                  30

<210> SEQ ID NO 17
<211> LENGTH: 15
<212> TYPE: PRT
<213> ORGANISM: Artificial Sequence
<220> FEATURE:
<223> OTHER INFORMATION: CAN3-GP022_366_6503

<400> SEQUENCE: 17

Asn Pro Trp Gly Gln Val Glu Trp Asn Gly Ser Trp Ser Asp Arg
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: CAN3-GP022_366_6513

<400> SEQUENCE: 18

Asn Pro Trp Gly Gln Val Glu Trp Asn Gly Ser Trp Ser Asp Arg
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: CLUS-GP026_291_5400

<400> SEQUENCE: 19

His Asn Ser Thr Gly Cys Leu Arg
1               5

<210> SEQ ID NO 20
<211> LENGTH: 8
<212> TYPE: PRT
<213> ORGANISM: Artificial Sequence
<220> FEATURE:
<223> OTHER INFORMATION: CLUS-GP026_291_6503

<400> SEQUENCE: 20

His Asn Ser Thr Gly Cys Leu Arg
1               5

<210> SEQ ID NO 21
<211> LENGTH: 14
<212> TYPE: PRT
<213> ORGANISM: Artificial Sequence
<220> FEATURE:
<223> OTHER INFORMATION: CO8A-GP033_437_5402

<400> SEQUENCE: 21

Gly Gly Ser Ser Gly Trp Ser Gly Gly Leu Ala Gln Asn Arg
1               5                   10

<210> SEQ ID NO 22
<211> LENGTH: 15
<212> TYPE: PRT
<213> ORGANISM: Artificial Sequence
<220> FEATURE:
<223> OTHER INFORMATION: FETUA-GP036_156_5402/5421

<400> SEQUENCE: 22

Val Cys Gln Asp Cys Pro Leu Leu Ala Pro Leu Asn Asp Thr Arg
1               5                   10                  15

<210> SEQ ID NO 23
<211> LENGTH: 22
<212> TYPE: PRT
<213> ORGANISM: Artificial Sequence
<220> FEATURE:
<223> OTHER INFORMATION: FETUA-GP036_176_6503

<400> SEQUENCE: 23

Ala Ala Leu Ala Ala Phe Asn Ala Gln Asn Asn Gly Ser Asn Phe Gln
1               5                   10                  15

Leu Glu Glu Ile Ser Arg
            20

<210> SEQ ID NO 24
<211> LENGTH: 22
<212> TYPE: PRT
<213> ORGANISM: Artificial Sequence
<220> FEATURE:

<223> OTHER INFORMATION: FETUA-GP036_176_6513

<400> SEQUENCE: 24

Ala Ala Leu Ala Ala Phe Asn Ala Gln Asn Asn Gly Ser Asn Phe Gln
1               5                   10                  15

Leu Glu Glu Ile Ser Arg
            20

<210> SEQ ID NO 25
<211> LENGTH: 16
<212> TYPE: PRT
<213> ORGANISM: Artificial Sequence
<220> FEATURE:
<223> OTHER INFORMATION: HPT-GP044_241_6513

<400> SEQUENCE: 25

Val Val Leu His Pro Asn Tyr Ser Gln Val Asp Ile Gly Leu Ile Lys
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: IgG1-GP048_297_5411

<400> SEQUENCE: 26

Glu Glu Gln Tyr Asn Ser Thr Tyr Arg
1               5

<210> SEQ ID NO 27
<211> LENGTH: 11
<212> TYPE: PRT
<213> ORGANISM: Artificial Sequence
<220> FEATURE:
<223> OTHER INFORMATION: IgJ-GP052_71_5411

<400> SEQUENCE: 27

Glu Asn Ile Ser Asp Pro Thr Ser Pro Leu Arg
1               5                   10

<210> SEQ ID NO 28
<211> LENGTH: 19
<212> TYPE: PRT
<213> ORGANISM: Artificial Sequence
<220> FEATURE:
<223> OTHER INFORMATION: KLKB1-GP056_494_5402

<400> SEQUENCE: 28

Leu Gln Ala Pro Leu Asn Tyr Thr Glu Phe Gln Lys Pro Ile Cys Leu
1               5                   10                  15

Pro Ser Lys

<210> SEQ ID NO 29
<211> LENGTH: 19
<212> TYPE: PRT
<213> ORGANISM: Artificial Sequence
<220> FEATURE:
<223> OTHER INFORMATION: KLKB1-GP056_494_6503

<400> SEQUENCE: 29

Leu Gln Ala Pro Leu Asn Tyr Thr Glu Phe Gln Lys Pro Ile Cys Leu
1               5                   10                  15

Pro Ser Lys

```
<210> SEQ ID NO 30
<211> LENGTH: 22
<212> TYPE: PRT
<213> ORGANISM: Artificial Sequence
<220> FEATURE:
<223> OTHER INFORMATION: PON1-GP060_324_5420

<400> SEQUENCE: 30

Val Thr Gln Val Tyr Ala Glu Asn Gly Thr Val Leu Gln Gly Ser Thr
1               5                   10                  15

Val Ala Ser Val Tyr Lys
            20

<210> SEQ ID NO 31
<211> LENGTH: 22
<212> TYPE: PRT
<213> ORGANISM: Artificial Sequence
<220> FEATURE:
<223> OTHER INFORMATION: PON1-GP060_324_6501

<400> SEQUENCE: 31

Val Thr Gln Val Tyr Ala Glu Asn Gly Thr Val Leu Gln Gly Ser Thr
1               5                   10                  15

Val Ala Ser Val Tyr Lys
            20

<210> SEQ ID NO 32
<211> LENGTH: 22
<212> TYPE: PRT
<213> ORGANISM: Artificial Sequence
<220> FEATURE:
<223> OTHER INFORMATION: PON1-GP060_324_6502

<400> SEQUENCE: 32

Val Thr Gln Val Tyr Ala Glu Asn Gly Thr Val Leu Gln Gly Ser Thr
1               5                   10                  15

Val Ala Ser Val Tyr Lys
            20

<210> SEQ ID NO 33
<211> LENGTH: 7
<212> TYPE: PRT
<213> ORGANISM: Artificial Sequence
<220> FEATURE:
<223> OTHER INFORMATION: THRB-GP063_121_5420/5401

<400> SEQUENCE: 33

Gly His Val Asn Ile Thr Arg
1               5

<210> SEQ ID NO 34
<211> LENGTH: 7
<212> TYPE: PRT
<213> ORGANISM: Artificial Sequence
<220> FEATURE:
<223> OTHER INFORMATION: THRB-GP063_121_5421/5402

<400> SEQUENCE: 34

Gly His Val Asn Ile Thr Arg
1               5

<210> SEQ ID NO 35
<211> LENGTH: 21
<212> TYPE: PRT
<213> ORGANISM: Artificial Sequence
```

-continued

```
<220> FEATURE:
<223> OTHER INFORMATION: TRFE-GP064_630_5400

<400> SEQUENCE: 35

Gln Gln Gln His Leu Phe Gly Ser Asn Val Thr Asp Cys Ser Gly Asn
1               5                   10                  15

Phe Cys Leu Phe Arg
            20

<210> SEQ ID NO 36
<211> LENGTH: 21
<212> TYPE: PRT
<213> ORGANISM: Artificial Sequence
<220> FEATURE:
<223> OTHER INFORMATION: TRFE-GP064_630_6502

<400> SEQUENCE: 36

Gln Gln Gln His Leu Phe Gly Ser Asn Val Thr Asp Cys Ser Gly Asn
1               5                   10                  15

Phe Cys Leu Phe Arg
            20

<210> SEQ ID NO 37
<211> LENGTH: 20
<212> TYPE: PRT
<213> ORGANISM: Artificial Sequence
<220> FEATURE:
<223> OTHER INFORMATION: UN13A-GP066_1005_5431

<400> SEQUENCE: 37

Ala Cys Leu Asn Ser Thr Tyr Glu Tyr Ile Phe Asn Asn Cys His Glu
1               5                   10                  15

Leu Tyr Ser Arg
            20

<210> SEQ ID NO 38
<211> LENGTH: 20
<212> TYPE: PRT
<213> ORGANISM: Artificial Sequence
<220> FEATURE:
<223> OTHER INFORMATION: UN13A-GP066_1005_7420

<400> SEQUENCE: 38

Ala Cys Leu Asn Ser Thr Tyr Glu Tyr Ile Phe Asn Asn Cys His Glu
1               5                   10                  15

Leu Tyr Ser Arg
            20

<210> SEQ ID NO 39
<211> LENGTH: 18
<212> TYPE: PRT
<213> ORGANISM: Artificial Sequence
<220> FEATURE:
<223> OTHER INFORMATION: ZA2G-GP068_112_5412

<400> SEQUENCE: 39

Asp Ile Val Glu Tyr Tyr Asn Asp Ser Asn Gly Ser His Val Leu Gln
1               5                   10                  15

Gly Arg
```